(12) United States Patent
Manaka et al.

(10) Patent No.: US 7,360,416 B2
(45) Date of Patent: Apr. 22, 2008

(54) NON-CONTACT CONDENSATION DETECTING APPARATUS

(75) Inventors: Junji Manaka, Aichi (JP); Kazutoshi Nagai, Aichi (JP)

(73) Assignee: Ricoh Company, Ltd., Tokyo (JP)

( * ) Notice: Subject to any disclaimer, the term of this patent is extended or adjusted under 35 U.S.C. 154(b) by 40 days.

(21) Appl. No.: 11/481,097

(22) Filed: Jul. 6, 2006

(65) Prior Publication Data

US 2007/0113644 A1    May 24, 2007

(30) Foreign Application Priority Data

Jul. 7, 2005   (JP) .............................. 2005-198744
Aug. 24, 2005   (JP) .............................. 2005-241959
May 29, 2006   (JP) .............................. 2006-147865

(51) Int. Cl.
*G01F 1/68* (2006.01)
(52) U.S. Cl. .................................................. 73/204.26
(58) Field of Classification Search ............. 73/204.26, 73/204.25, 204.24, 204.23, 204.27, 204.15; 338/25
See application file for complete search history.

(56) References Cited

U.S. PATENT DOCUMENTS

| 5,313,832 | A  | * | 5/1994  | Stephan et al. | ........... | 73/204.26 |
| 6,245,444 | B1 | * | 6/2001  | Marcus et al.  | .............. | 428/616   |
| 6,796,172 | B2 | * | 9/2004  | Blakley et al. | ........... | 73/204.26 |
| 6,862,930 | B1 | * | 3/2005  | Kohno et al.   | ............ | 73/204.26 |
| 2004/0261520 | A1 | * | 12/2004 | Lotters | ..................... | 73/204.26 |

FOREIGN PATENT DOCUMENTS

| JP | 1-127942 A | 5/1989 |
| JP | 3-78648 A | 4/1991 |
| JP | 4-128643 A | 4/1992 |
| JP | 4-251067 A | 9/1992 |
| JP | 6-18465 A | 1/1994 |
| JP | 06018465 | * 1/1994 |
| JP | 2621982 B2 | 4/1997 |
| JP | 2780911 B2 | 5/1998 |
| JP | 2801156 B2 | 7/1998 |
| JP | 2889909 B2 | 2/1999 |
| JP | 11-118553 A | 4/1999 |
| JP | 11-337261 A | 12/1999 |
| JP | 3049122 A | 3/2000 |
| JP | 2001-301273 A | 10/2001 |
| JP | 3292523 B2 | 3/2002 |

(Continued)

*Primary Examiner*—Jewel Thompson
(74) *Attorney, Agent, or Firm*—Dickstein Shapiro LLP

(57) ABSTRACT

A disclosed detector element includes a substrate including a void, a heating unit including a heat generating electrode bridged across the void, and a temperature sensor including a temperature sensor electrode provided above the void. The heat generating electrode and the temperature sensor electrode are warped, cantilevered, and standing up in space. The temperature sensor measures heat quantity transported from the heating unit. Distribution of an atmosphere surrounding an object surface with respect to the object surface, and the transportation state of the atmosphere are measured by using at least one of temperature, humidity, a direction or velocity of flow, pressure, and composition of gas in the atmosphere. Behavior of the gas adhering and aggregating onto the object surface, and behavior of aggregated liquid undergoing transpiration from the object surface are detected, based on the distribution and the transportation state measured.

6 Claims, 52 Drawing Sheets

FOREIGN PATENT DOCUMENTS

| | | |
|---|---|---|
| JP | 2002-310876 A | 10/2002 |
| JP | 2002-369885 A | 12/2002 |
| JP | 2004-029563 A | 1/2004 |
| JP | 2004-83385 A | 3/2004 |
| JP | 2004-066927 A | 4/2004 |
| JP | 2004-216883 A | 8/2004 |
| JP | 2005-170525 A | 6/2005 |
| WO | WO 00/14522 A1 | 3/2000 |
| WO | WO 01/88612 A1 | 11/2001 |

* cited by examiner

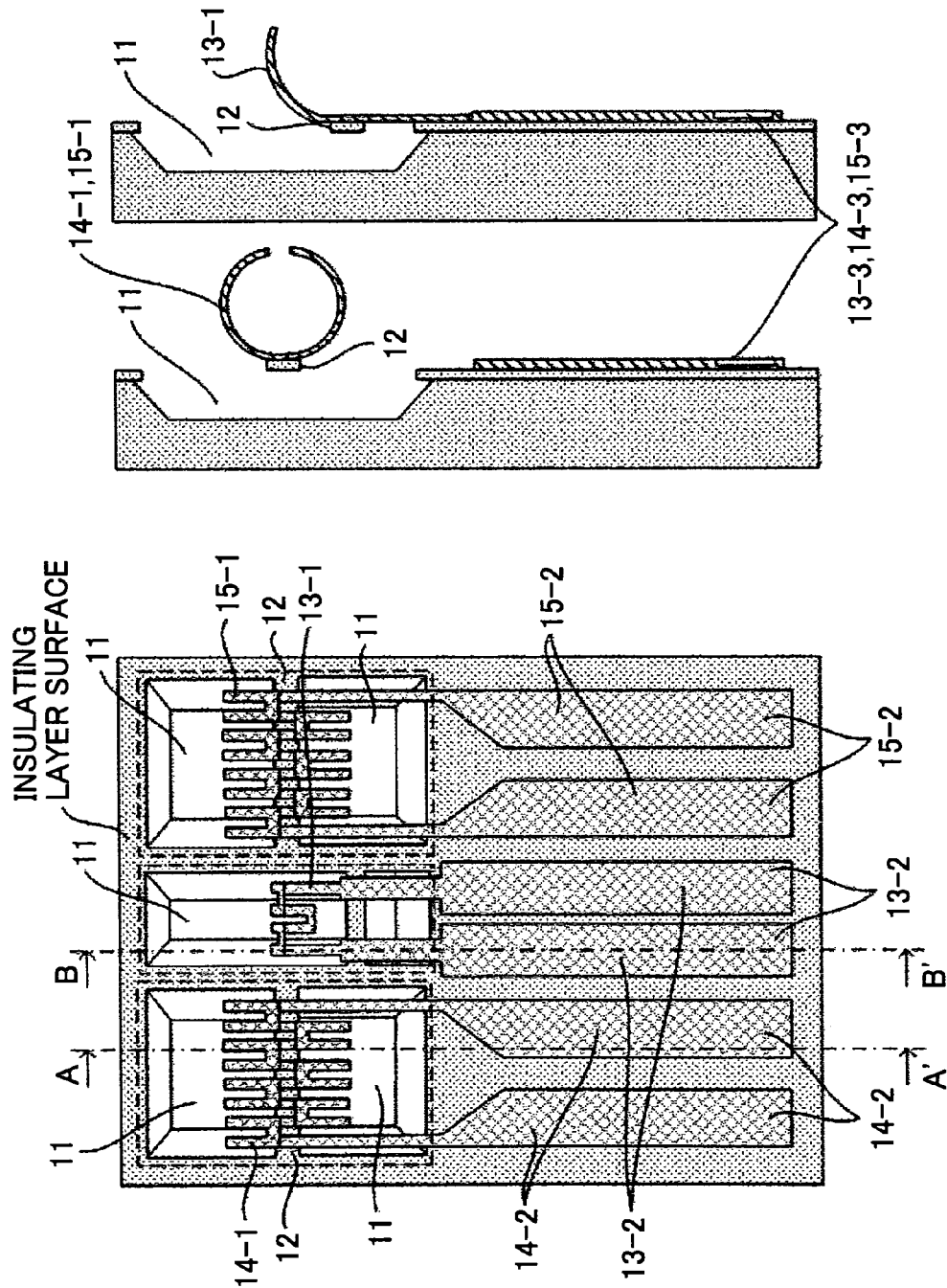

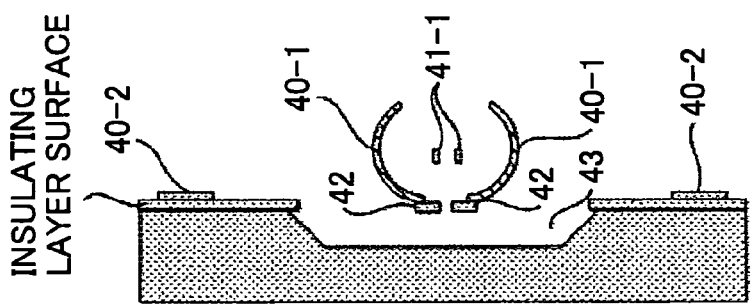
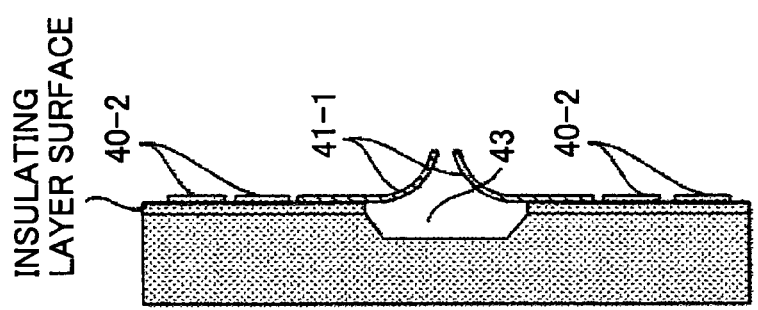
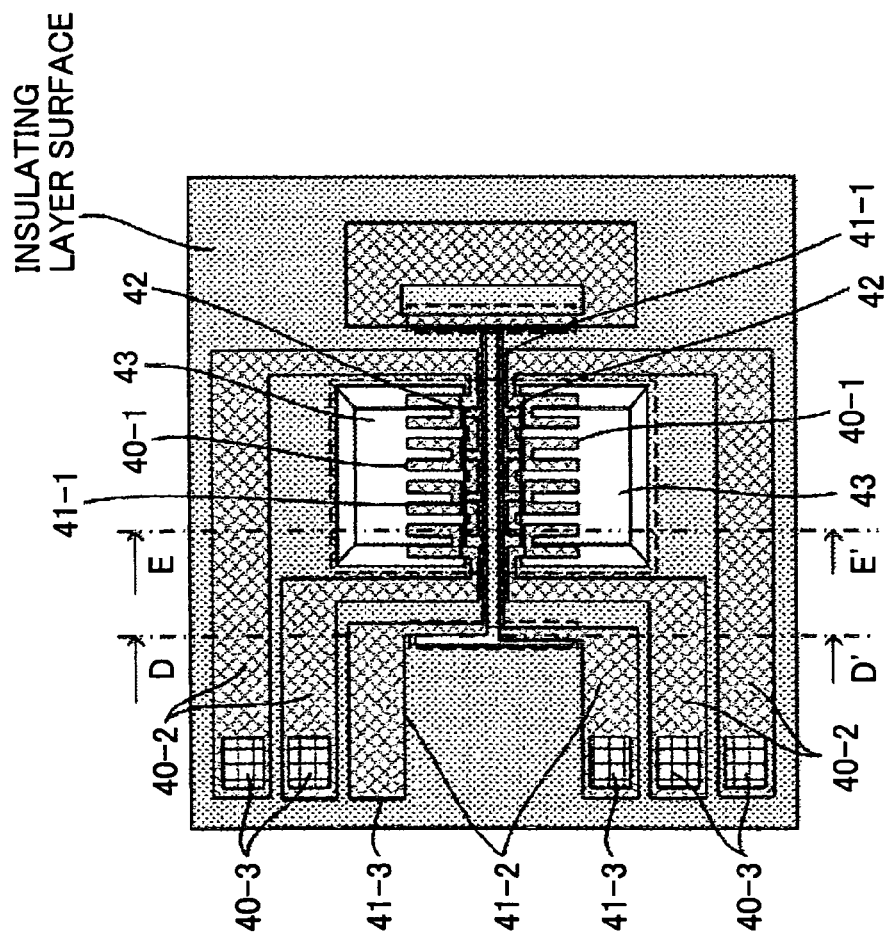

FIG.19A
FIG.19B
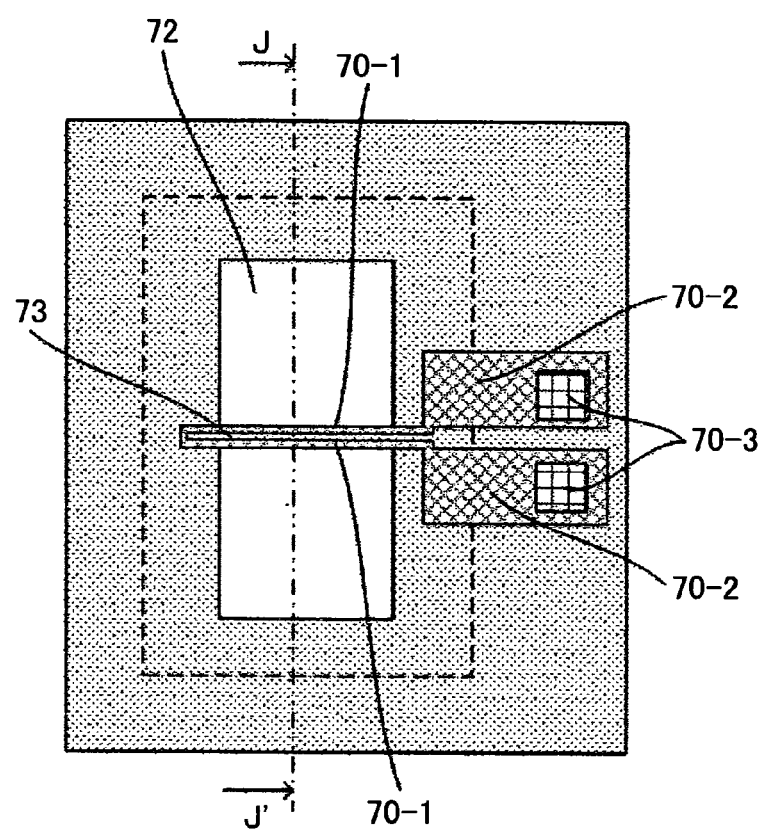
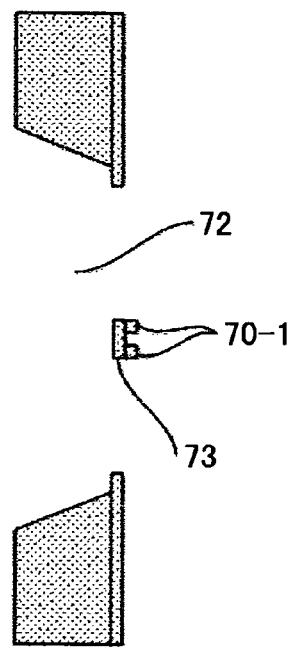

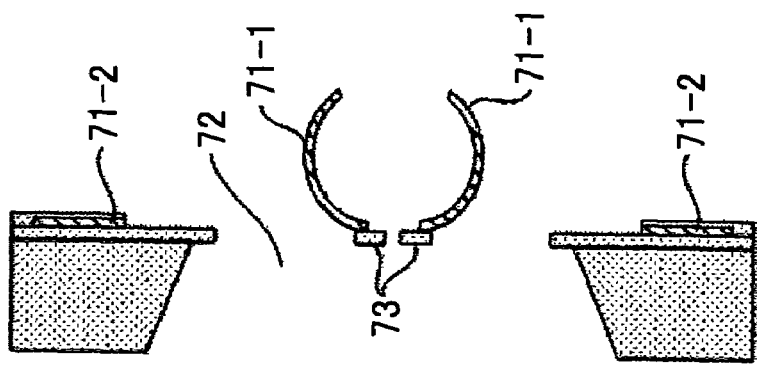
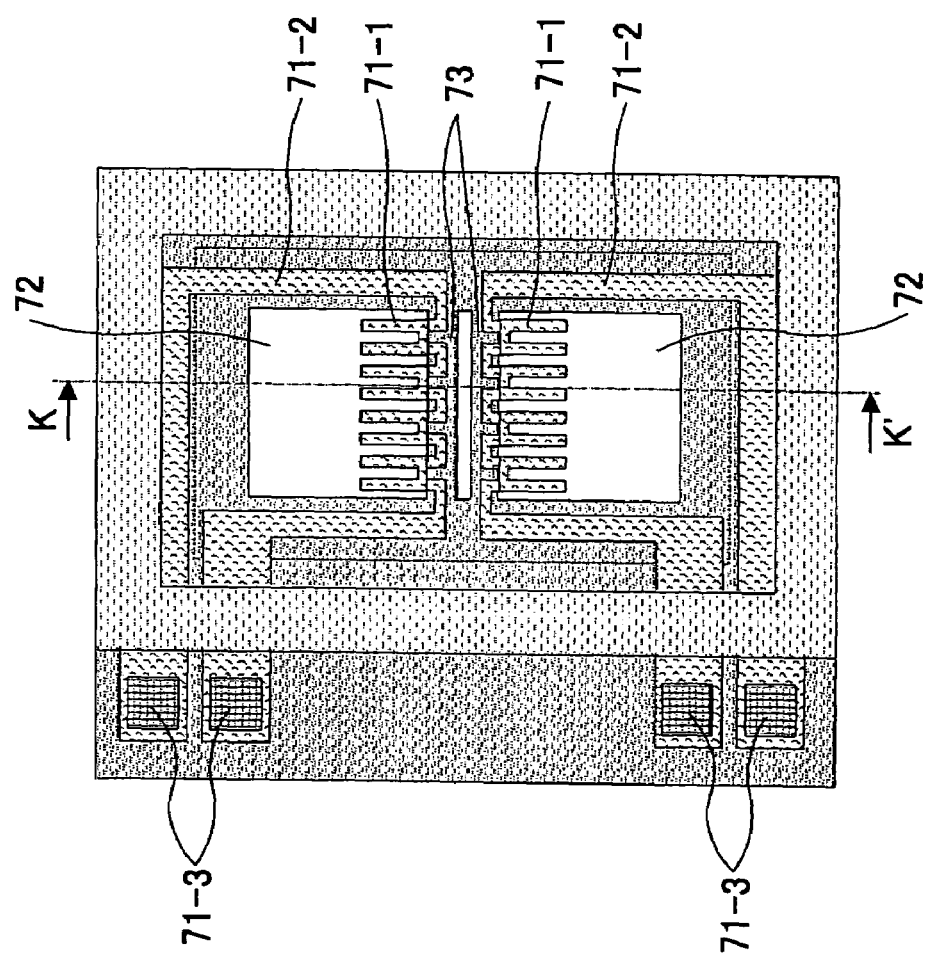
FIG.20A
FIG.20B

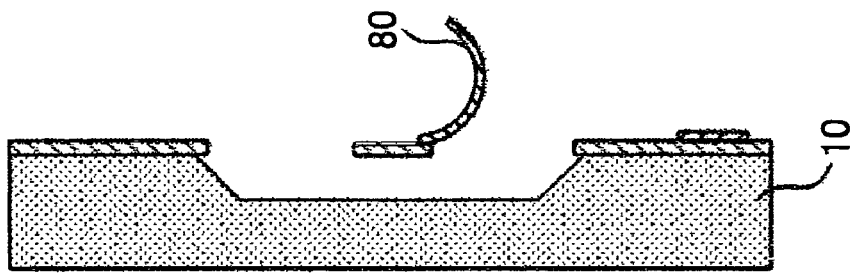
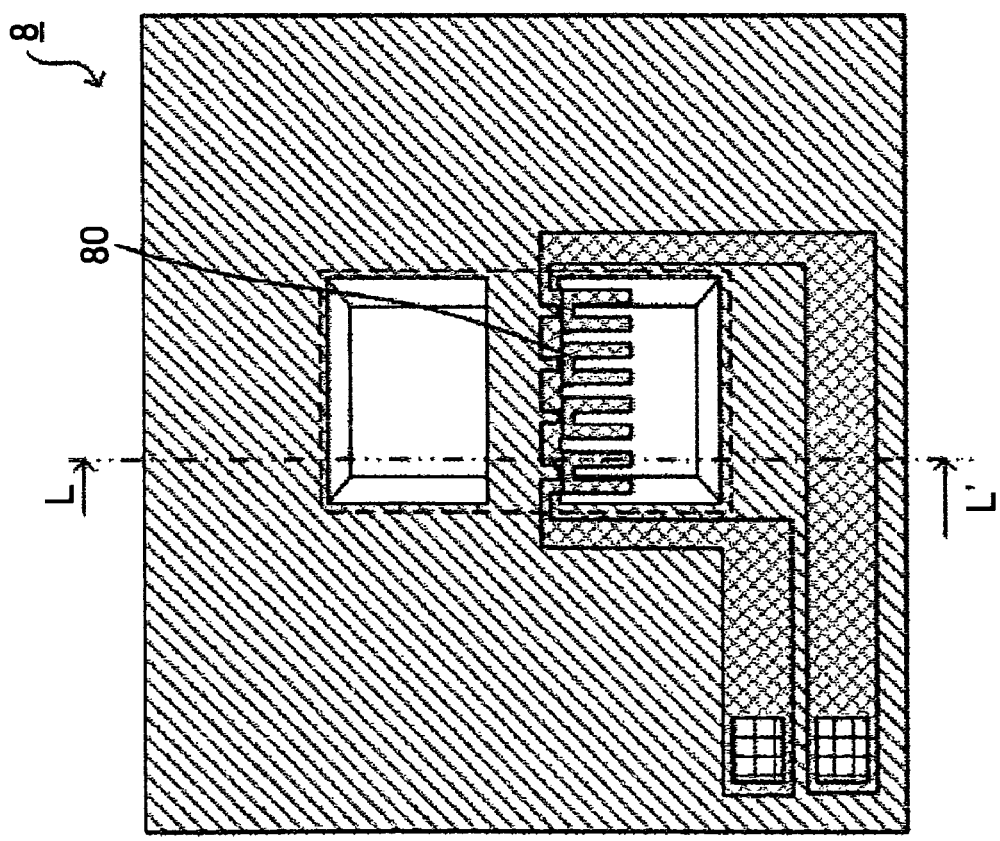

FIG.33B
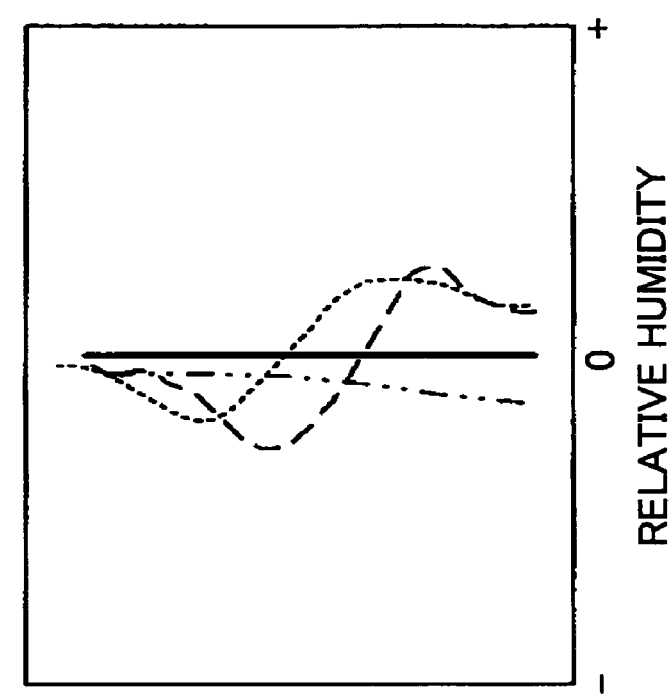
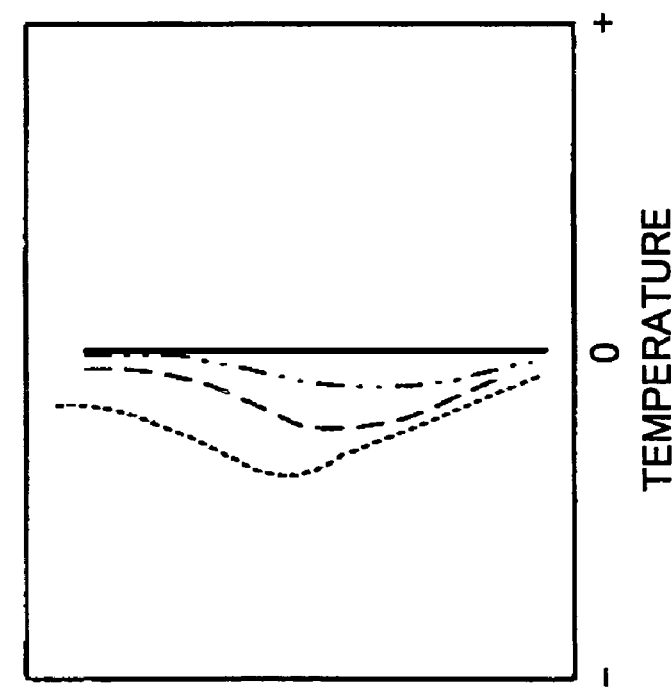

FIG.34A      FIG.34B
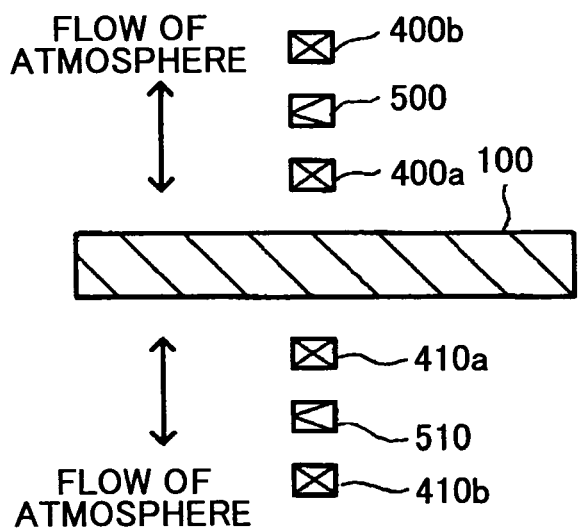
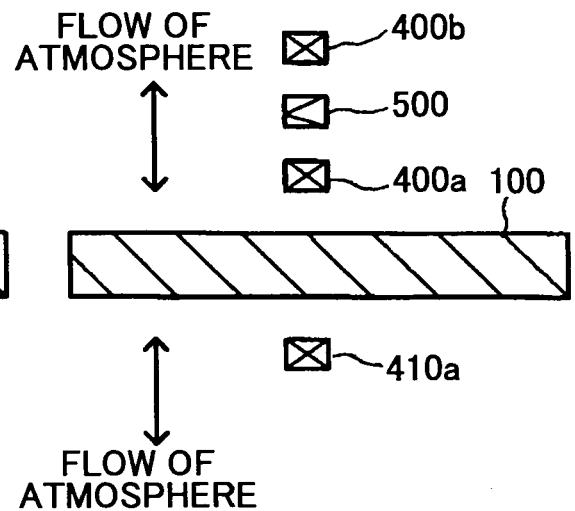
FIG.34C
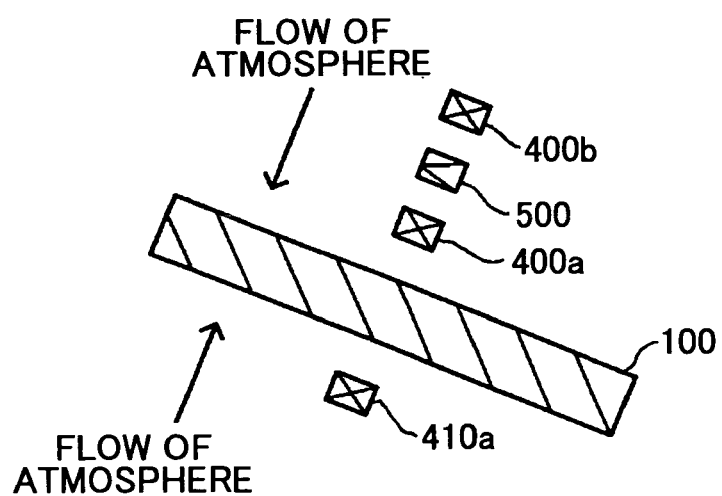

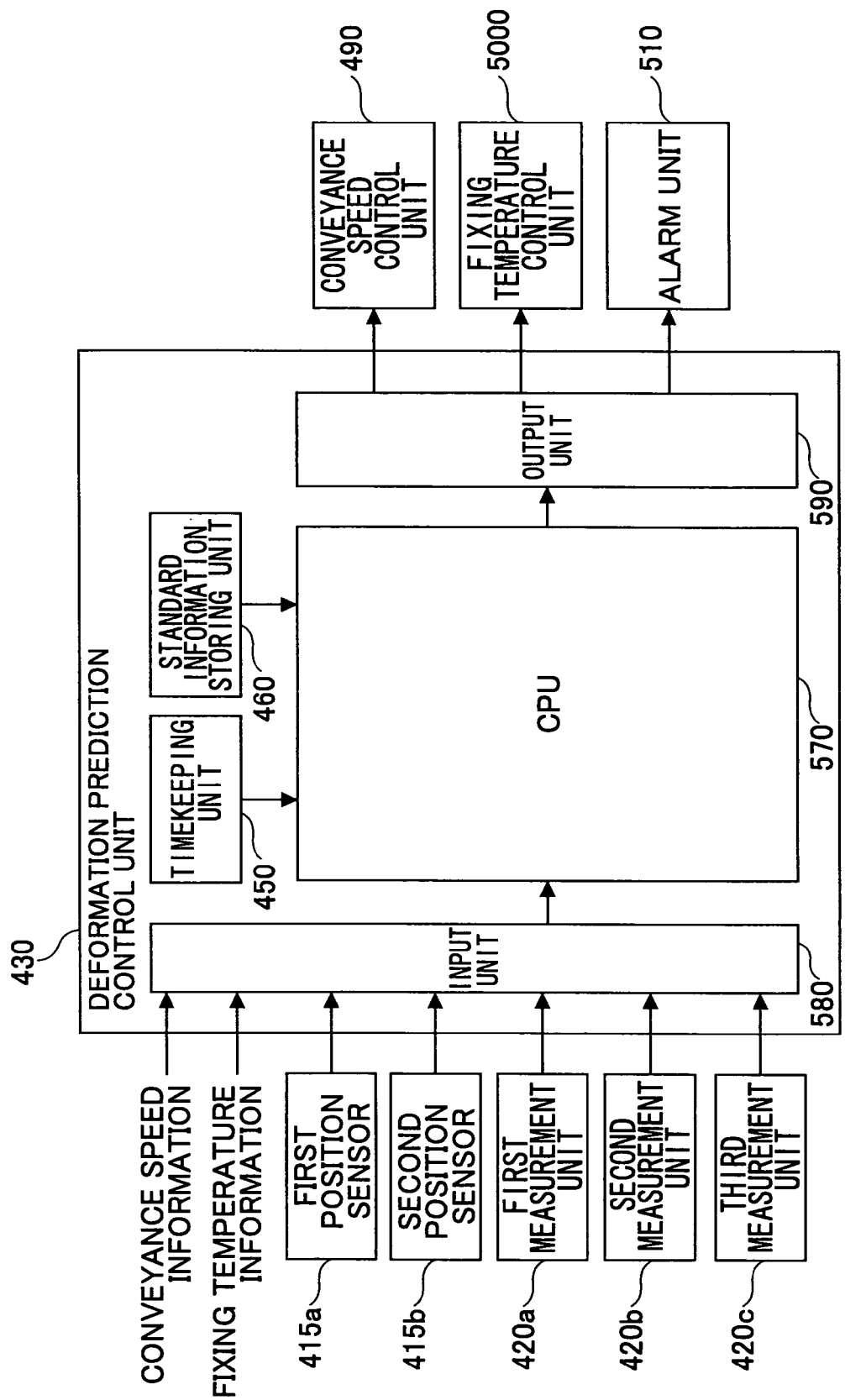

NON-CONTACT CONDENSATION DETECTING APPARATUS

BACKGROUND OF THE INVENTION

1. Field of the Invention

The present invention relates generally to non-contact condensation detecting methods and non-contact condensation detecting apparatuses, and more particularly to a non-contact condensation detecting method and a non-contact condensation detecting apparatus to easily detect dew condensation.

2. Description of the Related Art

Conventionally, there are methods of measuring the flow velocity and the flow rate of a fluid, and components and density of an atmosphere by detecting heat transported by the fluid and heat propagating in the atmosphere. A sensor serving as a detecting unit in a thermal flowmeter is configured as follows. A heater serving as a heat generation source is arranged on an upstream side of a flow of gas, and a temperature sensor is arranged on a downstream side of the flow of gas. The sensor measures the flow velocity and the flow rate based on the heat quantity (amount of temperature change) conveyed to the downstream side or the time it takes for the heat to reach the downstream side. Further, a sensor serving as a detecting unit in a hygrometer or a gaschromatograph measures humidity or components and density of gas based on heat quantity (amount of temperature change) propagated, or the time it takes for heat to be transported from a heater serving as a heat generation source in an atmosphere. The heat conductivity changes according to components or the density of the atmosphere. In the sensor serving as the detecting unit, the heat quantity of the heater serving as the heat generation source and the temperature sensor can be reduced, and the heater and the temperature sensor can be arranged extremely close to each other. With such a configuration, it is possible to accelerate thermal response, and detect rapid changes, a slight flow velocity/flow rate, minute amounts of components, or a minute level of density. The sensor is realized by microfabrication technology used for constructing integrated circuits. These types of sensors are conventionally called a flowsensor, a flow velocity sensor, a heat conductivity humidity sensor, or a heat conductivity gas sensor.

A flowsensor disclosed in Patent Document 1 includes a substrate having a through hole or a void, and a membrane heater section and a membrane detecting section bridged or cantilevered above the through hole or the void. The heater sections and the detecting sections are formed by laminating two or more layers along the flow direction of fluid to be measured, and interlayer spaces are provided. The spaces are formed by the thickness of layers, and are therefore formed highly accurately at minute intervals. Accordingly, the space distance between the membrane heater section and the membrane detecting section can be reduced so as to achieve fast responses, high precision, low fluid rates, and high efficiency.

A flowsensor disclosed in Patent Document 2 is realized by making a heater wire circular, making an isothermal line of a temperature distribution by the heat of the heater wire concentric, and also making temperature sensor wires at both sides of the heater wire concentric. Accordingly, whichever direction a fluid comes from, an isothermal line for each direction expands in the same shape with respect to the heater wire and the temperature sensor wire. Thus, detected values and detection sensitivity are not dependent on the direction of the fluid, so that the flow velocity or the flow rate can be detected regardless of the direction of the fluid. Specifically, a heater and a temperature sensor are arranged adjacent to each other on a plane. Gas is heated according to heat and the flow rate generated by the heater arranged at an upstream side. The heat quantity transported by the gas is captured (sensed) by the temperature sensor arranged at a downstream side, and is detected as a rise in the temperature. Moreover, the temperature sensor wire is shaped in accordance with the shape of the isothermal line of a temperature distribution of the heat from the heater wire. According to the configuration described in Patent Document 2, the temperature sensor wire is shaped in accordance with the shape of the isothermal line of a temperature distribution of the heat generated by the heater wire, and therefore, slight shifts of the isothermal line caused by slight changes in the flow rate or the flow velocity can be detected in substantially the entire area of the temperature sensor line. Thus, a highly sensitive flowsensor can be provided.

According to the Patent Documents 1, 2, it is understood that heat diffused in a three-dimensional space can be captured by making the temperature sensor three-dimensional, so as to surround the heater. Moreover, because it is necessary to detect the flow where influence from the surface of the substrate is minimal, the temperature sensor is to be arranged at a position distant from the substrate. The temperature sensor is to have a three-dimensional structure.

Patent Document 3 proposes a technology for fabricating three-dimensional components. According to the Patent Document 3, for low pressures of plasma gas, film stress in sputter-deposited coatings is compressive. As the pressure of the plasma gas increases, the film stress in a deposited sub-layer changes to a tensile stress. The intrinsic stress of many sputtered thin films depends on the ambient pressure at which the material is deposited. By varying the pressure during sputtering, films can be obtained that are compressively stressed near the substrate-film interface and tensile stressed at the film surface. A bottom gold layer forms the outer skin of a coil when released, and a release layer is removed by wet undercut etching. A possible etchant for a Si release layer includes KOH (wet processing). After removing a release window, each elastic member coils back on itself, due to an intrinsic stress profile of the elastic member. The foregoing techniques can also be used to manufacture a new type of high-Q variable capacitor (varicap). These varicaps use the same micro-spring technology described above, have the requisite capacitance values, and can be integrated on-chip. A varicap structure based on micro-springs allows both otherwise missing on-chip RF passive components, inductors and varicaps, to be fabricated using the same process technology. These micro-spring varicaps have the additional benefit of requiring lower bias voltages than parallel plate MEMS capacitors. By using a spring as the second electrode in a photolithographically patterned capacitor, and varying the voltage between a fixed plate and the spring, the capacitance of the structure varies.

Patent Document 1: Japanese Patent No. 3,049,122
Patent Document 2: Japanese Laid-Open Patent Application No. H11-118553
Patent Document 3: Japanese Publication of International Application No. 2003-533897

However, the following difficulties are faced according to Patent Document 1. Specifically, the heat from the heater at the upstream side diffuses three-dimensionally toward the downstream side, but the flow does not diffuse three-dimensionally because the flow path narrows. Therefore, the heat is easily transported to the temperature sensor. However, as the flow path is a solid object having higher heat conductivity than that of the fluid, excessive heat is conducted to the inner walls of the flow path due to the narrowed shape. As a result, the temperature sensor receives heat conduction components from the flow path, and a precise measurement cannot be performed. Moreover, because the heat quantity is large, heat accumulates in the substrate, and heat transferred from the substrate is added to the flow. This also affects the measurement of the temperature sensor located downstream. Further, as the units are arranged close to each other with high positional accuracy, adverse affects may be minimal. However, the positional relationship between the heater, the temperature sensor, and the substrate needs to be considered. Specifically, the distance between the heater and the temperature sensor is to be shorter than the distance between the heater and the substrate, and the heater and the temperature sensor need to be as far away from the substrate as much as possible.

According to Patent Document 2, the sensor is supposed to measure the flow in the middle of the flow; however, the sensor actually detects the flow at the surface of the substrate. More specifically, the sensor needs to detect the flow at a position least affected by the substrate surface. As the flow comes closer to the substrate surface, it flows less smoothly due to frictional resistance in the substrate surface. Thus, as the distance between the substrate becomes shorter, interference from the substrate increases. Accordingly, a slight flow rate cannot be measured. In addition, it is difficult to measure fluid of high viscosity, and at a temperature where the viscosity increases. In this configuration, the heater and the temperature sensor are arranged adjacent to each other on the plane. Gas is heated according to heat and the flow rate of the heat generated by the heater arranged at an upstream side. The heat quantity transported by the gas is captured by the temperature sensor arranged at a downstream side, and is detected as a rise in temperature. Moreover, the temperature sensor wire is shaped in accordance with the shape of the isothermal line of a temperature distribution of the heat of the heater wire. However, the heater and the temperature sensor are arranged adjacent to each other on the same plane, and the heat from the heater at the upstream side diffuses three-dimensionally toward the downstream side, and therefore, the temperature sensor can only capture a single plane component of the diffused heat components. As a result, the conveyance efficiency of heat and sensitivity is low, such that a low-noise, high resolution signal processing circuit is required. Also, in order to address the impact of a turbulence element, the temperature sensor needs to capture the three-dimensional isothermal line of three-dimensional heat diffusion.

Patent Document 3 discloses a three-dimensional coil formed on a chip. However, this structure is used as a contact point in variable capacitors and magnet coils, and is not intended for a heater and temperature sensor in a heat transportation mechanism. Due to the difference in functions, materials, shapes, and arrangements are different from those of a heat transportation mechanism. Thus, new configurations need to be added to realize a heater and temperature sensor in a heat transportation mechanism. To realize a sensor in a heat transportation mechanism for measuring the flow velocity or the flow rate of a fluid in a pipe and a space, the distance between the heater and the temperature sensor needs to be shorter than the distance between the heater and the substrate, and the heater and the temperature sensor need to be as far away from the substrate as possible. The temperature sensor needs to capture the three-dimensional isothermal line of three-dimensional heat diffusion as much as possible.

Conventionally, dew condensation has been a problem in various devices. Specifically, elements made of materials having high specific heat, and devices of large mass cannot adjust to rapid changes in the temperature/humidity in the surrounding environment. Therefore, dew condensation occurs on the surface, which causes malfunction of the device. Examples of such elements include optical recording media such as VTR head cylinders, hard disks, and optical disks; optical equipment such as lenses, light emitting devices, mirror reflectors, prisms, filters; optical devices including these optical equipment items; and components of image forming apparatuses such as photoconductive drums, polygon mirrors, and windows of automobiles and aircrafts. Dew condensation on the surfaces of these elements significantly affects functions of devices.

Moisture and gas adhering on recording sheets in electrophotographic image forming apparatuses significantly affect the image quality. Thus, it is required to accurately detect how the behavior of moisture adhering on the material surface is associated with the atmosphere, and control the behavior in an optimal manner. When a recording sheet dries as moisture in the sheet evaporates due to environmental changes, or when a recording sheet dries as moisture in the sheet undergoes rapid transpiration by receiving heat from a fixing unit, the recording sheet may deform by shrinking, curling, or creasing. Deformation needs to be prevented, because conveyance failures may occur while the sheet is being conveyed. In the fields of plants/animals and medicine, it is also necessary to detect water absorption phenomena or transpiration phenomena on surfaces of biologic objects, to examine the association with metabolism of biologic objects.

Japanese Laid-Open Patent Application No. 2002-310876 discloses a porous waterproof moisture permeable film that is porous on one side, allowing water vapor to permeate, but waterproof on the other side. If dew condensation water is formed on the porous side, the pores are blocked, and permeability to water vapor deteriorates. Accordingly, it is necessary to detect dew condensation.

Japanese Laid-Open Patent Application No. 2002-369885 discloses a power generating unit in which an electrocatalytic layer and a solid electrolyte membrane are combined. Gas transportation is less pronounced when dew condensation water is adhering, in a liquid state, on the solid electrolyte membrane. Gas transportation is more pronounced in a highly water-retentive state immediately before the condensation, and reaction efficiency of hydrogen and air is enhanced. Accordingly, it is necessary to detect the water retention rate of the solid electrolyte membrane.

In a cooling system, etc., disclosed in WO00/14522, in order to control cooling and dehumidifying operations in an optimal manner, it is necessary to detect the dew condensation on the surface of frozen materials near the surface of a heat exchanger in the cooling system side.

In a method of separating an organic solvent by distillation disclosed in Japanese Laid-Open Patent Application No. 2004-083385, the temperatures of aggregation and transpiration can be more precisely controlled by directly observing the gas behavior in the atmosphere, rather than detecting the temperature of the heat exchanger.

As described above, it is required in various fields to detect hydrophilia/hydrophoby on surfaces by quickly detecting aggregation and transpiration behaviors with high sensitivity, and detecting the differences in absorption of gas vapor molecules onto various surfaces.

There are conventional technologies for detecting dew condensation. Patent Document 4 discloses a condensation detection device. A VTR rotatable cylinder device has large heat capacity and dew condensation is thus likely to occur. Due to dew condensation, magnetic tape may adhere to the rotatable cylinder and get tangled. To prevent this problem, the condensation detection device determines whether the atmosphere is shifting into a supersaturation state. Specifically, the condensation detection device measures the surface temperature of the rotatable cylinder and the temperature and the humidity of the atmosphere near the rotatable cylinder, and then refers to data of the moisture amount in the air (psychrometric diagram), to make the determination.

Patent Document 5 discloses a method for measuring dew point or gas concentration, and an ice accretion predicting device. Dew condensation is detected based on a dew point obtained from the relative humidity of the atmosphere and the temperature of the subject of measurement. This method employs a relative humidity sensor employing a dielectric polymer, which responds more quickly to dew condensation than a mirror cooling method. An electrostatic capacity type, quick-response relative humidity sensor employing a dielectric polymer is cooled externally when the relative humidity is low. When the temperature is near the dew point, where the relative humidity rises, the relative humidity sensor is under a highly humid environment and is likely to maintain moisture, which makes it difficult to predict ice accretion. Thus, the relative humidity sensor is heated externally so as to change the temperature of the relative humidity sensor, thereby enhancing measurement precision.

Patent Document 6 discloses a dew condensation predicting device. Dew condensation is predicted by thermally binding a thermoelectric element to a dew condensation sensor to lower the temperature of the dew condensation sensor lower than the atmospheric temperature. In performing this operation, if water droplets are retained on the dew condensation sensor for a long time, the material of the sensor deteriorates. Thus, the dew condensation sensor is heated with the thermoelectric element to remove the dew condensation water from the dew condensation sensor.

Patent Document 7 discloses a sensor for predicting change of phase and a device for preventing frosting and dewing. Specifically, a dew condensation sensor is mounted onto a detection subject through a Peltier element. Heat is prevented from being transferred to/from the detection subject, so that the temperature of the dew condensation sensor is constantly lower by a fixed value than the surface of the detection subject. Dew condensation thus occurs faster on the dew condensation sensor than on the detection subject, so that frosting and dewing can be predicted.

Patent Document 8 discloses a temperature sensor for vehicles. The casing of a sensor for detecting the temperatures in various areas in a vehicle and the windshield of the vehicle are connected by a cup-shaped heat bonding member made of a heat conductive material. Incident infrared rays from the various areas are detected by a sensor element. When the temperature distributions at the various areas enter a predetermined range, the sensor determines that dew condensation has occurred on the windshield.

Patent Document 9 discloses a non-contact temperature measuring apparatus that utilizes the fact that heat flow between a reference object and an external object is proportional to the temperature of the external object. The non-contact temperature measuring apparatus detects, using a temperature sensor, temperatures of a first reference object and a second reference object that are spaced apart from each other by a certain distance along a moving continuous body. Accordingly, the temperature of the moving body is calculated.

Patent Document 10 discloses a technology for preventing a conveyance failure of a recording sheet in an electrophotographic image forming apparatus, caused by curling or creasing of the recording sheet while being conveyed. Specifically, an infrared ray moisture meter is used to detect the amount of moisture included in various parts of a recording sheet. According to the detected amount of moisture, the amount of air to be blown against various parts of the recording sheet is adjusted. This prevents the recording sheet from curling partially due to uneven amounts of moisture. In a technology disclosed in Patent Document 11, the amount of moisture included in a recording sheet is detected based on variations in transmission of a certain wavelength of infrared light reflected from the recording sheet. Based on the detected amount of moisture, the fixing temperature of a fixing device and roller pressure in a paper conveying path are controlled. In a technology disclosed in Patent Document 12, moisture included in a recording sheet is detected by using a moisture meter equipped for measuring the absorption of microwaves. The extent to which the recording sheet will curl is predicted based on the detected moisture amount and the type of the recording sheet, i.e. the strength (body) of the recording sheet. According to the prediction, curling of the recording sheet is corrected.

Patent Document 4: Japanese Laid-Open Patent Application No. H3-78648

Patent Document 5: Japanese Patent No. 2801156

Patent Document 6: Japanese Laid-Open Patent Application No. H1-127942

Patent Document 7: Japanese Laid-Open Patent Application No. H4-128643

Patent Document 8: Japanese Laid-Open Patent Application No. 2004-66927

Patent Document 9: Japanese Patent No. 3292523

Patent Document 10: Japanese Laid-Open Patent Application No. 2005-170525

Patent Document 11: Japanese Laid-Open Patent Application No. 2001-301273

Patent Document 12: Japanese Patent No. 2902130

In the condensation detection device disclosed in Patent Document 4, the dew condensation sensor needs to be attached to the rotatable cylinder of the VTR rotatable cylinder, in accordance with dew condensation properties of the rotating cylinder. If the dew condensation sensor is attached like a generic sensor, it cannot detect dew condensation. Moreover, there are restrictions in attaching the dew condensation sensor to the rotatable cylinder, because of functions of a magnetic head and electrical signals received by the rotatable member.

According to the method of dew condensation detection disclosed in Patent Document 5, or the devices disclosed in Patent Documents 6, 7, the sensor is heated externally, or the sensor is cooled to a temperature lower than the atmosphere. Accordingly, the temperature of the atmosphere measured by the sensor is different from that of the atmosphere of the subject of dew condensation. As a result, precision of detection deteriorates, because the sensor detects a different temperature from that of the atmosphere of the subject of condensation.

In the method of estimating dew condensation disclosed in Patent Document 8, the sensor needs to be mounted onto the surface that is the subject of dew condensation, and thus cannot be used generically. The non-contact temperature measuring apparatus disclosed in Patent Document 9 is capable of measuring the temperature of a remote object in a non-contact manner by measuring the temperature gradient of gas; however, gas-liquid phase changes cannot be measured by this method.

Each of the dew condensation sensors described above detects whether dew condensation has occurred on itself. However, these dew condensation sensors cannot detect whether dew condensation has occurred on the actual subject.

The dew condensation sensors described above require special means in thermal structures to accommodate properties of dew condensation on the subject. Therefore, the dew condensation sensors cannot detect dew condensation of the subject by simply being attached to the subject, or being disposed near the subject.

The dew condensation sensors described above have dew condensation prediction functions. However, each of these sensors operates as a system using a dew condensation prediction algorithm obtained by adding a detected temperature of a specific location in the device. Accordingly, these sensors can only be applied to specific devices, and cannot be used universally.

By using an optical means such as a mirror cooling type dew point meter to measure dew condensation of a subject object from a remote location, only a mirror surface can be measured. Accordingly, this type of means cannot be generically used to measure any type of surface. A conceivable method is to detect a dew condensation phenomenon by combining a humidity sensor with an infrared thermometer. However, the emissivity differs according to surface conditions, and therefore, an accurate temperature cannot be measured. The temperature can be measured only for the portions of the surface where emissivity is known, and it is not certain whether the humidity of the surface of the subject object is detected.

In an image forming apparatus, deformation of a recording sheet, such as curling, is caused when the recording sheet dries rapidly. Specifically, the direct cause of the deformation is the speed of drying. The drying speed of a recording sheet depends on the speed at which moisture in the recording sheet is reduced by transpiration. The transpiration behavior reflects the quality and structure of the recording sheet, and the strength of the recording sheet determined by the quality and structure thereof. Thus, as described in Patent Documents 10, 12, it is difficult to predict deformation such as curling of a recording sheet with high precision, even by detecting the amount of moisture included in the recording sheet.

SUMMARY OF THE INVENTION

Accordingly, the present invention may provide a detector element, a non-contact condensation detecting method, and a non-contact condensation detecting apparatus in which the above-described disadvantage is eliminated.

A preferred embodiment of the present invention provides a detector element that can capture (detect) three-dimensional heat diffusion with a three-dimensional temperature sensor, capture a three-dimensional isothermal line with the temperature sensor, make the distance between a heating unit and the temperature sensor shorter than the distance between the heater and a substrate, and engage in a phenomenon in a three-dimensional space including heat elements.

A preferred embodiment of the present invention provides a non-contact condensation detecting method and a non-contact condensation detecting apparatus that can detect gas aggregation and transpiration on the surface of a measurement subject from a remote location in a non-contact manner based on physical changes in the atmosphere that is a continuous space in contact with the measurement subject without mounting a dew condensation sensor directly onto the subject object, and quickly detect the state of dew condensation on the surface of the subject object so as to accurately predict dew condensation on the surface of the subject object.

A preferred embodiment of the present invention provides a recording sheet deformation preventing method and an image forming apparatus that can detect, in real time, the transpiration speed of moisture included in a recording sheet on which an image is to be formed, predict with high precision whether the recording sheet will deform by curling, etc., due to rapid drying, and prevent deformation of the recording sheet, by employing the non-contact condensation detecting apparatus according to the present invention.

An embodiment of the present invention provides a detector element including a substrate including one of a through hole and a void; a heating unit including a heat generating electrode bridged across said one of the through hole and the void, the heat generating electrode being warped, cantilevered, and standing up in space; and a temperature sensor including a temperature sensor electrode provided above said one of the through hole and the void, the temperature sensor electrode being warped, cantilevered, and standing up in space, wherein the temperature sensor measures heat quantity transported from the heating unit.

An embodiment of the present invention provides a non-contact condensation detecting method including the steps of measuring distribution of an atmosphere surrounding an object surface with respect to the object surface and a transportation state of the atmosphere, by using at least one element selected among temperature, humidity, a direction or velocity of flow, pressure, and composition of gas in the atmosphere; and detecting a behavior of the gas adhering and aggregating onto the object surface, and a behavior of aggregated liquid transpiring from the object surface, based on the distribution and the transportation state measured at the measuring step.

An embodiment of the present invention provides a non-contact condensation detecting apparatus, including a measurement unit disposed at least at two locations, near an object surface and distant from the object surface, the measurement unit including a temperature/humidity sensor configured to measure temperature and humidity of gas of an atmosphere surrounding the object surface, and a flowsensor configured to measure one of a flow direction and flow velocity of the gas of the atmosphere surrounding the object surface; and a processing unit configured to determine distribution of the atmosphere with respect to the object surface and a transportation state of the atmosphere based on measurement results of the temperature/humidity sensor and the flowsensor, and detect a behavior of the gas adhering and aggregating onto the object surface, and a behavior of aggregated liquid undergoing transpiration from the object surface.

According to one embodiment of the present invention, three-dimensional heat diffusion can be captured with a three-dimensional temperature sensor, a three-dimensional isothermal line can thereby be captured with the temperature sensor, and the distance between a heating unit and the temperature sensor can be made shorter than the distance between the heater and a substrate.

According to one embodiment of the present invention, it is possible to detect states of dew condensation on the object surface in a non-contact manner, accurately predict dew condensation and transpiration on the object surface, and efficiently prevent dew condensation.

BRIEF DESCRIPTION OF THE DRAWINGS

Other objects, features and advantages of the present invention will become more apparent from the following detailed description when read in conjunction with the accompanying drawings, in which:

FIGS. 5A, 5B, 5C are diagrams for describing fabrication steps of the detector element according to the first embodiment;

FIGS. 12A, 12B, 12C are diagrams for describing fabrication steps of the detector element according to the fourth embodiment;

FIGS. 19A, 19B are schematic diagrams of a heating unit of a detector element according to a seventh embodiment of the present invention;

FIGS. 20A, 20B are schematic diagrams of a temperature sensor of the detector element according to the seventh embodiment;

FIGS. 23A, 23B are schematic diagrams of a detector element according to the eighth embodiment of the present invention;

FIGS. 33A, 33B are distribution charts of the temperature and the humidity of the atmosphere at the upper surface and the lower surface of the object;

FIGS. 34A, 34B, 34C are diagrams of a fourth example of a measurement unit;

FIG. 54 is a block diagram of another deformation prediction control unit.

DETAILED DESCRIPTION OF THE PREFERRED EMBODIMENTS

A description is given, with reference to the accompanying drawings, of an embodiment of the present invention.

Figure 1:
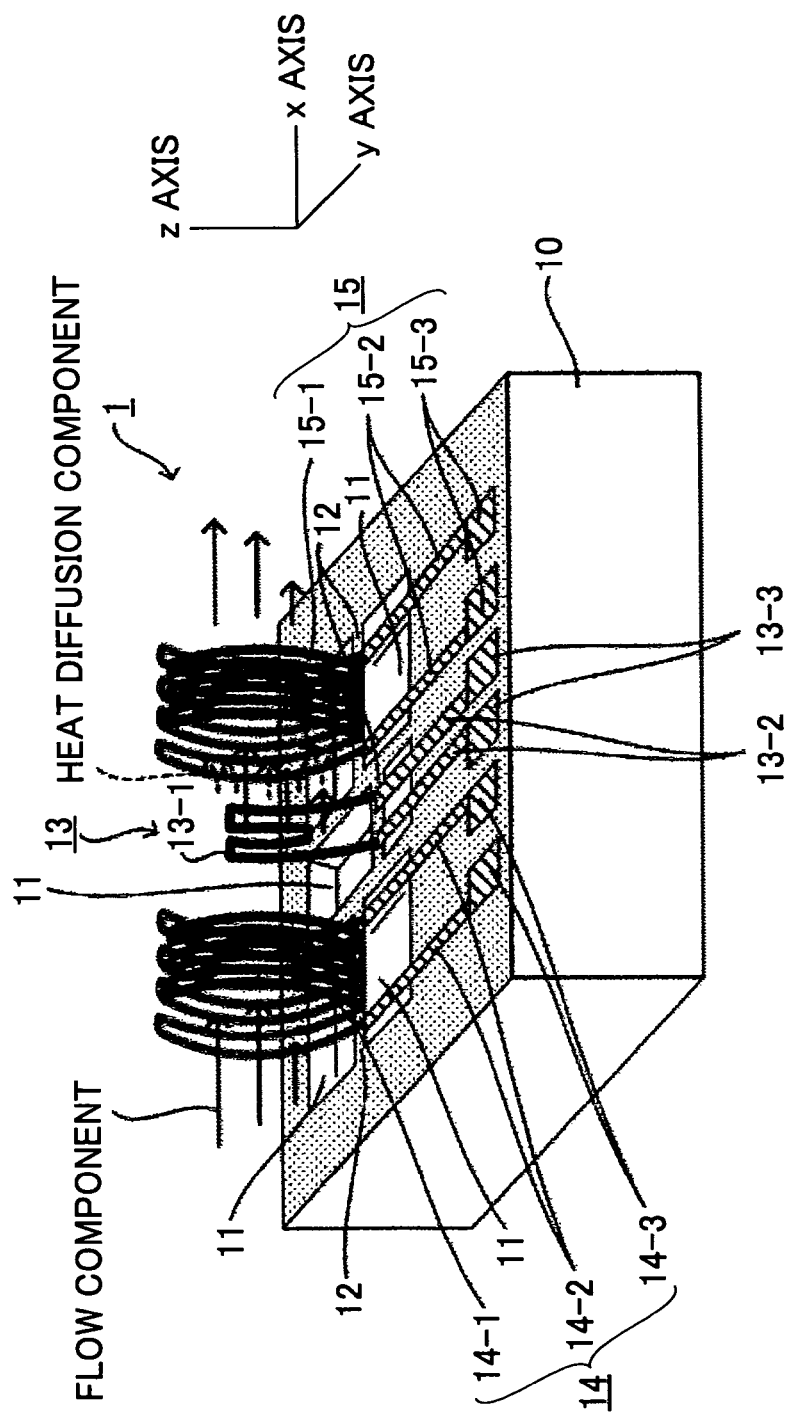
FIG. 1 is a perspective view of a detector element according to a first embodiment of the present invention.
Figure 2:
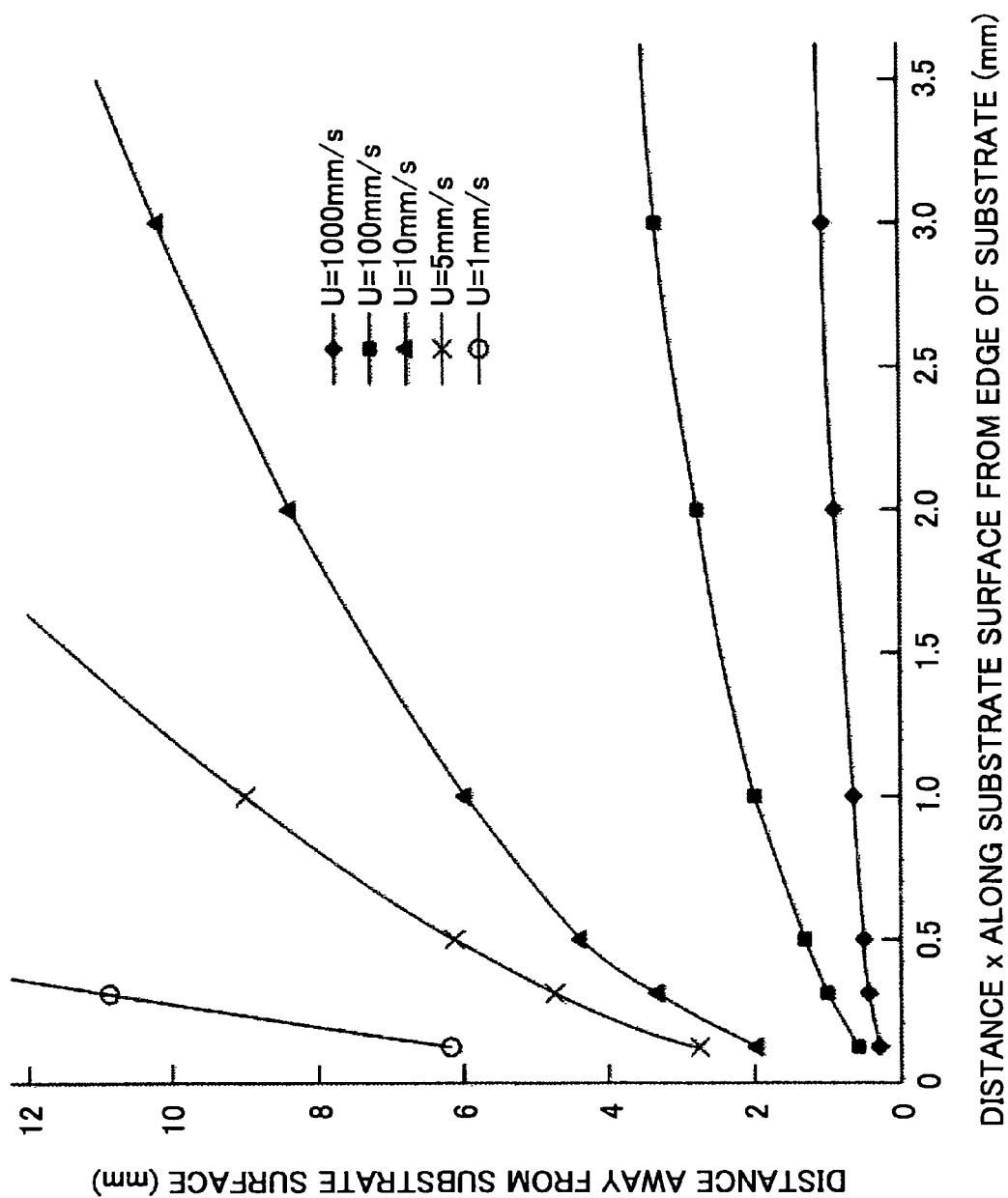
FIG. 2 is a graph for describing flow velocity measurement properties of air by the distance along the substrate surface from the edge of the substrate and the distance away from the substrate surface.

FIG. 1 is a perspective view of a configuration of a detector element 1 according to a first embodiment of the present invention. The detector element 1 includes a substrate 10, bridges 12 disposed across voids 11 in the substrate 10, a heating unit 13, and two temperature sensors 14, 15 disposed on the bridges 12, respectively. The two temperature sensors 14, 15 are disposed in parallel one on each side of the heating unit 13. The temperature sensors 14, 15 include temperature sensor electrodes 14-1, 15-1, respectively, which are shaped like the curved surface of a pipe, and are arranged facing each other. The heating unit 13 includes a heat generating electrode 13-1 connected to power supply leads 13-2. An electrode pad 13-3 is connected to each power supply lead 13-2. The heating unit 13 generates Joule heat using power supplied from the electrode pads 13-3. Further, detection leads 14-2, 15-2 are connected to the ends of the temperature sensor electrodes 14-1, 15-1 of the temperature sensors 14, 15, respectively. Electrode pads 14-3, 15-3 are connected to the detection leads 14-2, 15-2, respectively. The temperature sensors 14, 15 have temperature dependent properties, according to heat transferred from a neighboring space. Heat from the heating unit 13 located upstream in a flow along the x axis is diffused in the space according to the flow velocity. The heat is captured inside the pipe-shaped curved surfaces of the temperature sensors 14, 15. The flow velocity and the flow rate of the fluid flowing inside the pipe-shaped temperature sensor electrodes 14-1, 15-1 of the temperature sensors 14, 15 are measured. The heat diffuses not only along the flow in the x axis direction, but also in a three-dimensional space. In the flow along the x axis, the temperature sensors 14, 15 are arranged in a three-dimensional space with respect to the heating unit 13. Accordingly, the temperature sensors 14, 15 capture the heat diffused from the heating unit 13 in a three-dimensional space, and therefore, their heat transfer efficiency is high. Due to friction, the flow velocity of the fluid near the surface of the substrate 10 is lower than the flow velocity of the fluid distant from the surface of the substrate 10. However, the heating unit 13 and the temperature sensors 14, 15 are standing up on the substrate 10, rising up on the surface of the substrate 10. With this configuration, even a slight flow velocity can be measured, unlike a case where the heating unit 13 and the temperature sensors 14, 15 are disposed flat on the surface of the substrate 10. Moreover, even at high velocity, the captured fluid is less likely to flow away from the surface and cause turbulence. The advantages of measuring a slight flow velocity at a position distant from the surface of the substrate 10 are described below. FIG. 2 is a graph for describing flow velocity measurement properties of air by the distance along the substrate surface from the edge of the substrate and the distance away from the substrate surface. As shown in FIG. 2, it is necessary to measure the flow velocity of air at a position distant from the surface of the substrate 10. Specifically, at a distance less than the thickness of the boundary layer, the property values of the fluid and dependence on the substrate structure intricately affect each other. Accordingly, the measured value needs to be corrected in order to obtain the actual flow velocity, which entails indeterminacy (may be indeterminate). Thus, in a case of measuring a slight flow velocity, it is even more advantageous to measure the flow velocity at a position distant from the surface of the substrate 10. According to Stokes' law, the thickness of the boundary layer at which the laminar flow velocity receives friction resistance along a flat plane surface can be obtained with the following formula:

$$\delta \approx 5*(\nu x/U)^{1/2}$$

where $\nu=\eta/\rho$, $\eta$: kinematic viscosity coefficient, $\rho$:density, x:distance from edge, U: flow velocity.

The temperature sensor 14, which is located upstream of the heating unit 13, is used for capturing the first temperature information of the fluid using temperature properties of temperature-sensitive material. Alternatively, the temperature sensor 14 is used for measuring the temperature information when the flow of the fluid is reversed. The temperature sensor 14 can capture diffused heat from the heating unit 13 in a three-dimensional space. If the temperature sensor 14 were to be disposed flat on the surface of the substrate 10, the sensitivity would be affected by a change in the angle with respect to the flow, and therefore, maximum sensitivity could only be obtained in a single direction. However, because the temperature sensors 14, 15 according to the present embodiment are arranged in a three dimensional manner with respect to the heating unit 13, the temperature sensors 14, 15 can accommodate changes in the angle of the flow. Accordingly, even if the angle of the flow along the x axis changes, because the flow is captured in a three-dimensional space, the position of the sensor can be easily adjusted with respect to the axis of the flow. Moreover, the vertical posture of the substrate significantly affects the heat flow. Because heated gas flows upward, if the substrate were facing downward, heat would accumulate in the voids. If the substrate is facing upwards, heat does not accumulate in the voids. However, because the heating unit 13 and the temperature sensors 14, 15 are standing up on the substrate 10, rising up on the surface of the substrate 10, measurement of temperature is unaffected by the posture of the substrate 10. Accordingly, the detector element 1 can be installed in various locations.

Figure 3:
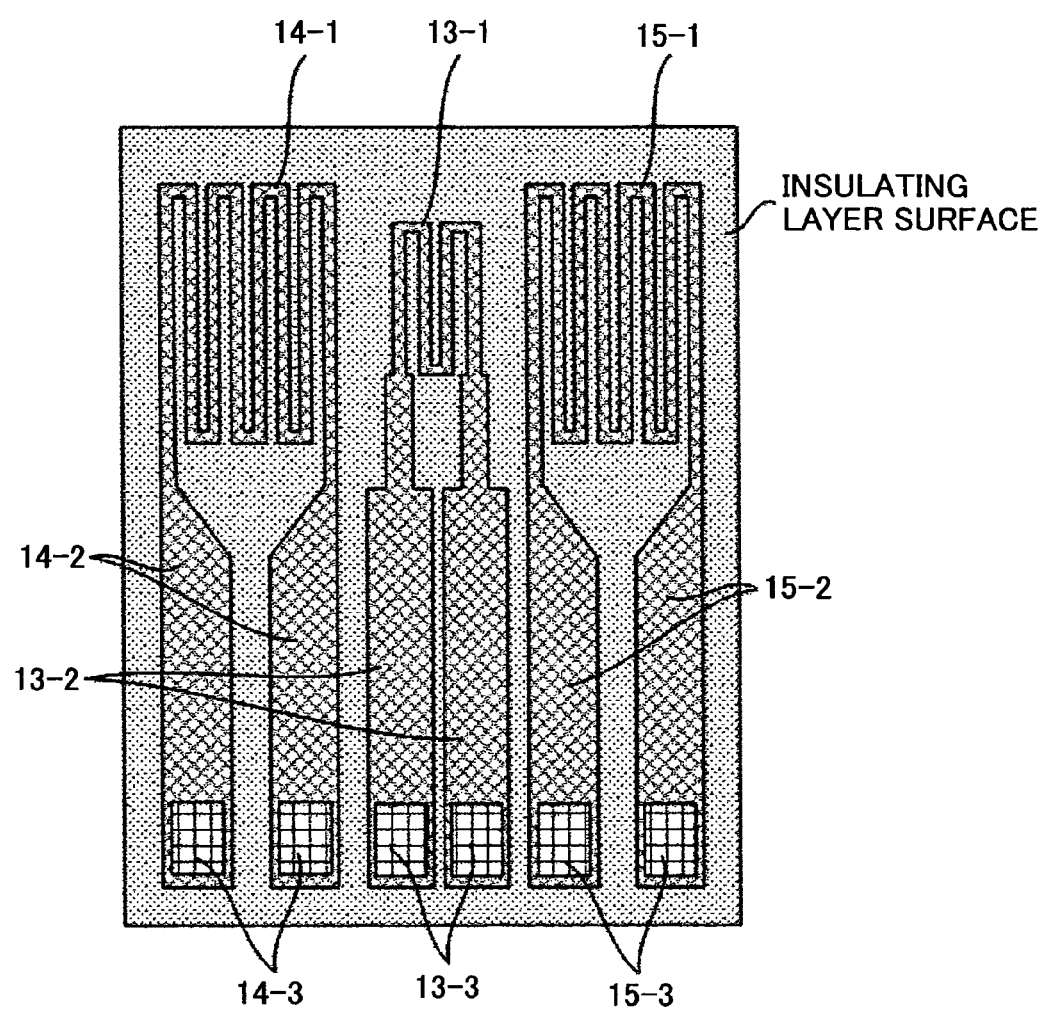
FIG. 3 is a diagram for describing fabrication steps of the detector element according to the first embodiment.
Figure 4B:
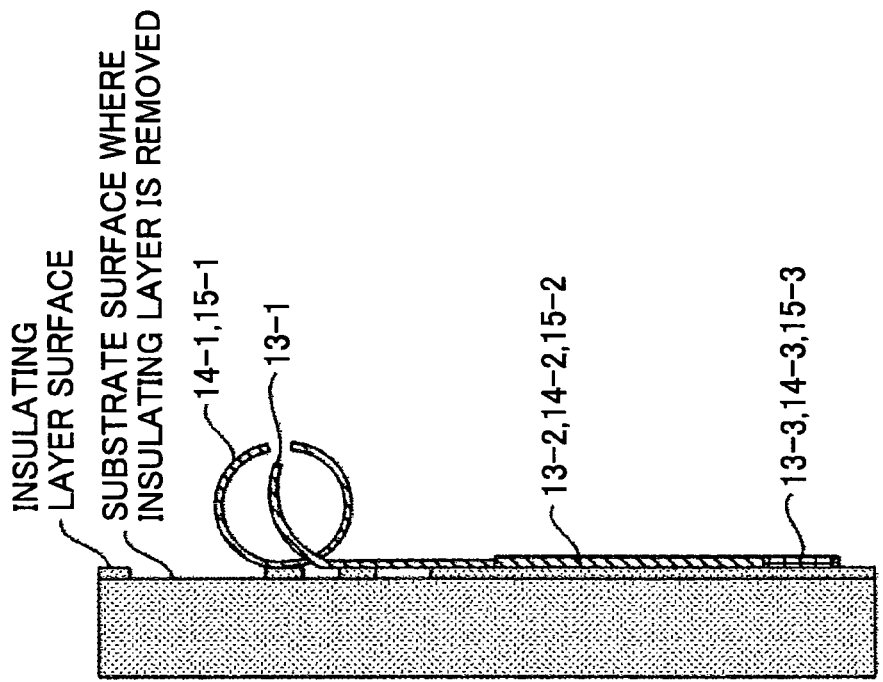
FIGS. 4A, 4B are diagrams for describing fabrication steps of the detector element according to the first embodiment.
Figure 4A:
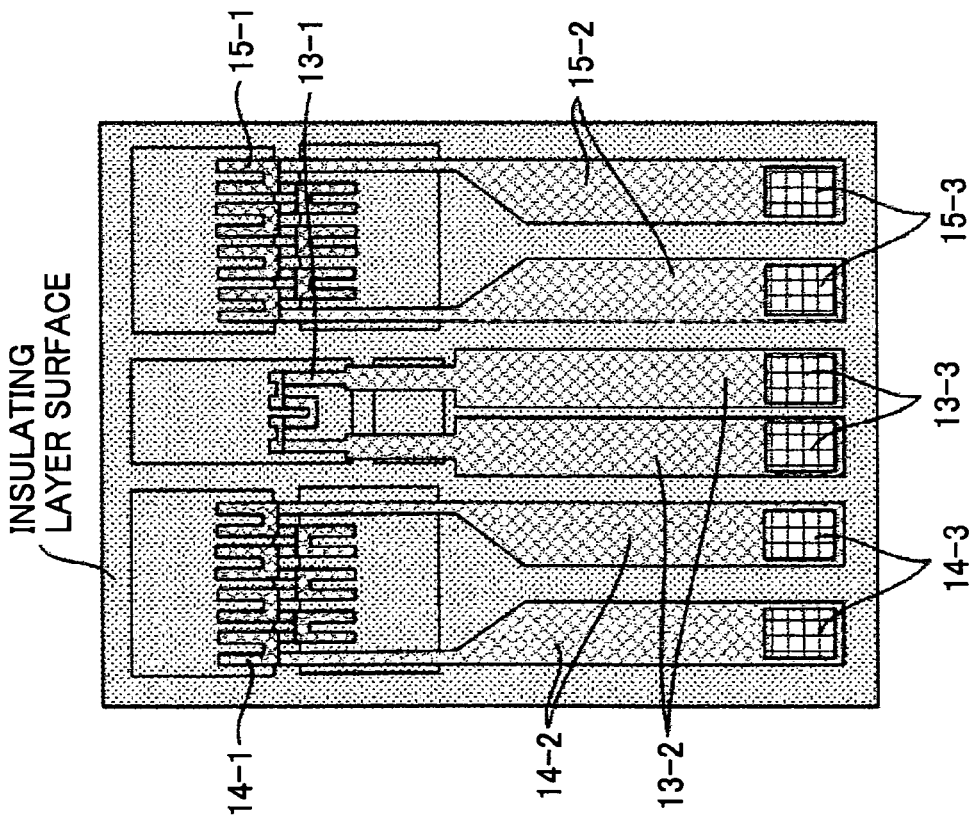

Although the heating unit 13 and the temperature sensors 14, 15 have three-dimensional structures, they can be fabricated by plane machining. The fabricating method is described with reference to FIGS. 3 through 5. FIGS. 3, 4A, 5A are plan views, FIG. 4B is a side view, FIG. 5B is a cross-sectional view taken along line A-A' of FIG. 5A, and FIG. 5C is a cross-sectional view taken along line B-B' of FIG. 5A. Elements corresponding to those in FIG. 1 are denoted by the same reference numbers.

As shown in FIG. 3, patterns made of conductive material films are formed on the substrate 10 for the heat generating electrode 13-1 and the power supply leads 13-2 of the heating unit 13, and the temperature sensor electrodes 14-1, 15-1, the detection leads 14-2, 15-2, and the electrode pads 14-3, 15-3 of the temperature sensors 14, 15, respectively. A metal material having a high resistance temperature coefficient such as Pt, W is used for the heating unit 13 and the temperature sensors 14, 15. The power supply leads 13-2 and the detection leads 14-2, 15-2 are formed with the same material, and can therefore be formed at the same time, thus enhancing convenience. The power supply leads 13-2 and the detection leads 14-2, 15-2 must have low electric resistance values so as not to generate heat. Accordingly, the power supply leads 13-2 and the detection leads 14-2, 15-2 are made wider in the direction of current flow, and arranged on the substrate 10 so as to increase heat capacity. The temperature sensors 14, 15 can be formed of a thermoelectric material having a Seebeck effect. In the case of using such a thermoelectric material, the cold junction is arranged on the substrate 10 in an area where there is no void.

An insulating layer on the substrate 10 shown in FIG. 4A is removed by etching in the area of the heat generating electrode 13-1 of the heating unit 13 and the temperature sensor electrodes 14-1, 15-1 of the temperature sensors 14, 15. As a result, as shown in FIG. 4B, the heating unit 13 and the temperature sensors 14, 15 are partly detached from the lower layer, forming cantilevered structures. The heating unit 13 and the temperature sensors 14, 15 then form curved surfaces due to warping, and stand up on the substrate 10. The insulating layer underneath the patterns is etched away, by undercut etching, from the edge to half the width of the patterns of the heating unit 13 and the temperature sensors 14, 15. Accordingly, the heating unit 13 and the temperature sensors 14, 15 are warped and form cantilevered structures.

Further, as shown in FIG. 5A, the voids 11 are formed by etching only the area of the surface of the substrate 10 exposed after the insulating layer is removed. In the configuration shown in FIG. 4B, the heating unit 13 and the temperature sensors 14, 15 stand up on the substrate. Compared to the configuration shown in FIG. 4B, the heating unit 13 and the temperature sensors 14, 15 are further away from the substrate 10 that has a large heat capacity, in the configuration shown in FIGS. 5B, 5C, and are thus less affected by the heat from the substrate 10. Accordingly, the configuration shown in FIGS. 5B, 5C is even more effective. A conventional technology is employed to etch the substrate 10 up to inner edges of the insulating layer indicated by dashed lines in FIG. 5A. As a result, the bridges 12 are formed across the voids 11, so that the cantilevered heating unit 13 and the temperature sensors 14, 15 are supported by the bridges 12 fixed at both ends.

Figure 6:
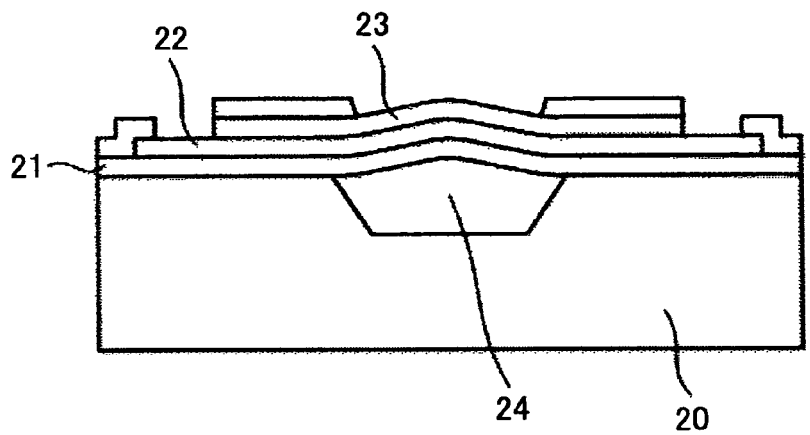
FIG. 6 is a cross-sectional schematic diagram for describing a method of forming three-dimensional temperature sensors.

FIG. 6 is a cross-sectional schematic diagram for describing a method of forming three-dimensional temperature sensors. A heat-resistant substrate 20 is made of, for example, Si, Al, Cu, Ni, Cr, stainless steel, kovar, Mo, W, $Al_2O_3$, $SiO_2$, glass, ceramic, epoxy resin, or polyimide resin. A lower layer 21 is formed by a film formation method such as evaporation coating, sputtering, or CVD, using approximately 0.3 µm to 3 µm of an electrical insulating material such as $SiO_2$, MgO, $Al_2O_3$, $Ta_2O_5$, or $TiO_2$. The degree of vacuum is preferably 0.133 to 133 mPa ($10^{-6}$ to $10^{-3}$ Torr) or less during the film formation. In order to prevent the lower layer 21 from contracting due to an increase in density at the baking/tightening process to be described later, it is necessary to form the film in a high vacuum (low pressure) atmosphere, so as to reduce the porosity and increase the density of the lower layer 21 as much as possible. Next, an upper layer 22 including a heat generating layer and an extraction electrode, etc., is formed by a film formation method such as evaporation coating or sputtering, using approximately 0.1 µm to 3µm of conductive resistor heat generating material such as NiCr, Ir, Pt, Ir—Pt alloy, SiC, TaN, or Kanthal alloy. The upper layer 22 is photo-etched to form a pattern of a predetermined shape. Further, a protective covering layer 23 can be laminated over the upper layer 22 by using a similar electrical insulating material and under similar conditions to those of the lower layer 21. The upper layer 22 and the protective covering layer 23 are formed after the lower layer 21 is formed. Thus, the surfaces of the upper layer 22 or the protective covering layer 23 is more rough and uneven than that of the lower layer 21. Moreover, as the thickness of the film increases, the particle sizes increase, thus increasing pores and deficiencies. As a result, the upper layers shrink more easily than the lower layer 21 at the baking/tightening process, so that beam parts are caused to warp. By lowering the degree of vacuum when forming the upper layer 22 and the protective covering layer 23 to approximately 13.3 mPa to 1.33 Pa ($10^{-4}$ to $10^{-2}$ Torr), which is lower than that when forming the lower layer 21, a porous film can be formed. Thus, the upper layers can be made to shrink more easily than the lower layer 21 at the baking/tightening process. By forming a void 24 in the substrate 20 by etching, a beam configured with the lower layer 21 and the upper layer 22, or a beam configured with the lower layer 21, the upper layer 22, and the protective covering layer 23 is formed. Further, a predetermined warp shape can be formed by baking/tightening this beam at 350° C. to 800° C. The warp shape can be formed even if the baking/tightening process is performed before forming the void 24. In this case, the upper layer 22 and the protective covering layer 23 is caused to shrink after the void 24 is formed, and this shrinking force eliminates a binding force from the substrate 20. Accordingly, the baking/tightening process and the formation of the void 24 can be performed in any order.

The thermal tracing technique used for measuring the flow rate of a fluid is described below. For example, in a flow rate measuring instrument disclosed in Japanese Laid-Open Patent Application No. S60-186714, a heating unit provided inside a piping generates and supplies a predetermined heat pulse to the fluid flowing through the piping. A temperature sensor is located downstream at a predetermined distance from the heating unit. The instrument supplies a heat pulse to flowing fluid, and detects, at a predetermined location, the maximum temperature of heat distribution of the fluid. The instrument then obtains the flow rate of the fluid based on the amount of time from when the heat pulse is supplied, to when the maximum temperature is detected.

Figure 7:
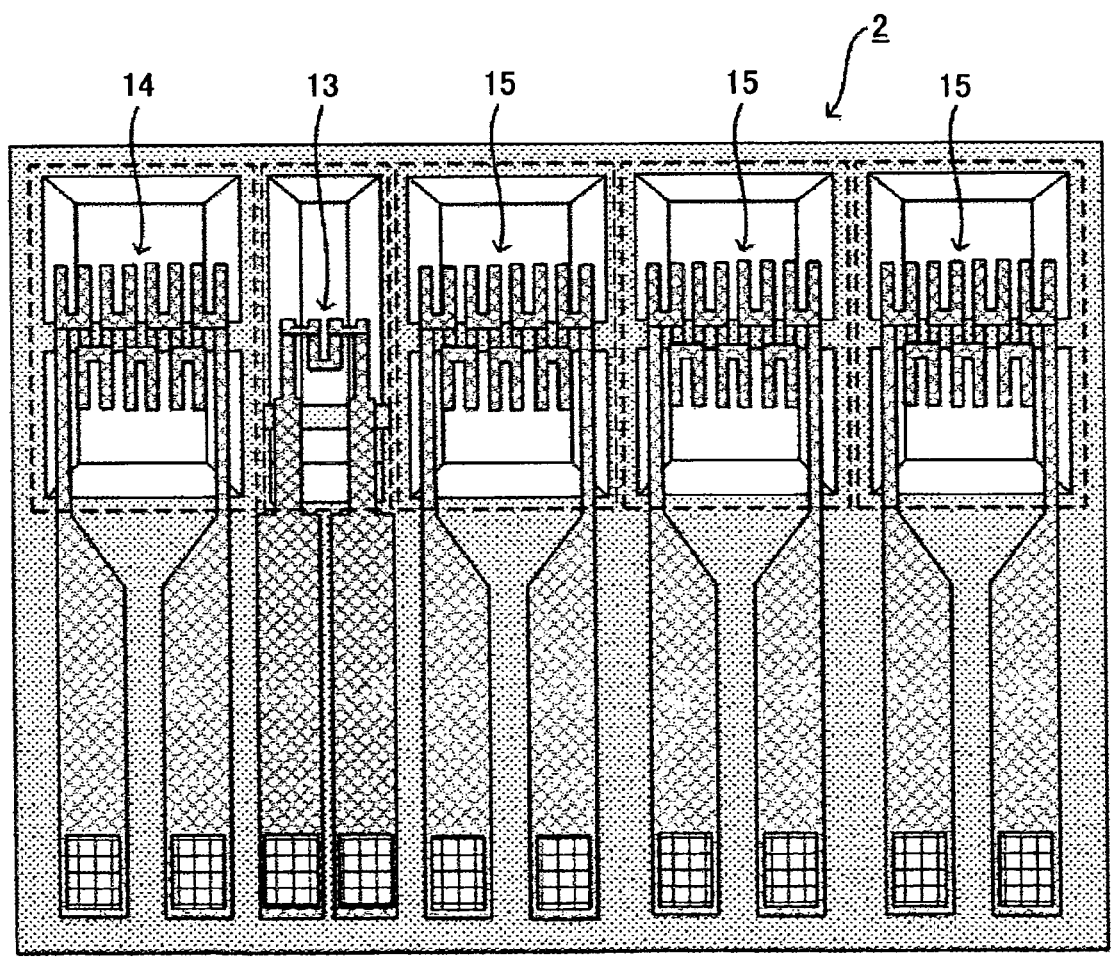
FIG. 7 is a plan view of a detector element according to a second embodiment of the present invention.

FIG. 7 is a plan view of a configuration of a detector element 2 according to a second embodiment of the present invention. Elements corresponding to those in FIG. 1 are denoted by the same reference numbers. The detector element 2 according to the second embodiment includes plural temperature sensors 15 arranged in parallel. The heating unit 13 is intermittently heated, and the flow velocity is measured by capturing the time that it takes for each heat wave to reach each of the temperature sensors 15 located at predetermined distances.

Figure 8:
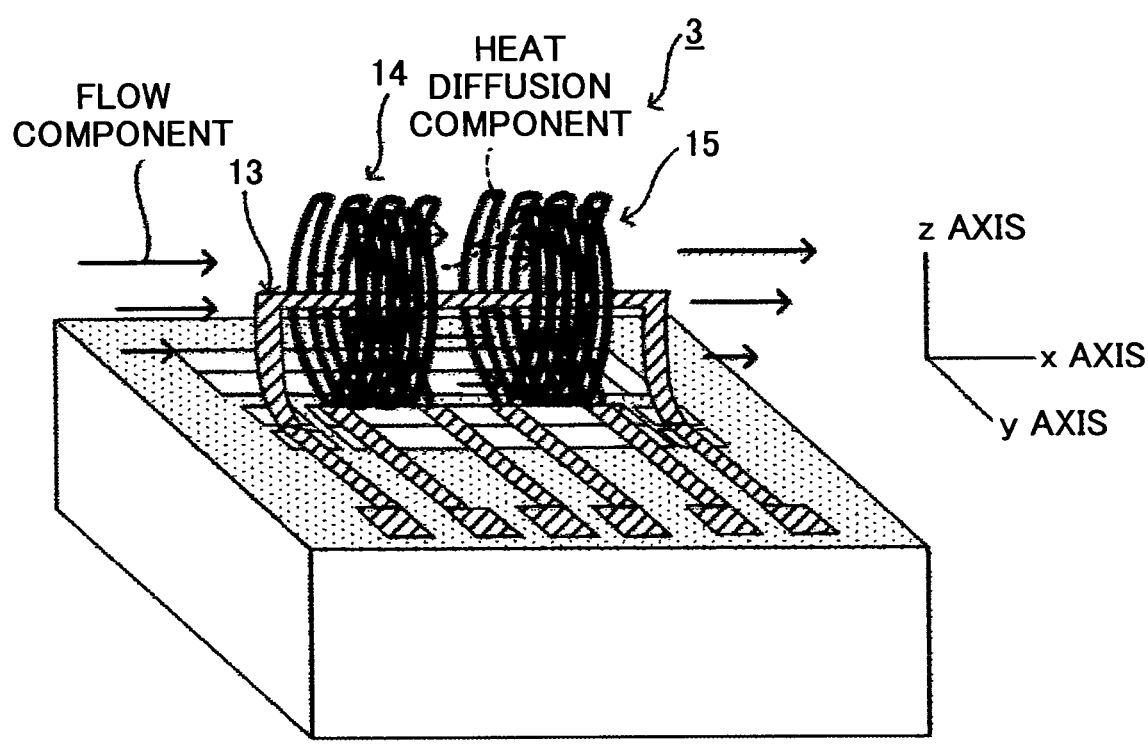
FIG. 8 is a perspective view of a detector element according to a third embodiment of the present invention.

FIG. 8 is a perspective view of a configuration of a detector element 3 according to a third embodiment of the present invention. Elements corresponding to those in FIG. 1 are denoted by the same reference numbers. In the detector element 3 according to the third embodiment, the heating unit 13 is disposed at an x axis position inside the two temperature sensors 14, 15 standing up on the substrate 10. The fluid flows along the x axis, and heat from the heating unit 13 is supplied to the fluid. The heat diffuses not only along the flow, but also in a three-dimensional space. Accordingly, the temperature sensors 14, 15 can capture the heat diffused from the heating unit 13 in a three-dimensional space. The heat generating section of the heating unit 13 is inside of the flow, while the temperature sensors 14, 15 are outside the flow. Thus, even if the angle of the flow along the x axis changes, the flow can be captured in a three-dimensional space. Accordingly, the position of the sensor can be easily adjusted with respect to the axis of the flow. Compared to the flowsensor structure according to the first and second embodiments in which the heating unit 13 and the temperature sensors 14, 15 are arranged in parallel, the heating unit 13 is located closer to the temperature sensors 14, 15 in the third embodiment. Thus, the third embodiment is highly effective for detecting an extremely small amount of flow.

Figure 9:
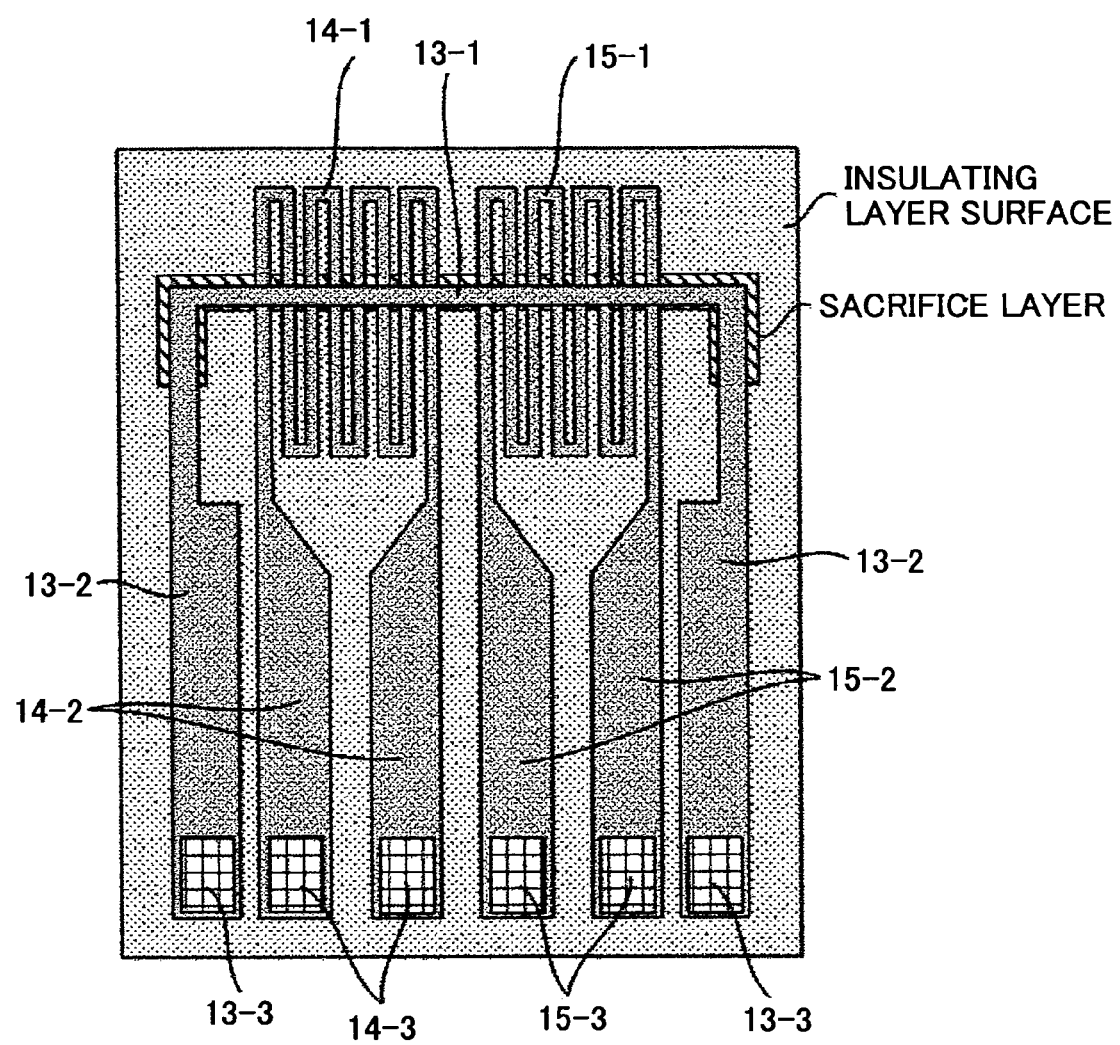
FIG. 9 is a diagram for describing fabrication steps of the detector element according to the third embodiment.
Figure 10B:
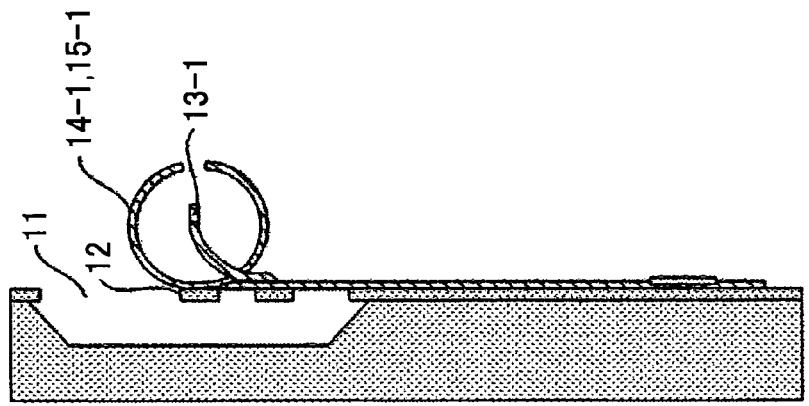
FIGS. 10A, 10B are diagrams for describing fabrication steps of the detector element according to the third embodiment.
Figure 10A:
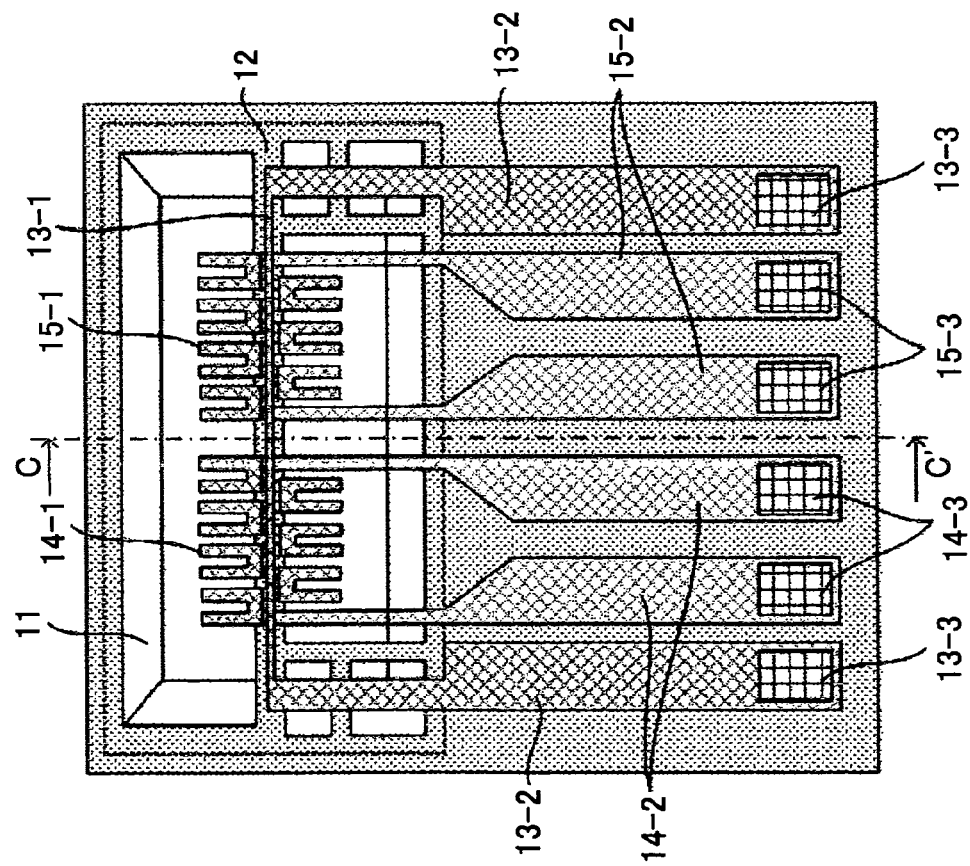

A method of fabricating the detector element 3 according to the third embodiment is described with reference to FIGS. 9 and 10. FIGS. 9 and 10A are plan views, and FIG. 10B is a cross-sectional view taken along line C-C' of FIG. 10B. Elements corresponding to those in FIG. 1 are denoted by the same reference numbers.

As shown in FIG. 9, the heating unit 13 overlaps the temperature sensors 14, 15, and therefore, the heating unit 13 is to be formed by using a sacrifice layer, in a subsequent step after the temperature sensors 14, 15 are formed. First, patterns made of conductive material films are formed on the substrate 10 for the temperature sensor electrodes 14-1, 15-1, the detection leads 14-2, 15-2, and the electrode pads 14-3, 15-3 of the temperature sensors 14, 15, respectively. A metal material having a high resistance temperature coefficient such as Pt, W is used for the heating unit 13 and the temperature sensors 14, 15. Next, patterns made of, for example, Ni, are formed in areas to become the heating unit 13, in a sacrifice layer that can be selectively etched and removed later. Patterns made of conductive material films are formed for the heat generating electrode 13-1, the power supply leads 13-2, and the electrode pads 13-3 of the heating unit 13. Then, the sacrifice layer in the area corresponding to the heating unit 13, and the insulating layer in the area corresponding to the heating unit 13 and the temperature sensors 14, 15 on the substrate 10 are removed by etching. Subsequently, only the exposed areas of the surface of the substrate 10 are etched to form the voids 11. As shown in FIG. 10B, the heating unit 13 and the temperature sensors 14, 15 are partly detached from the lower layer, forming cantilevered structures. The heating unit 13 and the temperature sensors 14, 15 form curved surfaces due to warping, and stand up on the substrate 10. Heat is captured from the heating unit 13, which is positioned along the axis of the temperature sensors 14, 15. As shown in FIG. 10B, the heating unit 13 has a bridged structure fixed at both ends, supporting a cantilevered structure. Therefore, the bridged beam structure is hardly warped, and is almost a straight line.

Figure 11:
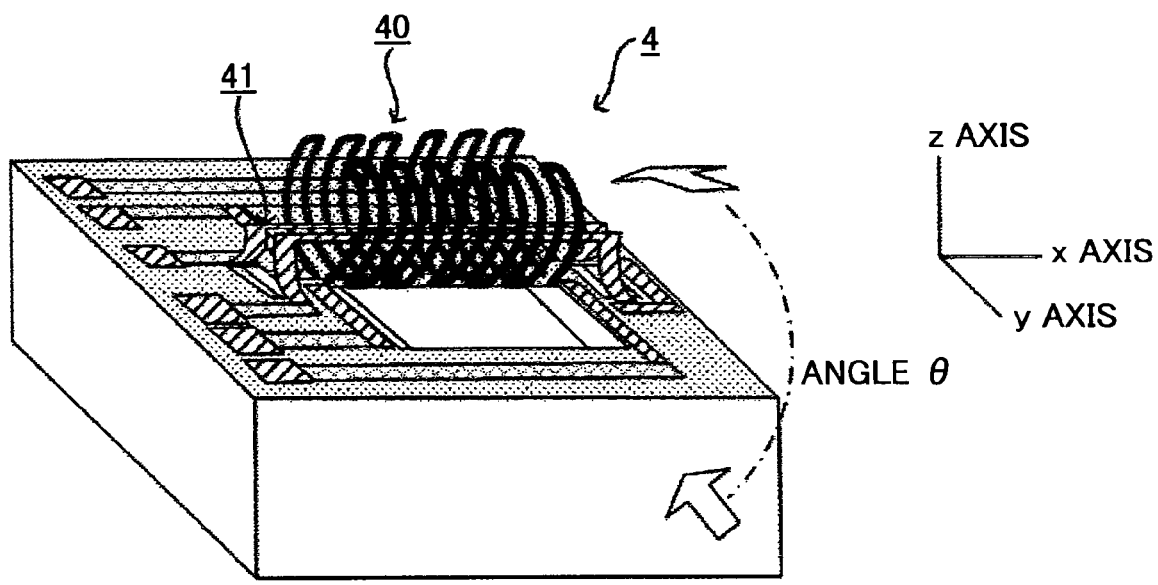
FIG. 11 is a perspective view of a detector element according to a fourth embodiment of the present invention.

FIG. 11 is a perspective view of a configuration of a detector element 4 according to a fourth embodiment of the present invention. The detector element 4 according to the fourth embodiment has a flowsensor structure similar to that of the detector element 3 according to the third embodiment, in that a heating unit 41 is disposed inside a temperature sensor 40. However, the operations are different from the third embodiment. Specifically, the fluid is guided to a y-z surface, and is made to flow substantially perpendicular to the pipe-shaped temperature sensor 40 and the heating unit 41. Because the heating unit 41 is located at the axis of the pipe, even if the flow shifts within a range of an angle θ at the z-y surface, effects on detections are small. The allowable range of shift in the angle at the x-y surface is large because the temperature sensor 40 extends transversely. Moreover, the temperature sensor 40 has a rectifying function due to its comb-teeth shape, so that stable output can be obtained even under turbulent conditions, without requiring a rectifying device.

A method of fabricating the detector element 4 according to the fourth embodiment is described with reference to FIGS. 12A through 12C. FIG. 12 is a plan view, FIG. 12B is a cross-sectional view taken along line D-D' of FIG. 12A, and FIG. 12C is a cross-sectional view taken along line E-E' of FIG. 12A. In the fabrication method of the detector element 3 according to the third embodiment shown in FIG. 8, the heating unit 13 is made to overlap the temperature sensors 14, 15, and therefore, the heating unit 13 is formed in a subsequent step by using the sacrifice layer. However, the detector element can also be fabricated by plane machining by making use of the warping effect. Either method can be employed as long as the heating unit 13 is located inside the temperature sensors 14, 15 when the temperature sensors 14, 15 stand up on the substrate 10. Accordingly, as shown in FIG. 12, a pattern for a heat generating electrode 41-1 of the heating unit 41 is formed between temperature sensor electrodes 40-1 so as not to overlap the temperature sensor 40 on the substrate 10. Patterns of the temperature sensor 40 and the heating unit 41 are warped due to cantilevered structures, thereby forming the heating unit 41 inside the temperature sensor 40. Only a single film made of Pt is needed, for both the heating unit 41 and the temperature sensor 40. On the film, a pair of patterns opposite to each other is formed for the temperature sensor 40, and a pattern for the heating unit 41 is formed therebetween. Thus, convenience is enhanced, as a sacrifice layer is not required.

Figure 13:
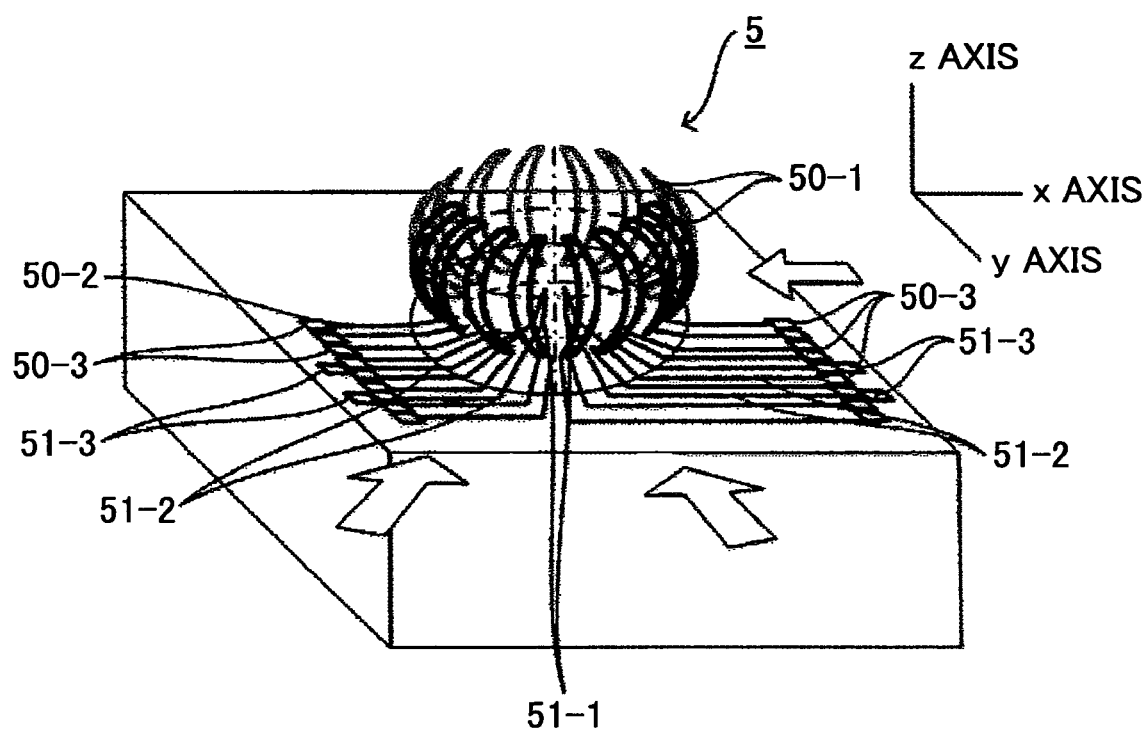
FIG. 13 is a perspective view of a detector element according to a fifth embodiment of the present invention.

FIG. 13 is a perspective view of a configuration of a detector element 5 according to a fifth embodiment of the present invention. Similar to the flowsensor structure of the detector element 4 according to the fourth embodiment shown in FIG. 11, a heating unit 51 is disposed in a temperature sensor 50. In the detector element 5 according to the fifth embodiment, a temperature sensor electrode 50-1 of the temperature sensor 50 is ring-shaped. Similar to the ring-shaped temperature sensor electrode 50-1 of the temperature sensor 50, detection leads 50-2, power supply leads 51-2 of the heating unit 51, and electrode pads 50-3, 51-3 are arranged radially, although only half of these are shown in FIG. 13. The temperature sensor electrode 50-1 of the temperature sensor 50 and a heat generating electrode 51-1 of the heating unit 51 are arranged reversed to each other, so as to face each other when they are warped. In the detector element 5 according to the fifth embodiment, the fluid is guided to an x-y surface, and the heating unit 51 is located in the center of the temperature sensor 50, surrounded by the curved surface of the temperature sensor 50. Therefore, even if the flow shifts slightly along the z axis, effects on detections are small. Accordingly, the flow can be detected in any direction along the x-y surface. Moreover, the temperature sensor 50 has a rectifying function due to its comb-teeth shape, so that stable output can be obtained even under turbulent conditions, without requiring a rectifying device.

A method of fabricating the detector element 5 according to the fifth embodiment is described with reference to FIGS.

Figure 14:
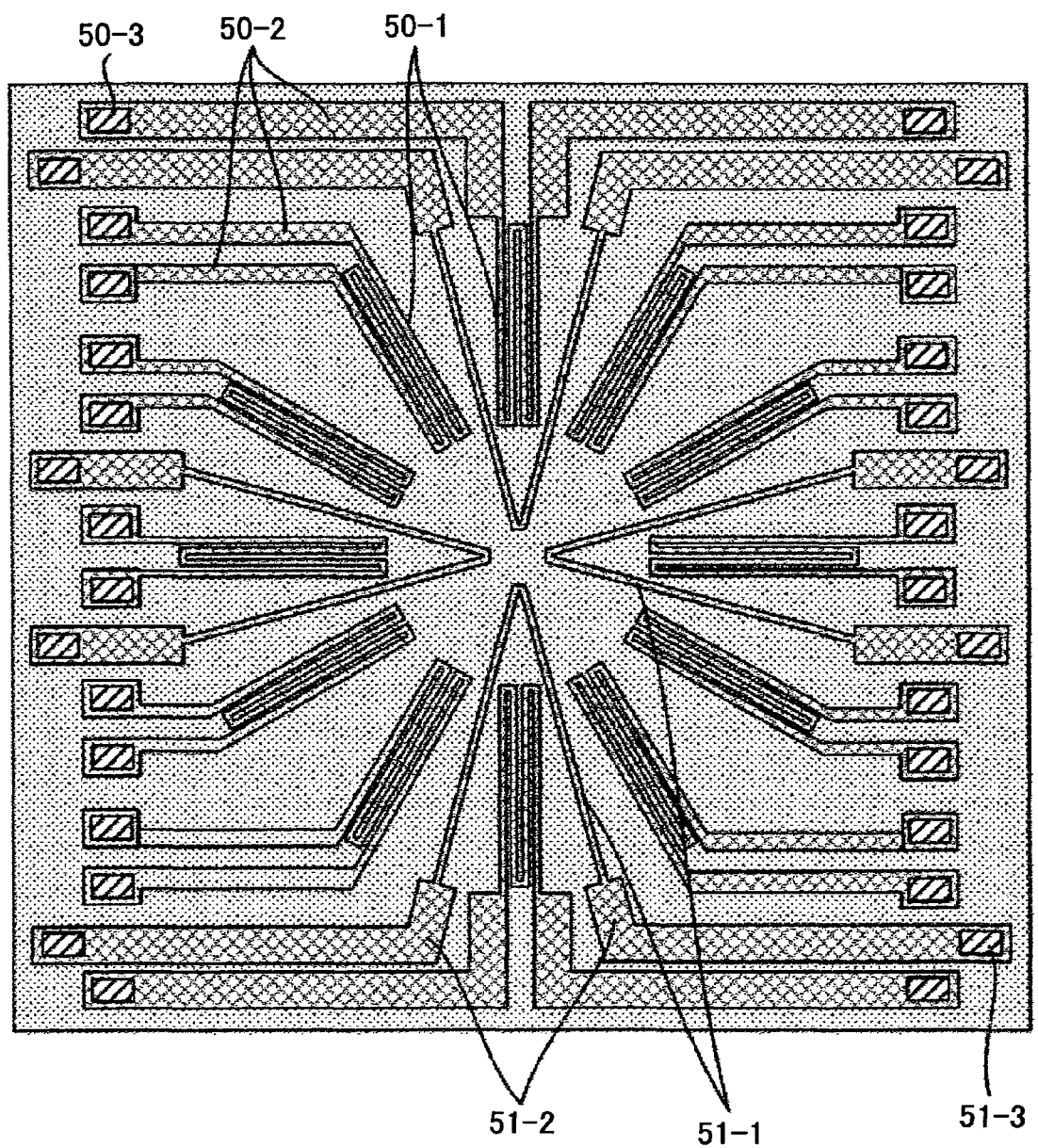
FIG. 14 is a plan view of the detector element according to the fifth embodiment of the present invention.
Figure 15A:
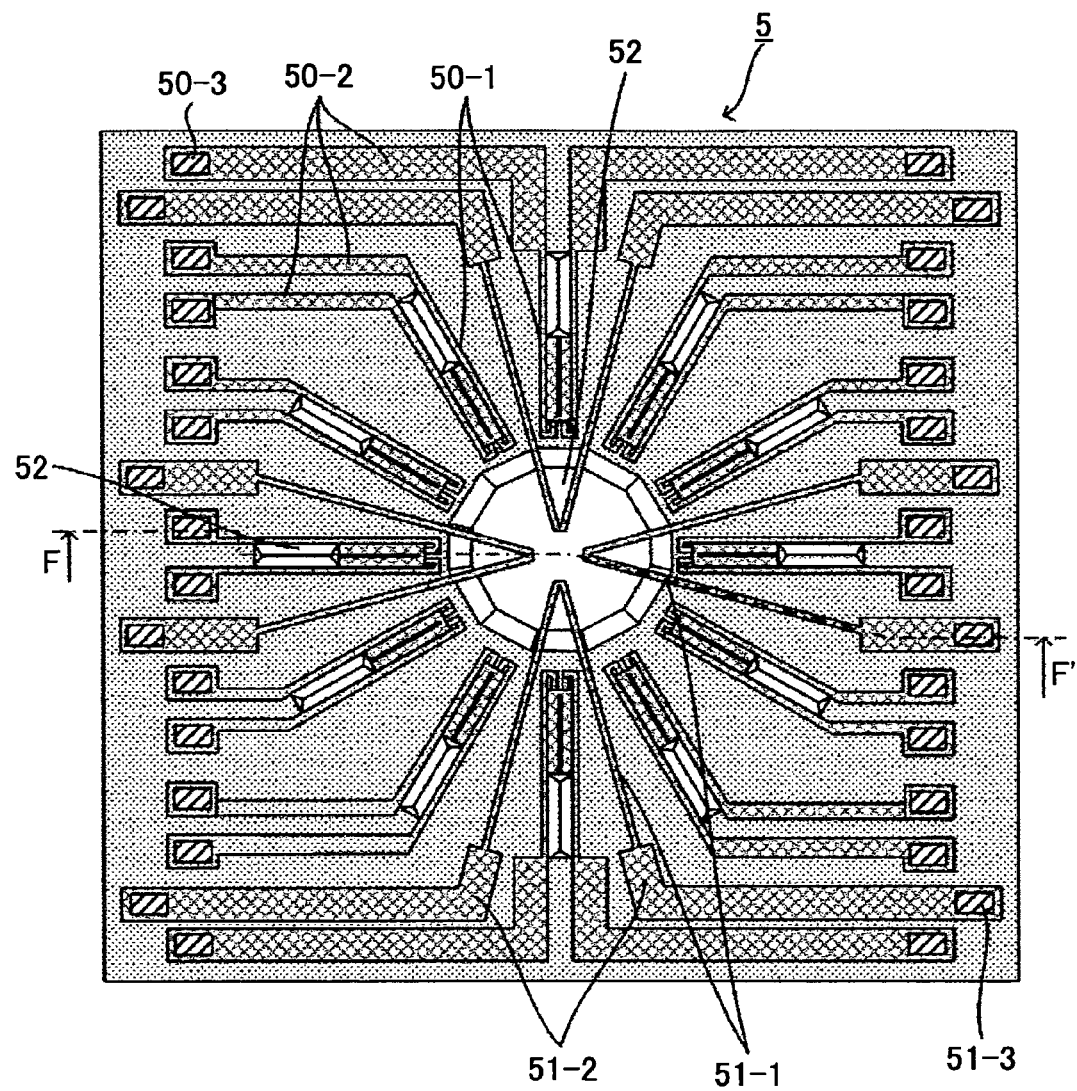
FIGS. 15A, 15B are diagrams for describing fabrication steps of the detector element according to the fifth embodiment.
Figure 15B:
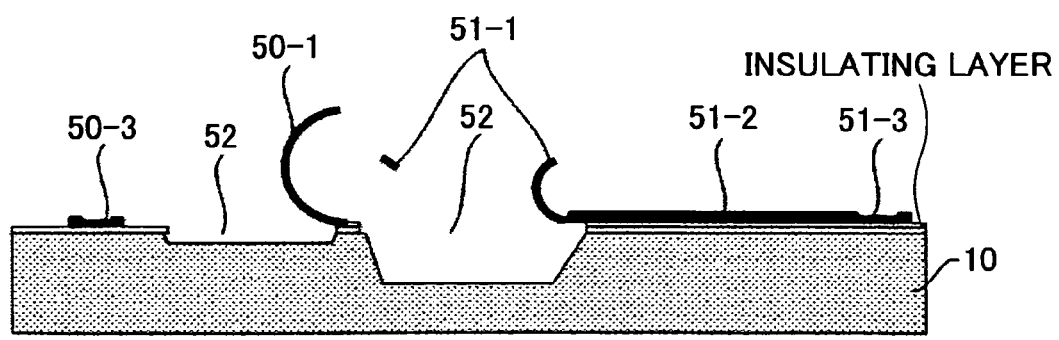

14, 15A, and 15B. FIG. 14 and FIG. 15A are plan views, and FIG. 15B is a cross-sectional view taken along line F-F' of FIG. 15A. As shown in FIG. 14, patterns made of conductive material films are formed on the substrate 10 for the temperature sensor electrode 50-1 of the temperature sensor 50, the detection leads 50-2, the heat generating electrode 51-1 and the power supply leads 51-2 of the heating unit 51, and the electrode pads 50-3, 51-3. As shown in FIGS. 15A, 15B, the insulating layer in the area corresponding to the temperature sensor electrode 50-1 of the temperature sensor 50 and the heat generating electrode 51-1 of the heating unit 51 on the substrate 10 are removed by etching. The temperature sensor 50 and the heating unit 51 are partly detached from the lower layer, forming cantilevered structures. The temperature sensor 50 and the heating unit 51 then form curved surfaces due to warping, and stand up on the substrate 10. Further, only the exposed areas of the surface of the substrate 10 are etched to form voids 52.

Figure 16A:
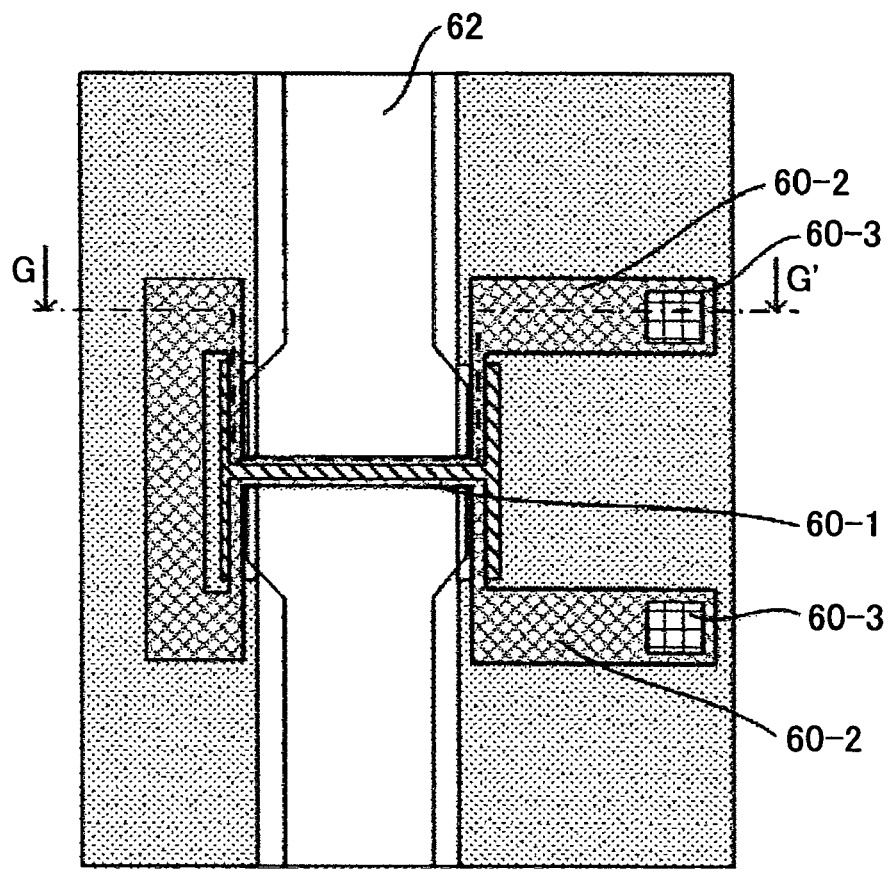
FIGS. 16A, 16B are schematic diagrams of a heating unit of a detector element according to a sixth embodiment of the present invention.
Figure 16B:
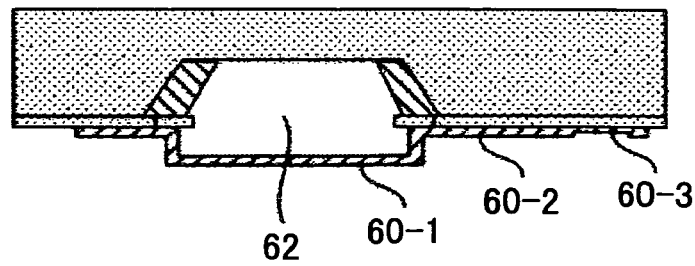
Figure 17A:
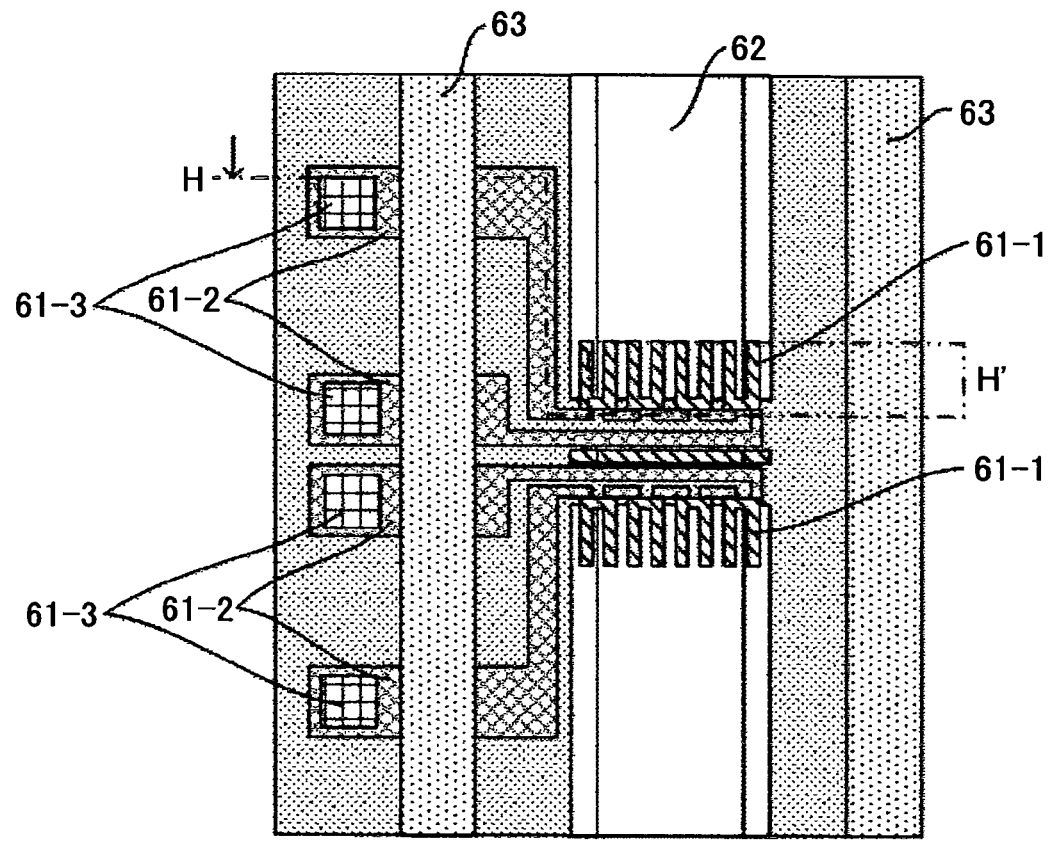
FIGS. 17A, 17B are schematic diagrams of a temperature sensor of the detector element according to the sixth embodiment.
Figure 17B:
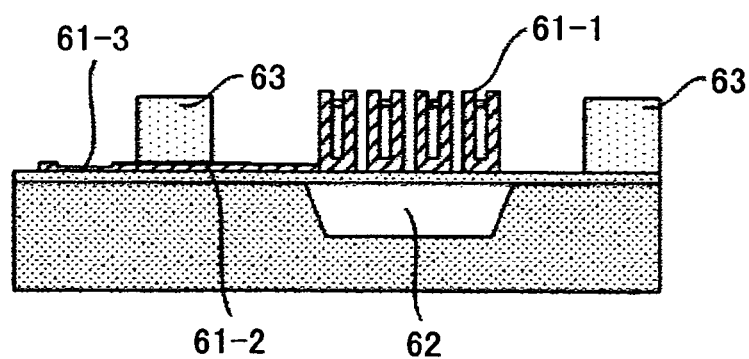
Figure 18A:
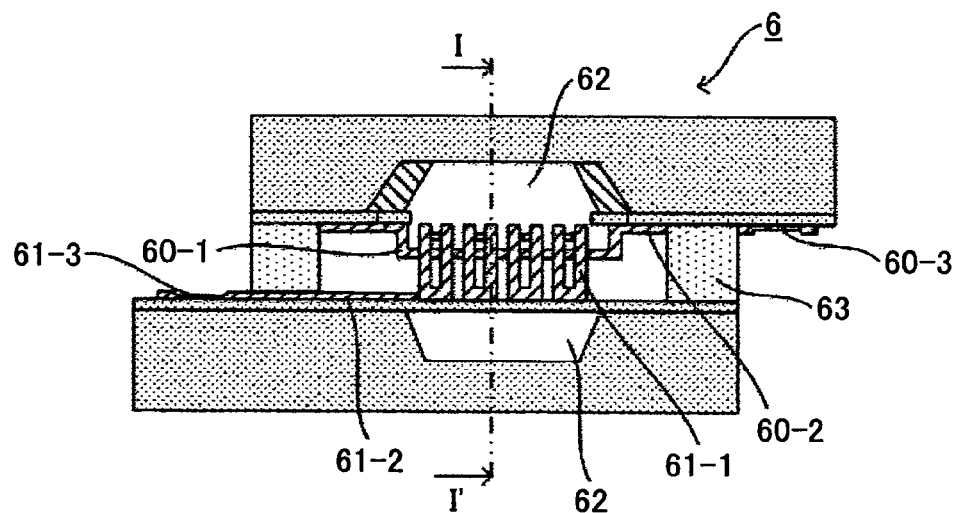
FIGS. 18A, 18B are overall views of the detector element according to the sixth embodiment.
Figure 18B:
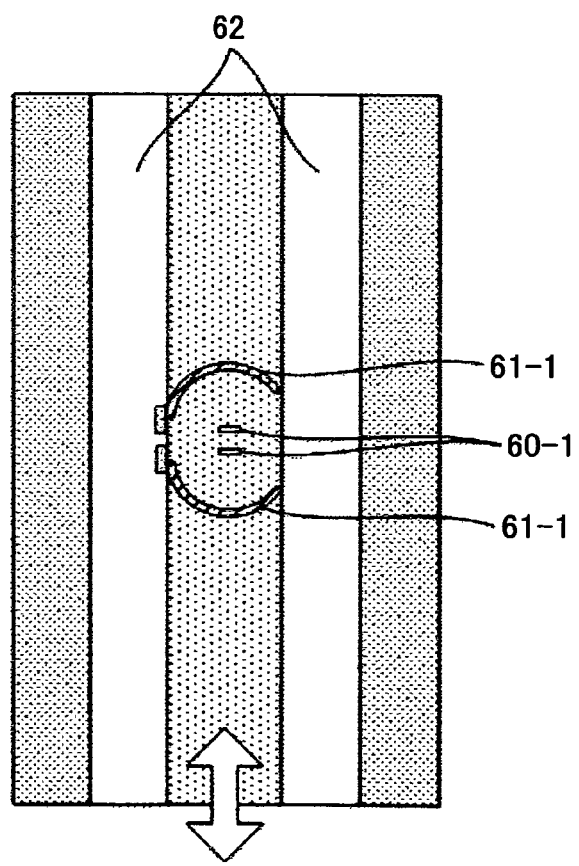

FIGS. 16A, 16B are diagrams of a configuration of a heating unit 60 of a detector element 6 according to a sixth embodiment of the present invention. FIGS. 17A, 17B are diagrams of a configuration of a temperature sensor 61 of the detector element 6 according to the present embodiment. FIGS. 18A, 18B are diagrams of the overall configuration of the detector element 6 according to the present embodiment. FIGS. 16A, 17A are plan views, FIG. 16B is a cross-sectional view taken along line G-G' of FIG. 16A, FIG. 17B is a cross-sectional view taken along line H-H' of FIG. 17A, and FIG. 18B is a cross-sectional view taken along line I-I' of FIG. 18A. In the detector element 6 according to the present embodiment shown in FIG. 18, a substrate on which the heating unit 60 shown in FIGS. 16A, 16B is formed, is combined with another substrate, on which the temperature sensor 61 shown in FIGS. 17A, 17B is formed. Fluid is made to flow through a void 62 formed by combining these substrates. According to the conventional technology, before heat is transported from the heating unit to the temperature sensor, the heat is affected by heat exchange between the substrate walls. However, in the present embodiment, the temperature sensor is disposed in front of the position where the fluid reaches the substrate wall, so that the effect of heat exchange can be reduced. Compared to a case of using a single substrate, the configuration of the present embodiment requires the extra work of combining the two substrates with precision. On the other hand, the present embodiment is advantageous in that the microstructure of the heating unit and the temperature sensor is protected in between the substrates, instead of standing up and being exposed on a substrate. Accordingly, the microstructure is resistant to damage, and thus easy to handle.

Figure 21:
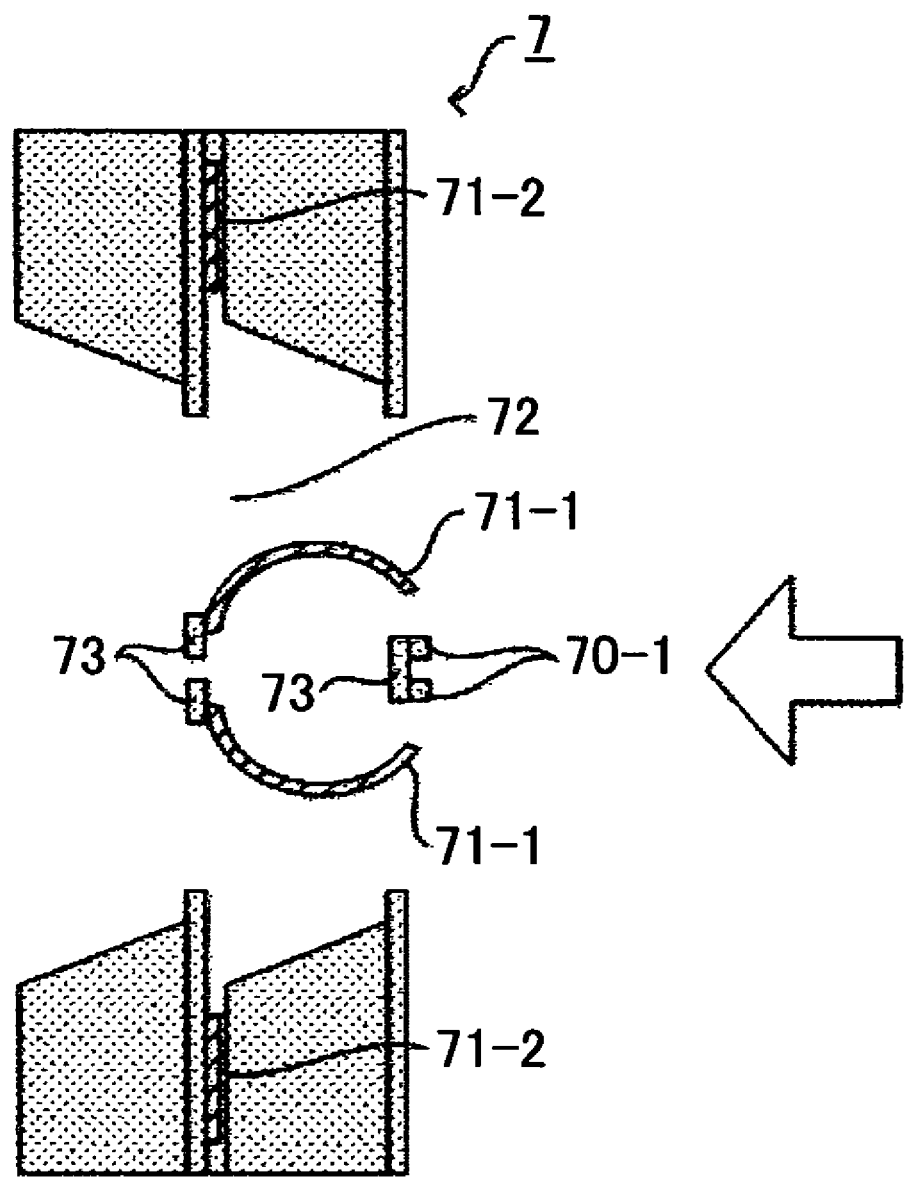
FIG. 21 is a cross-sectional schematic diagram of the detector element according to the seventh embodiment.

FIGS. 19A, 19B are diagrams of a configuration of a heating unit 70 of a detector element 7 according to a seventh embodiment of the present invention. FIGS. 20A, 20B are diagrams of a configuration of a temperature sensor 71 of the detector element 7 according to the present embodiment. FIG. 21 provides schematic diagrams of the overall configuration of the detector element 7 according to the present embodiment. FIGS. 19A, 20A are plan views, FIG. 19B is a cross-sectional view taken along line J-J' of FIG. 19A, and FIG. 20B is a cross-sectional view taken along line K-K' of FIG. 20A. In the detector element 7, the heating unit 70 is located inside the temperature sensor 71. Accordingly, as shown in FIGS. 19A, 19B, the heating unit 20 has a bridged structure fixed at both ends without being warped, while the temperature sensor 71 is warped as shown in FIG. 20. Thus, the heating unit 70 is formed inside the temperature sensor 71 as shown in FIG. 21.

Figure 22:
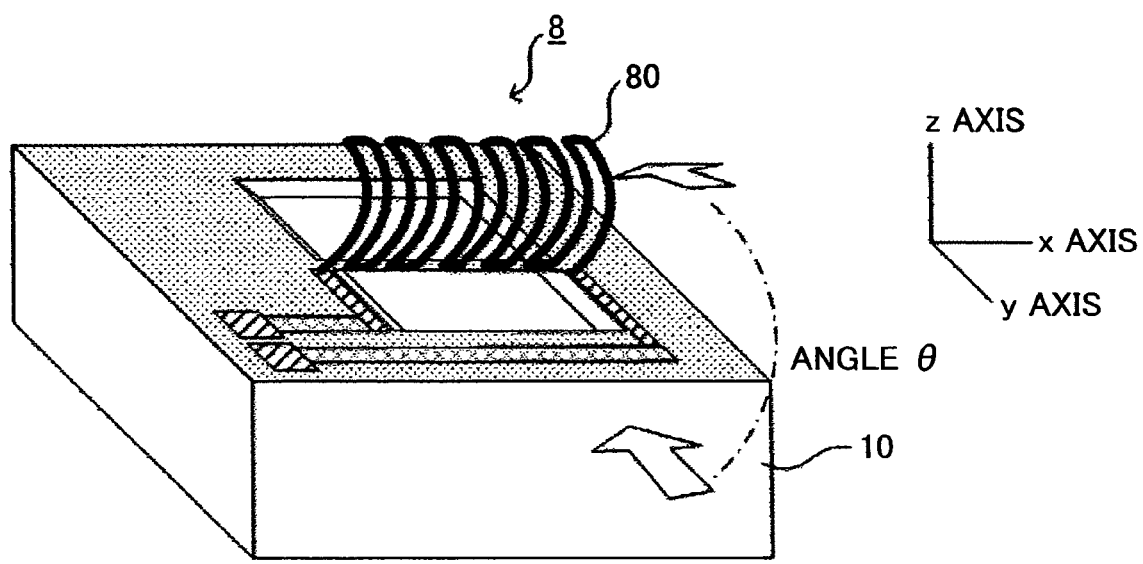
FIG. 22 is a perspective view of a detector element according to an eighth embodiment of the present invention.

FIG. 22 is a diagram of a configuration of a detector element 8 according to an eighth embodiment of the present invention. FIG. 23A is a plan view of the detector element 8 according to the present embodiment, and FIG. 23B is a cross-sectional view taken along line L-L' of FIG. 23A. Elements corresponding to those in FIG. 1 are denoted by the same reference numbers. The detector element 8 according to the present embodiment shown in FIGS. 22, 23A, 23B is disposed on the substrate 10, including a single, comb-teeth shaped resistive element 80 that is warped, forming a cantilevered structure. According to the sensing manner of an atmosphere measuring device and flow sensor disclosed in U.S. Pat. No. 5,551,283, the resistive element 80 serves as both a heating unit and a temperature sensor. The resistive element 80 has applied a small current or a small voltage, which is small enough so as not to heat the resistive element 80. At a different timing, the resistive element 80 has applied a large current or a large voltage, so as to be heated. A resistance value detecting unit, not shown in the figure, detects a first resistance value indicated by the resistive element 80 when a small current or a small voltage is applied, and a second resistance value indicated by the resistive element 80 when a large current or a large voltage is applied. The first resistance value is subtracted from the second resistance value, and the flow rate is calculated based on the result of subtraction.

According to one embodiment of the present invention, three-dimensional heat diffusion can be captured with a three-dimensional temperature sensor, a three-dimensional isothermal line can thereby be captured by using the temperature sensor, and the distance between a heating unit and the temperature sensor can be made shorter than the distance between the heater and a substrate.

Further, according to one embodiment of the present invention, it is possible to fabricate a detector element by plane machining, and use the detector element as a flowsensor for measuring a flow velocity and a flow rate of a fluid.

Further, according to one embodiment of the present invention, it is possible to provide a sensor capable of measuring the time it takes for heat to be transported, and calculating flow velocity.

Further, according to one embodiment of the present invention, it is possible to make the distance between the heating unit and the temperature sensor even shorter so as to detect minute amounts of change.

Further, according to one embodiment of the present invention, it is possible to detect the direction of a fluid flow.

Further, according to one embodiment of the present invention, it is possible to perform measurements even if the angle of the flow shifts, and even under turbulent conditions.

Further, according to one embodiment of the present invention, it is possible provide a detector element with a high degree of freedom in structure and shape.

Further, according to one embodiment of the present invention, it is possible to perform measurements even if the angle of the flow shifts within a range of an angle θ at the x-y surface and the z-y surface. Accordingly, the allowable range of shift is wide.

Further, according to one embodiment of the present invention, loss of heat due to heat transfer is small, and measurements can be performed corresponding to the direction of the flow.

Figure 24:
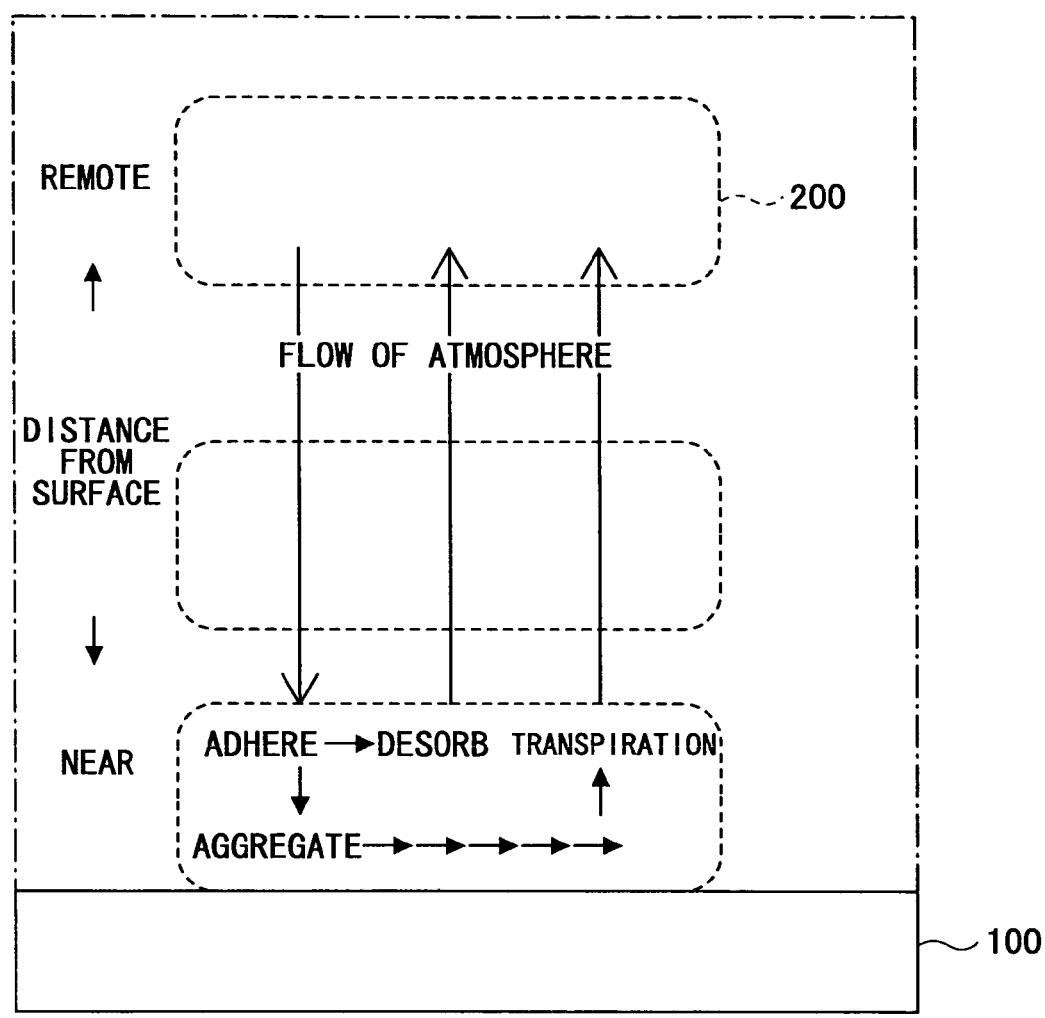
FIG. 24 is a schematic diagram of behavior of an atmosphere with respect to an object surface.

A description of another embodiment according to the present invention is given below. First, a description is given of changes in an atmosphere surrounding an object, as gas in the atmosphere adheres, aggregates, and condenses on the surface of the object, and the aggregated liquid undergoes transpiration. As shown in FIG. 24, when gas in a surrounding atmosphere 200 adheres and aggregates on the surface of an object 100, the gas in the atmosphere 200 more distant remote from the surface of the object 100 flows toward the surface of the object 100. When the gas adhered on the surface of the object 100 is desorbed, or when the liquid aggregated on the surface of the object 100 undergoes transpiration, the gas of the atmosphere 200 near the surface of the object 100 flows away from the surface of the object 100.

Figure 25A:
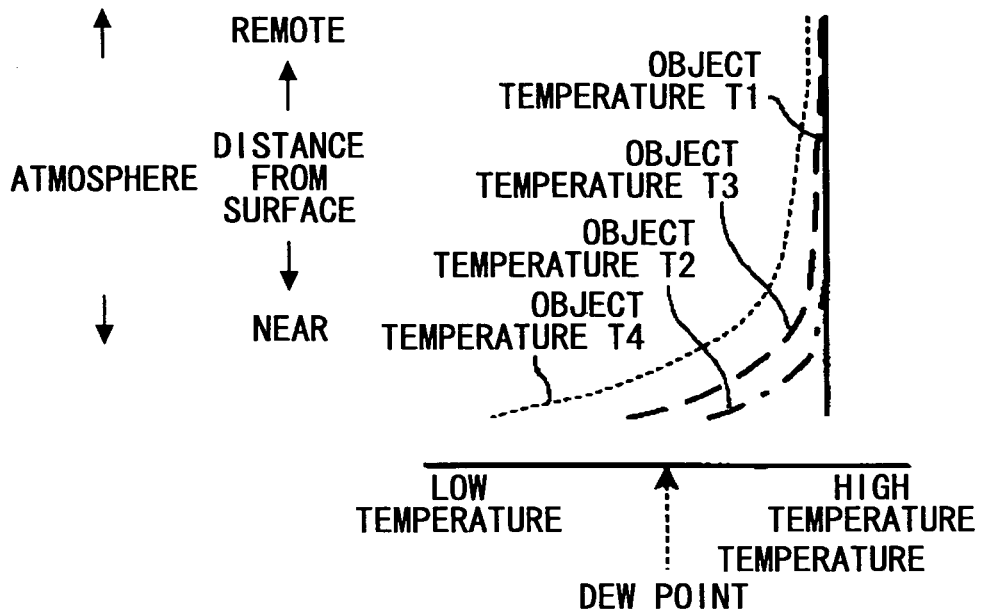
FIGS. 25A, 25B are graphs of the temperature distribution and the relative humidity distribution of the atmosphere, which change according to the distance of the atmosphere from the surface of an object.
Figure 25B:
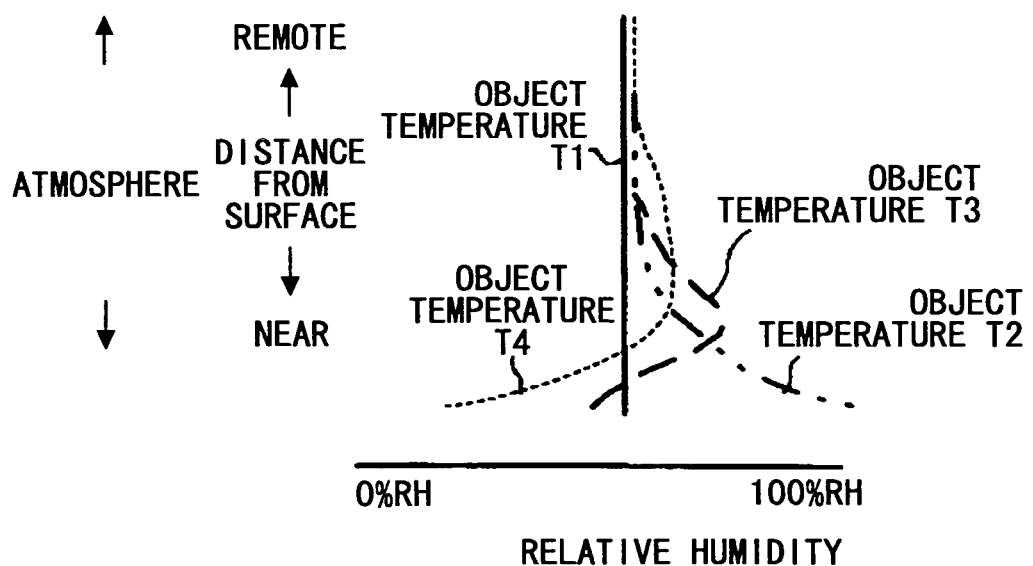

A temperature distribution or a density distribution is generated in the atmosphere 200 along the direction of gas flow, according to the absorption or the aggregation on the surface of the object 100. FIGS. 25A, 25B are graphs of the temperature distribution and the relative humidity distribution of the atmosphere 200, which change according to the distance of the atmosphere 200 from the surface of the object 100. It is assumed in FIGS. 25A, 25B that the temperature of the atmosphere 200 at a remote location is T1, and the temperature of the surface of the object 100 is T1, T2, T3, and T4, where T1>T2>T3>T4, and a dew-point temperature of the atmosphere Td is between the temperature T2 and the temperature T3. In FIG. 25A, the horizontal axis represents the temperature of the atmosphere 200, and the vertical axis represents the distance from the surface of the object 100. In FIG. 25B, the horizontal axis represents the relative humidity in the atmosphere 200, and the vertical axis represents the distance from the surface of the object 100.

When the temperature of the surface of the object is T1, which is the same as the temperature T1 of the atmosphere 200, the distribution of the relative humidity of the atmosphere 200 is even. When the temperature of the surface of the object is T2, which is lower than the temperature T1 of the atmosphere 200, the temperature of the atmosphere 200 near the surface of the object 100 decreases. This is caused by thermodynamic interactions between gas molecules of air and moisture and the surface of the object 100. As the temperature of the atmosphere 200 near the surface of the object 100 decreases, the saturated water vapor pressure decreases, thus increasing the relative humidity indicated by water vapor pressure/saturated water vapor pressure. At this stage, the amount of water vapor molecules adhering on the surface of the object 100 increases, but more water vapor molecules are desorbed. Therefore, water molecules, which cause dew condensation, are not yet formed on the surface of the object 100.

When the temperature of the surface of the object is T3, which is lower than the temperature T1 of the atmosphere 200 and even lower than the dew-point temperature of the atmosphere Td, the amount of water molecules adhering on the surface of the object 100 exceeds the amount of water molecules desorbed. As a result, water vapor molecules form clusters of water molecules, causing dew condensation on the surface of the object 100. Even if the amount of water vapor molecules transported from a remote location from the surface of the object 100 toward the surface of the object 100 increases, the amount of water vapor molecules typically becomes insufficient near the surface of the object 100. Specifically, 1 mol, 22,400 cc of water vapor is aggregated into 18 cc of water near the surface of the object 100, such that the volume becomes 1/1,244, although variations may be caused by the temperature of the atmosphere 200 near the surface of the object 100. Accordingly, even if the temperature of the surface of the object 100 decreases to T3, the relative humidity in the atmosphere 200 near the surface of the object 100 becomes lower than a remote location. As shown in FIGS. 25A, 25B, in the atmosphere 200 in the middle of a location near the surface of the object 100 and a location remote from the surface of the object 100, the temperature decreases, and the relative humidity thus increases. When the temperature of the surface of the object further decreases to T4, which is lower than the temperature T1 of the atmosphere 200, dew condensation further progresses. Accordingly, compared to when the temperature of the surface of the object 100 is T3, the relative humidity in the atmosphere 200 near the surface of the object 100 becomes lower than a remote location to a greater degree.

The dew condensation progresses as long as the temperature of the surface of the object 100 is equal to or less than the dew-point temperature of the atmosphere Td. When the temperature of the surface of the object 100 exceeds the dew-point temperature of the atmosphere Td, the water undergoes transpiration, and water vapor molecules are transported from the surface of the object 100 to a remote location. As described above, the transportation state of the atmosphere 200 with respect to the surface of the object 100, i.e., whether the atmosphere 200 is in the absorption/aggregation process, the balanced status, or the transpiration process, can be detected from a remote location. Specifically, dew condensation behavior and transpiration behavior on the surface of the object 100 can be detected from a location remote from the surface of the object 100 in a non-contact manner by measuring changes in the temperature gradient, the humidity gradient, and the flow of the atmosphere 200.

Figure 26:
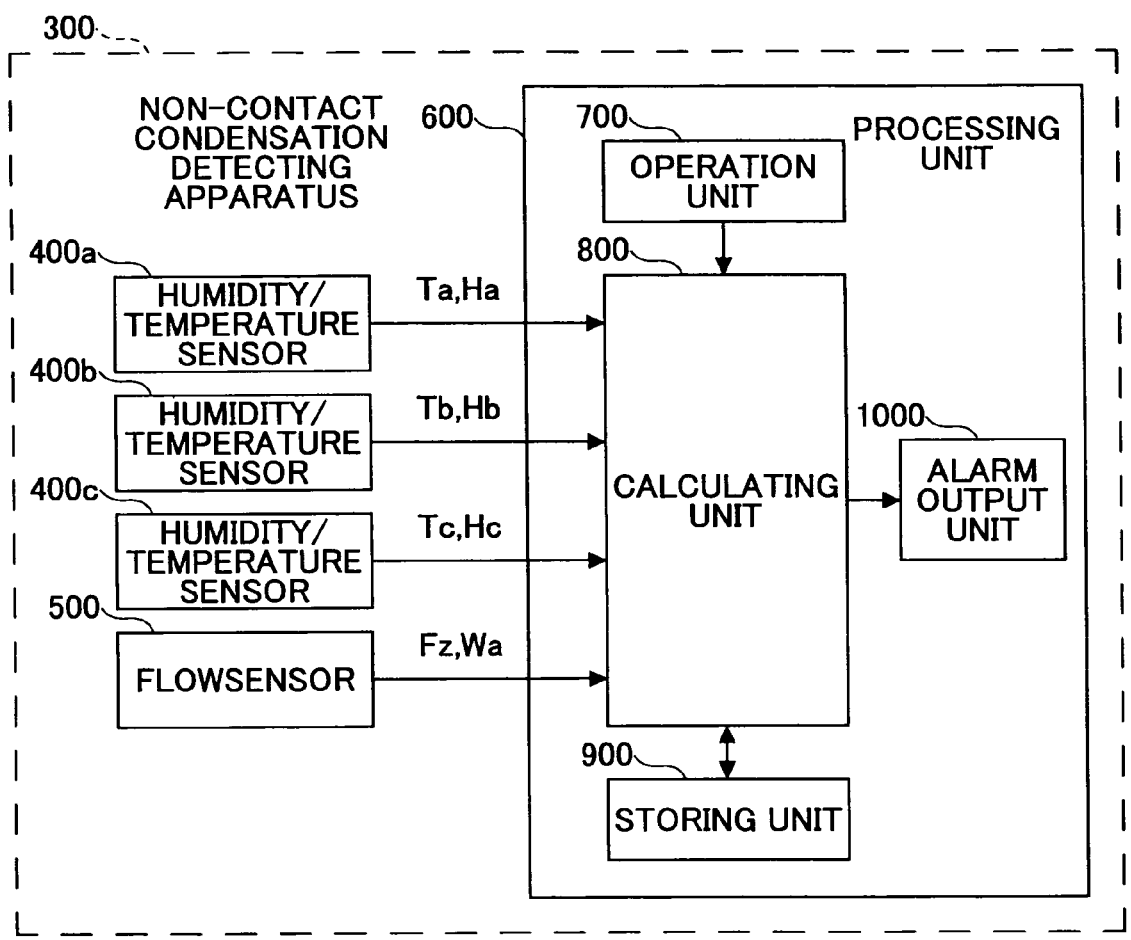
FIG. 26 is a block diagram of a non-contact condensation detecting apparatus according to the present invention.
Figure 27A:
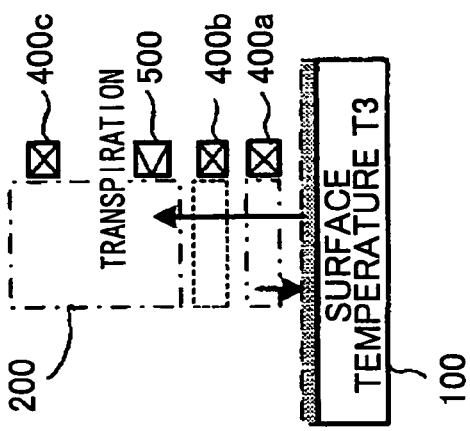
FIGS. 27A, 27B, 27C are diagrams of a first example of a measurement unit according to the present invention.
Figure 27B:
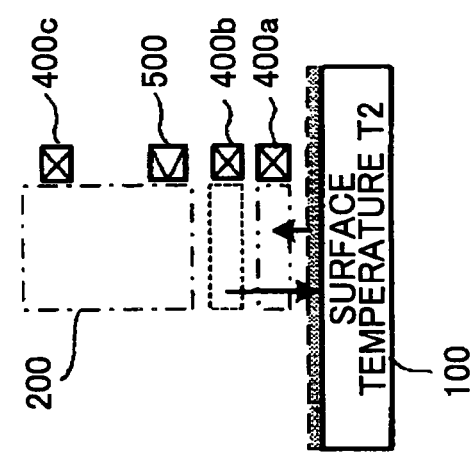
Figure 27C:
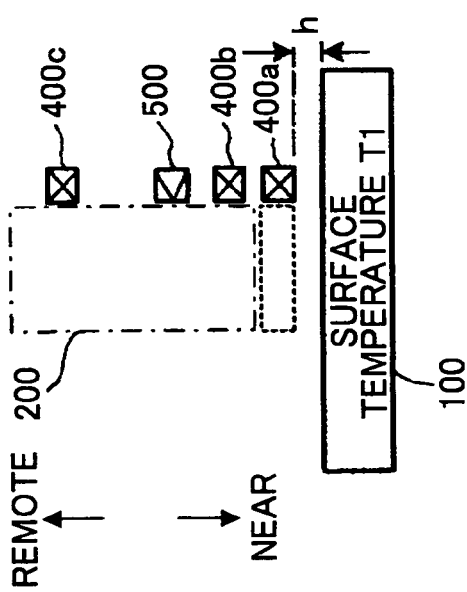

FIG. 26 is a block diagram of a non-contact condensation detecting apparatus 300 according to an embodiment of the present invention, configured to remotely detect dew condensation behavior and transpiration behavior on the surface of the object 100 in a non-contact manner. As shown in FIG. 26, the non-contact condensation detecting apparatus 300 includes plural humidity/temperature sensors 400a, 400b, 400c, a flowsensor 500, and a processing unit 600. FIGS. 27A, 27B, 27C are diagrams of a first example of a measurement unit according to the present invention. As shown in FIGS. 27A, 27B, 27C, the humidity/temperature sensor 400a is arranged near the surface of the object 100 and at a distance h from the surface of the object 100, and detects a temperature Ta and a humidity Ha of the atmosphere 200 near the surface of the object 100. The humidity/temperature sensor 400b is disposed in the middle of (in between) a location near the surface of the object 100 and a location remote from the surface of the object 100, and detects a temperature Tb and a humidity Hb of the atmosphere 200 in the middle location. The humidity/temperature sensor 400c is disposed remote from the surface of the object 100, and detects a temperature Tc and a humidity Hc of the atmosphere 200 remote from the surface of the object 100. The flowsensor 500 is arranged in the middle of a location near the surface of the object 100 and a location remote from the surface of the object 100, and detects a flow direction Fz and a flow velocity Wa of the atmosphere 200. Referring back to FIG. 26, the processing unit 600 includes an operations unit 700, a calculating unit 800, a storing unit 900, and an alarm output unit 1000. The calculating unit 800 receives the temperature, the flow direction, the flow velocity, etc., of the atmosphere 200 detected by the humidity/temperature sensors 400a, 400b, 400c and the flowsensor 500 at predetermined timings. The calculating unit 800 stores the received temperature, humidity, and flow direction into the storing unit 900, and determines dew condensation behavior and transpiration behavior on the surface of the object 100 based on changes in the received temperatures, humidity levels, and flow direction. The alarm output unit 1000 outputs a dew condensation alarm signal or a transpiration signal to a temperature/humidity control unit when a corresponding dew-concentration signal or transpiration signal is received from the calculating unit 800.

Figure 28:
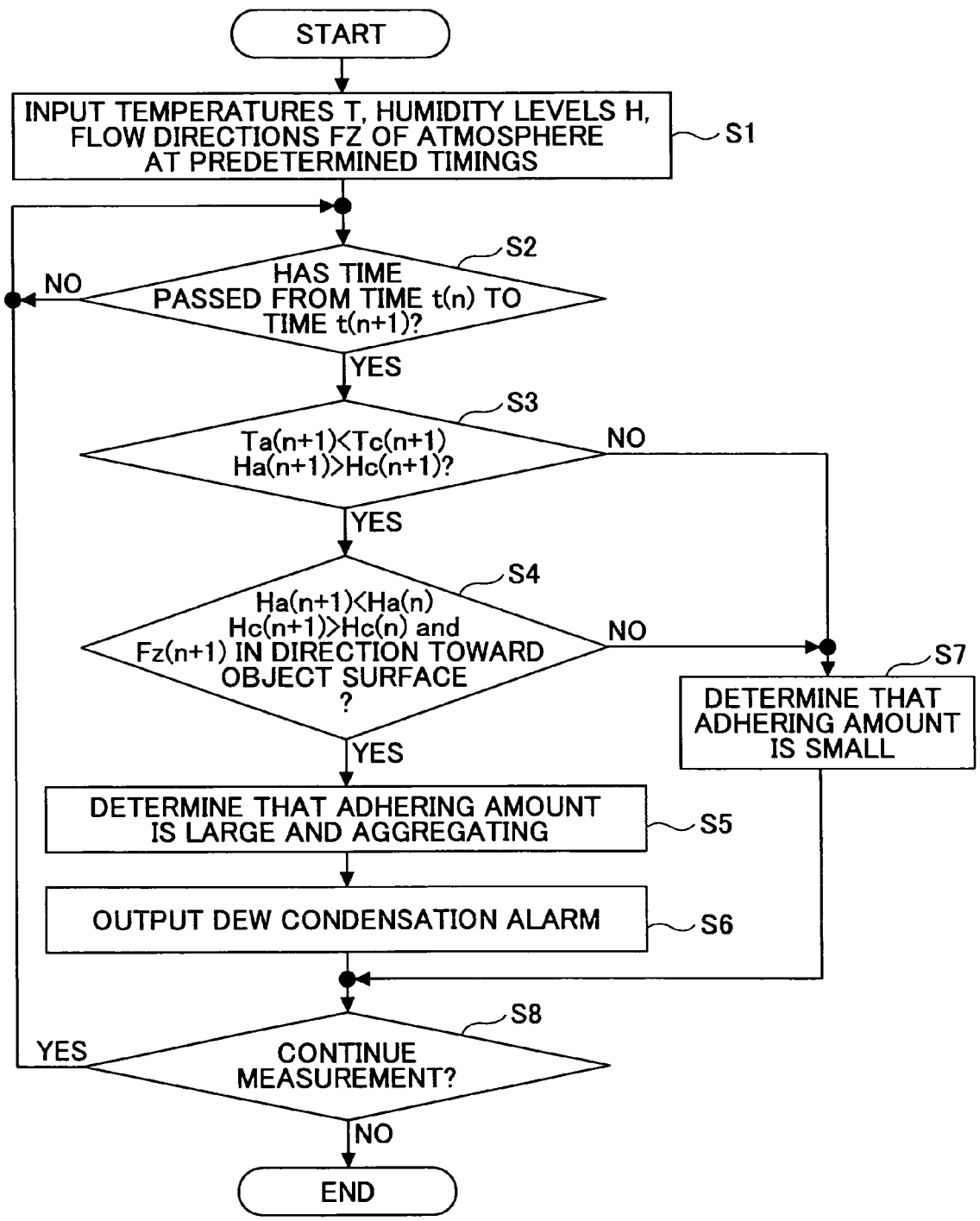
FIG. 28 is a flowchart of a process for detecting dew condensation on an object surface.

A process performed by the non-contact condensation detecting apparatus 300 for detecting dew condensation on the surface of the object 100 is described with reference to a flowchart in FIG. 28, and FIGS. 27A, 27B.

The calculating unit 800 in the processing unit 600 receives temperatures T, humidity levels H, and flow directions Fz of the atmosphere 200 detected by the humidity/temperature sensors 400a, 400b, 400c and the flowsensor 500 at predetermined timings. The calculating unit 800 stores the received temperatures T, the humidity levels H, and the flow directions Fz in the storing unit 900 (step S1). Then, when time passes from a time t(n) to a time t(n+1) (step S2), the calculating unit 800 compares a nearby temperature Ta(n+1) received from the humidity/temperature sensor 400a with a remote temperature Tc(n+1) received from the humidity/temperature sensor 400c, and compares a nearby humidity Ha(n+1) received from the humidity/temperature sensor 400a with a remote humidity Hc(n+1) received from the humidity/temperature sensor 400c, at the time t(n+1) (step S3). When the nearby temperature Ta(n+1) and the remote temperature Tc(n+1) are the same as shown in FIG. 27A (No in step S3), the calculating unit 800 determines that the temperature T1 of the surface of the object 100 and the remote temperature Tc(n+1) are the same, and that the amount of water vapor molecules of the atmosphere adhering on the surface of the object 100 is small (step S7). When the nearby temperature Ta(n+1) received from the humidity/temperature sensor 400a is lower than the remote temperature Tc(n+1) received from the humidity/temperature sensor 400c, and the nearby humidity Ha(n+1) received from the humidity/temperature sensor 400a is higher than the remote humidity Hc(n+1) received from the humidity/temperature sensor 400c (Yes in step S3), the calculating unit 800 determines that there is a possibility that water vapor molecules of the atmosphere 200 will adhere on the surface of the object 100. The calculating unit 800 compares the humidity levels received from the humidity/temperature sensor 400a and the humidity/temperature sensor 400c at the time t(n+1) with those previously received at the time t(n) (step S4). When the nearby humidity Ha(n+1) received at the time t(n+1) is lower than a nearby humidity Ha(n) received at the time t(n) from the humidity/temperature sensor 400a, the remote humidity Hc(n+1) received at the time t(n+1) is higher than a remote humidity Hc(n) received at the time t(n) from the humidity/temperature sensor 400c, and the flow direction Fz of the atmosphere 200 at the time t(n+1) received from the flow sensor 5 is directed toward the surface of the object 100 as shown in FIG. 27B (Yes in step S4), the calculating unit 800 determines that a large amount of water vapor molecules of the atmosphere 200 will adhere and aggregate on the surface of the object 100. The calculating unit 800 outputs to the alarm output unit 1000 a dew condensation signal, indicating that there is a possibility of dew condensation on the surface of the object 100 (step S5). When the dew condensation signal is received from the calculating unit 800, the alarm output unit 1000 outputs a dew condensation alarm signal to the temperature/humidity control unit, such as a dehumidifier (step S6). When it is found from comparing the humidity levels received from the humidity/temperature sensor 400a and the humidity/temperature sensor 400c at the time t(n+1) with those previously received at the time t(n), that the nearby humidity Ha(n+1) received at the time t(n+1) is equal to or higher than the nearby humidity Ha(n) received at the time t(n), the remote humidity Hc(n+1) received at the time t(n+1) is equal to or higher than the remote humidity Hc(n) received at the time t(n), and the flow direction Fz of the atmosphere 200 at the time t(n+1) received from the flow sensor 5 is directed away from the surface of the object 100 (No in step S4), the calculating unit 800 determines that the amount of water vapor molecules of the atmosphere 200 adhering the surface of the object 100 is small (step S7). This process is repeated while measurement is continued (step S8, S2).

Figure 29:
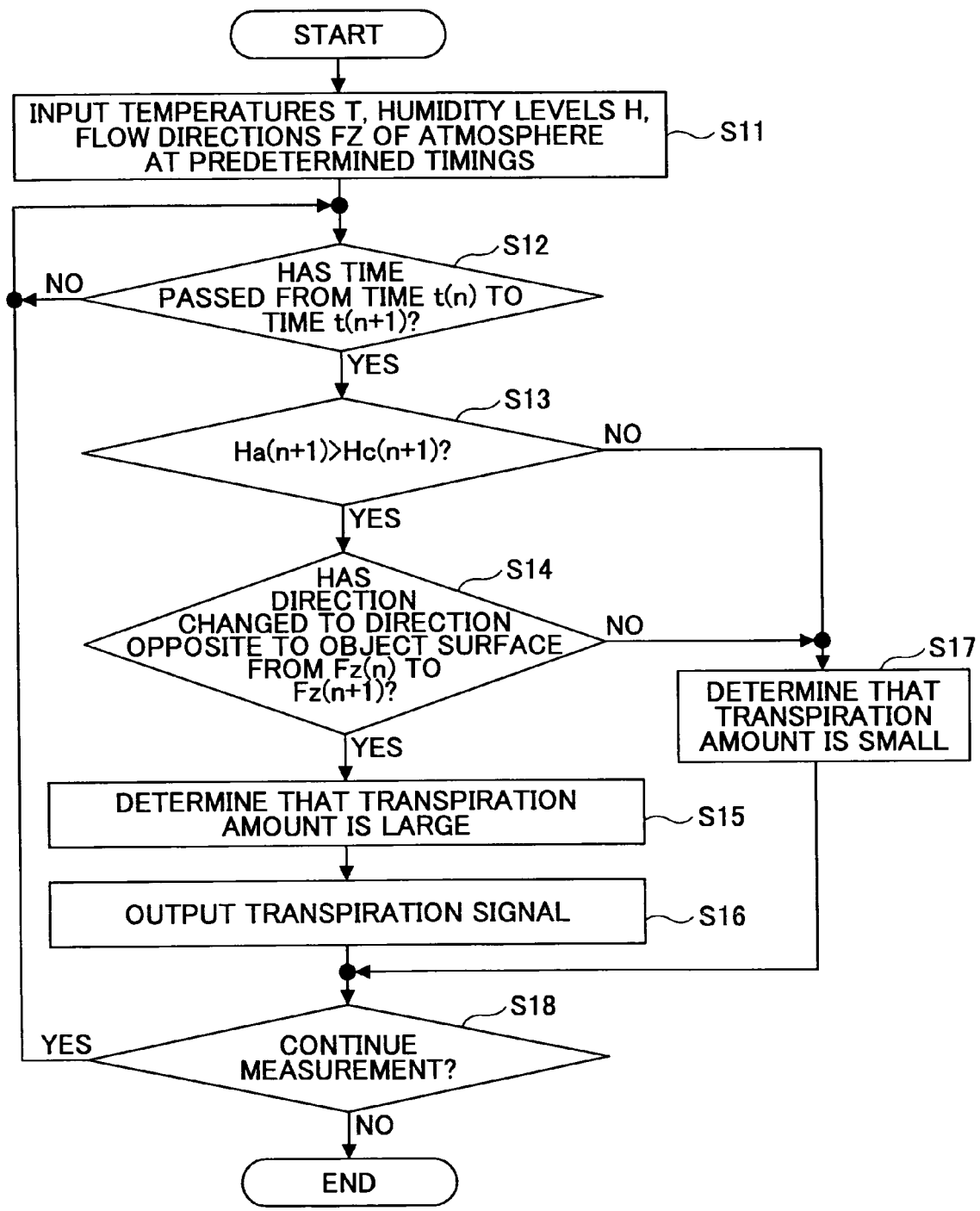
FIG. 29 is a flowchart of a process for detecting transpiration from an object surface.

A process performed by the non-contact condensation detecting apparatus 300 for detecting transpiration from the surface of the object 100 is described with reference to a flowchart in FIG. 29 and FIG. 27C.

The calculating unit 800 receives temperatures T, humidity levels H, and flow directions Fz of the atmosphere 200 detected by the humidity/temperature sensors 400a, 400b, 400c and the flowsensor 500 at predetermined timings. The calculating unit 800 stores the received temperatures T, the humidity levels H, and the flow directions Fz in the storing unit 900 (step S11). Then, when time passes from a time t(n) to a time t(n+1) (step S12), the calculating unit 800 compares a nearby humidity Ha(n+1) received from the humidity/temperature sensor 400a with a remote humidity Hc(n+1) received from the humidity/temperature sensor 400c, at the time t(n+1) (step S13). When the nearby humidity Ha(n+1) is lower than the remote humidity Hc(n+1) (No in step S13), the calculating unit 800 determines that there is substantially no transpiration from the surface of the object 100 (step S17). When the nearby humidity Ha(n+1) is higher than the remote humidity Hc(n+1) (Yes in step S13), the calculating unit 800 determines that there is a possibility that water vapor molecules are undergoing transpiration from the surface of the object 100. The calculating unit 800 determines whether the flow direction Fz of the atmosphere 200 received from the flowsensor 500 at the time t(n+1) has changed from the time t(n), and the flow direction Fz of the atmosphere 200 at the time t(n+1) is in an opposite direction to the surface of the object 100 (step S14). When the flow direction Fz of the atmosphere 200 at the time t(n+1) is in the opposite direction to the surface of the object 100 as shown in FIG. 27C (Yes in step S14), the calculating unit 800 determines that water vapor molecules are undergoing transpiration from the surface of the object 100 (step S15). The calculating unit 800 outputs to the alarm output unit 1000 a transpiration signal, indicating that water vapor molecules are undergoing transpiration from the surface of the object 100. When the transpiration signal is received from the calculating unit 800, the alarm output unit 1000 outputs a transpiration alarm signal to the temperature/humidity control unit, such as the dehumidifier (step S16). When the flow direction Fz of the atmosphere 200 at the time t(n+1) is not in the opposite direction to the surface of the object 100 (No in step S14), the calculating unit 800 determines that there is substantially no transpiration from the surface of the object 100 (step S17). This process is repeated while measurement is continued (step S18, S12).

As described above, a dew condensation behavior and a transpiration behavior on the surface of the object 100 can be detected from a location remote from the surface of the object 100 in a non-contact manner by measuring changes in the temperature gradient, the humidity gradient, and the flow of the atmosphere 200 with respect to the surface of the object 100.

Figure 30A:
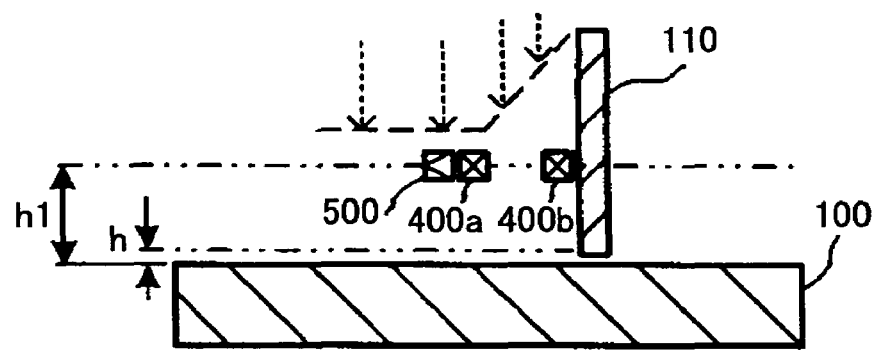
FIGS. 30A, 30B are diagrams of a second example of a measurement unit.
Figure 30B:
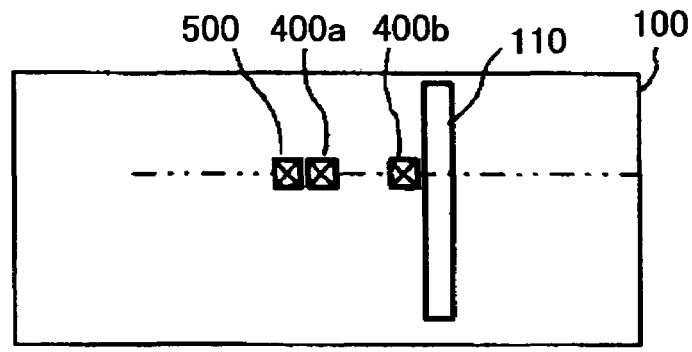

FIGS. 30A, 30B are diagrams of a second example of a measurement unit. In the above description, the humidity/ temperature sensors 400a, 400b, 400c and the flowsensor 500 are arranged in a perpendicular direction with respect to the surface of the object 100. However, as shown in FIGS. 30A, 30B, a wall 110 can be disposed perpendicular to the surface of the object 100, at a distance h from the surface of the object 100. The humidity/temperature sensors 400a, 400b and the flowsensor 500 can be disposed at a distance h1 from the surface of the object 100, corresponding to the middle of the wall 110. The humidity/temperature sensor 400a and the flowsensor 500 can be disposed remotely from the wall 110, and the humidity/temperature sensor 400b can be disposed near the wall 110. When the humidity/temperature sensors 400a, 400b, 400c and the flowsensor 500 are arranged in a perpendicular direction with respect to the surface of the object 100 the humidity/temperature sensor 400a located near the surface of the object 100 is affected by the surface of the object 100 at an early stage, while the humidity/temperature sensor 400c located remote from the surface of the object 100 is affected by the surface of the object 100 at a later stage than the humidity/temperature sensor 400a. Considering this behavior, as shown in FIGS. 30A, 30B, the wall 110 is disposed, and the humidity/temperature sensor 400a and the flowsensor 500 are disposed at the same distance h1 from the surface of the object 100, so that the sensors are affected by the object 100 at different timings.

The wall 110 provides a transportation friction resistance on gas with respect to the surface of the object 100. Specifically, a thickness δ of a boundary layer at which the laminar flow velocity receives friction resistance of the wall 110 can be obtained with the following formula according to Stokes' law, where a distance from the top edge (as viewed in FIG. 30A) of the wall 110 along the wall 110 is x, the flow velocity is U, and the friction resistance of the wall 110 is v:

$$\delta \approx 5*(vx/U)^{1/2}$$

Figure 31:
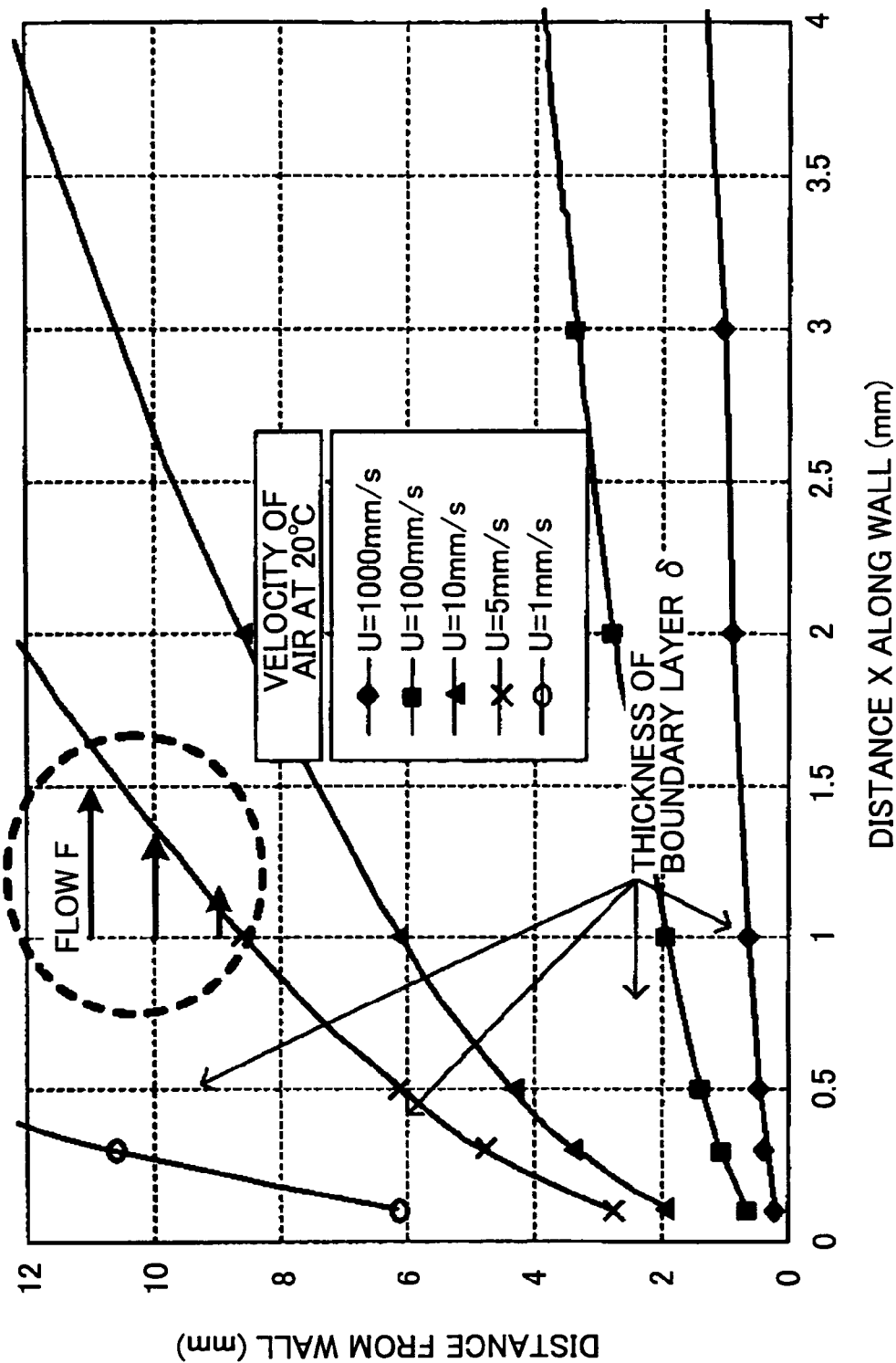
FIG. 31 is a graph indicating changes in the thickness of a boundary layer with respect to the distance along a wall.

FIG. 31 is a graph indicating changes in the thickness of the boundary layer δ with respect to the distance x from the top edge of the wall 110 along the wall 110, at the flow velocities U of 1 mm/sec, 5 mm/sec, 10 mm/sec, 100 mm/sec, and 1000 mm/sec, in an air temperature of 20° C. A flow at the flow velocity of U=5 mm/sec moves 0.5 mm in 0.1 second. However, due to the friction resistance from the wall 110, this flow moves as indicated by flow F in the dashed-line circle in FIG. 31. The flow F represents the flow at a point where the distance from the wall edge is x=1 mm, as the distance away from the wall 110 becomes 9 mm, 10 mm, and 11 mm.

As the humidity/temperature sensor 400a and the flowsensor 500 are disposed distant from the wall 110, and the humidity/temperature sensor 400b is disposed near the wall 110, the atmosphere 200 detected by the humidity/temperature sensor 400a at a certain time t is further away from the wall 110 than that detected by the humidity/temperature sensor 400b. As shown in FIG. 30A, the flow reaches the humidity/temperature sensor 400a before the humidity/temperature sensor 400b. Specifically, at the time t, the humidity/temperature sensor 400b is closer to the wall 110, where the flow decelerates due to the friction resistance and thus reaches the surface of the object 100 at a delayed time. This means that the humidity/temperature sensor 400b detects the atmosphere 200 under the same conditions as detecting the atmosphere 200 at a remote location. Accordingly, a dew condensation behavior and a transpiration behavior on the surface of the object 100 can be detected from a location remote from the surface of the object 100 by measuring changes in the temperature gradient, the humidity gradient, and the flow of the atmosphere 200 with respect to the surface of the object 100, according to the atmosphere temperatures Ta, Tb detected by the humidity/temperature sensors 400a, 400b and the flow direction Fz detected by the flowsensor 500.

To achieve detection resolution, the distance of a path of gas that is transported in association with absorption and aggregation on the surface of the object 100 needs to be made long. If the humidity/temperature sensors are arranged along such a long path, the overall size of the measurement unit becomes large. However, as shown in FIGS. 30A, 30B, by disposing the wall 110 perpendicular to the surface of the object 100, and disposing the humidity/temperature sensors 400a, 400b and the flowsensor 500 at the distance h1 from the surface of the object 100, corresponding to the middle of the wall 110, the measurement unit can be made compact.

Depending on the gas transportation mechanism, the status of the atmosphere may change at a moderate gradient according to the transportation velocity. In this case it is difficult to perform measurements. However, as shown in FIGS. 30A, 30B, by arranging the wall 110 that provides a transportation friction resistance on gas with respect to the surface of the object 100, the atmosphere 200 can be made to change at a steep gradient.

Elements of gas forming the atmosphere 200 may cause a density gradient within a minute space according to the distance from the surface of the object 100. Examples of the elements include a temperature gradient, viscosity, density, heat conductivity, gravity, and vapor pressure. Accordingly, a remote location from the surface of the object 100 is less influenced by the surface of the object 100 and more influenced by fluctuations in the surrounding environment. If the humidity/temperature sensors 400a, 400b are disposed at a remote location from the surface of the object 100, the measurements are affected by these fluctuations. However, as shown in FIGS. 30A, 30B, by disposing the wall 110 perpendicular to the surface of the object 100, and disposing the humidity/temperature sensors 400a, 400b and the flowsensor 500 at the distance h1 from the surface of the object 100, the measurement unit is made compact, and measurements can be less influenced by fluctuations in the surrounding environment.

In order to prevent the wall 110, which has friction resistance, the humidity/temperature sensors 400a, 400b, and the flowsensor 500 from affecting the thermal status of the atmosphere 200, these components are preferably made of a material of extremely small heat capacity or of similar heat conductivity to that of the atmosphere 200.

Figure 32A:
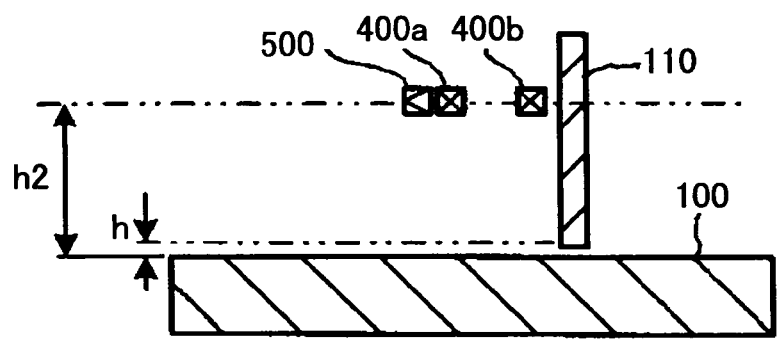
FIGS. 32A, 32B are diagrams of a third example of a measurement unit.
Figure 32B:
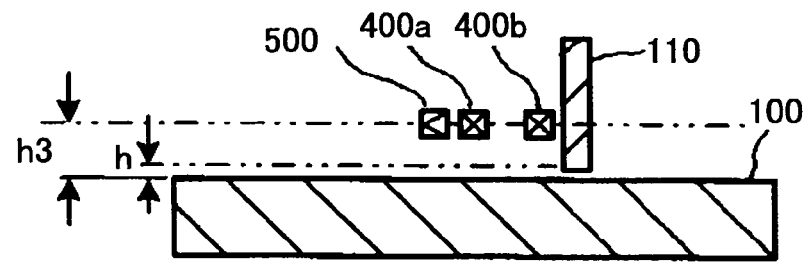

In FIGS. 30A, 30B, the humidity/temperature sensors 400a, 400b and the flowsensor 500 are disposed at a location corresponding to the middle of the wall 110. However, as shown in a third example of a measurement unit in FIG. 32A, the humidity/temperature sensors 400a, 400b and the flowsensor 500 can be disposed near the top edge of the wall 110, opposite to the surface of the object 100. Alternatively, as shown in FIG. 32B, the humidity/temperature sensors 400a, 400b and the flowsensor 500 can be disposed near the surface of the object 100. In the configuration shown in FIG. 32A, in which the humidity/temperature sensors 400a, 400b and the flowsensor 500 are disposed near the top edge of the wall 110 opposite to the surface of the object 100, as the distance x from the top edge of the wall 110 along the wall 110 becomes closer to 0, the boundary layer becomes close to the wall 110 even if the flow velocity range is large, so that the thickness δ of the boundary layer is narrow. Accordingly, the humidity/temperature sensors 400a, 400b and the flowsensor 500 can be disposed near the wall 110, the measurement unit is made even more compact, and measurements can be performed for a wide flow velocity range. In the configuration shown in FIG. 32B, because the humidity/temperature sensors 400a, 400b and the flowsensor 500 are disposed near the surface of the object 100, the length of the wall 110 can be made short. This facilitates measurement of flows of the atmosphere 200 flowing in opposite directions for aggregation and transpiration.

Figure 33A:
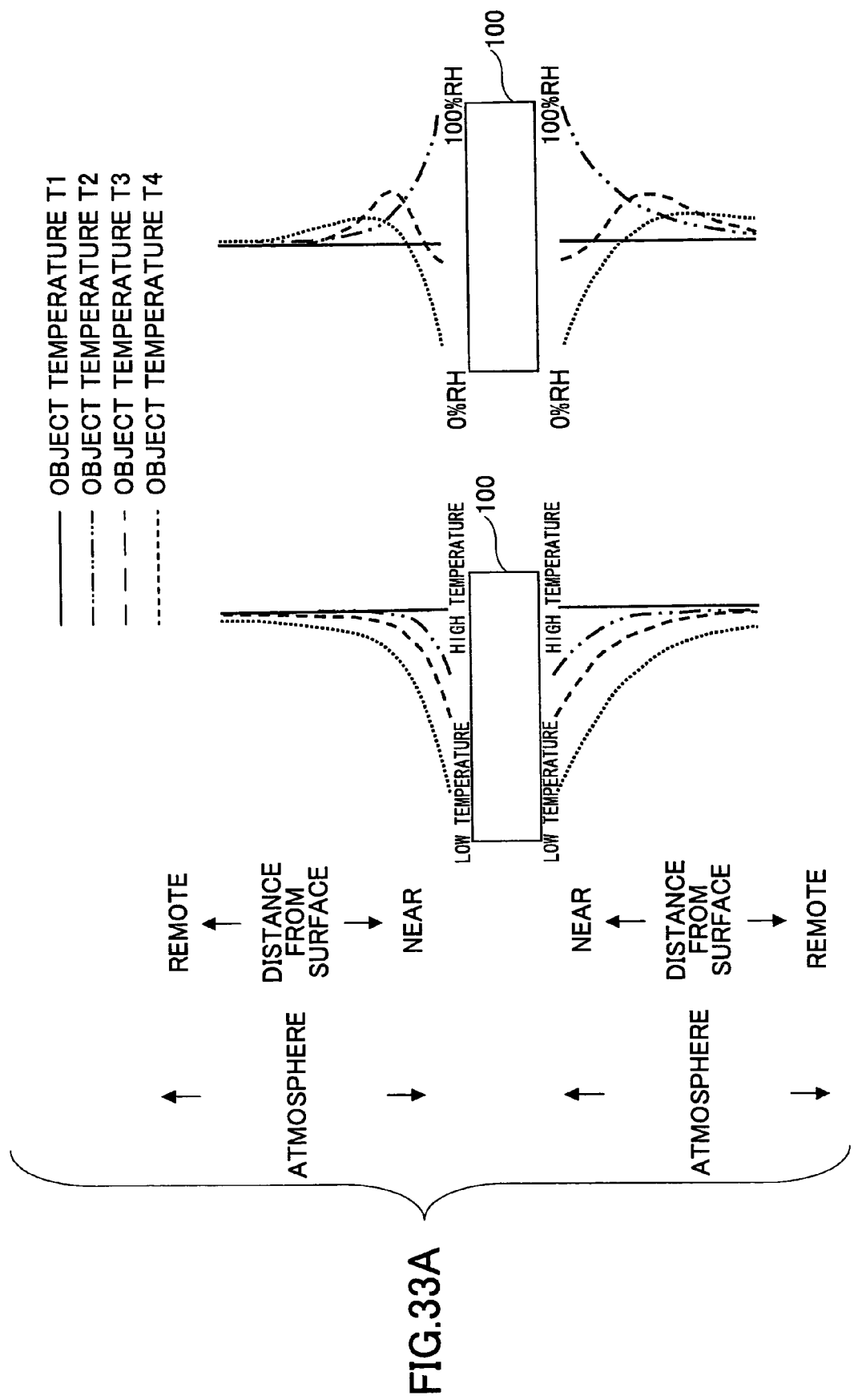

The atmosphere 200 at the surface of the object 100 increases in specific gravity as the temperature decreases, and the atmosphere 200 descends more easily than rising due to gravity. The temperature gradient changes accordingly. On the other hand, the higher the temperature and the lower the humidity, the specific gravity of the atmosphere 200 becomes small and light. According to temperature conditions at the surface of the object 100, the distributions of temperature and humidity of the atmosphere 200 with respect to the distance from the surface of the object 100 are different between the upper surface and the lower surface of the object 100. FIG. 33A provides distribution charts of the temperature and the humidity of the atmosphere 200 at the upper surface and the lower surface of the object 100. At the upper surface, when the temperature at the surface of the object 100 is lower than the temperature of the atmosphere 200, the atmosphere 200 near the object 100 is cooled by the surface of the object 100, increases in specific gravity, and thus descends due to gravity. Accordingly, the distance at which the atmosphere 200 is influenced by the heat from the surface of the object 100 becomes short. At the lower surface, when the temperature at the surface of the object 100 is lower than the temperature of the atmosphere 200, the atmosphere 200 near the object 100 is cooled by the surface of the object 100, increases in specific gravity, and thus descends due to gravity. Accordingly, the distance at which the atmosphere 200 is influenced by the heat from the surface of the object 100 becomes long. If the transportation velocity of the gas transported in association with absorption and aggregation on the surface of the object 100 is extremely low, the atmosphere 200 may be more affected by fluctuations of the surrounding environment. To eliminate influences of fluctuations of the surrounding environment, the difference in dew condensation behavior between the upper surface and the lower surface is obtained, as shown in FIG. 33B. Specifically, measurements are made under conditions where fluctuations of the surrounding environment, the surface condition, the specific heat, the capacity, and the dew condensation phenomenon are substantially the same for both surfaces of the object 100.

As shown in a fourth example of a measurement unit in FIG. 34A, the humidity/temperature sensors 400a, 400b and the flowsensor 500 are arranged above the object 100, and humidity/temperature sensors 410a, 410b and a flowsensor 510 are arranged below the object 100. This measurement unit detects behavior of the gas adhering and aggregating on the surface of the object 100, and behavior of the aggregated liquid transpiring, based on the difference in measured values between the upper surface and the lower surface of the object 100. Accordingly, influences of fluctuations of the surrounding environment can be eliminated.

The flow direction Fz of the atmosphere can be detected by the flowsensor 500 disposed above the object 100. Therefore, as shown in FIG. 34B, it is possible to dispose the flowsensor 500 only on one side of the object, for example the upper side. Moreover, even if the measurement unit is tilted as shown in FIG. 34C, influences of fluctuations of the surrounding environment can be eliminated by transporting the atmosphere 200 along the direction of gravity. The distance of gas transportation is longer at the lower surface than the upper surface of the object 100 due to gravity, and therefore, the measurement interval is longer, resulting in high sensitivity. Thus, even if the transportation velocity is extremely low, depending on the fluctuation of the surrounding environment, the dew condensation behavior can be detected from only the lower surface.

Figure 35A:
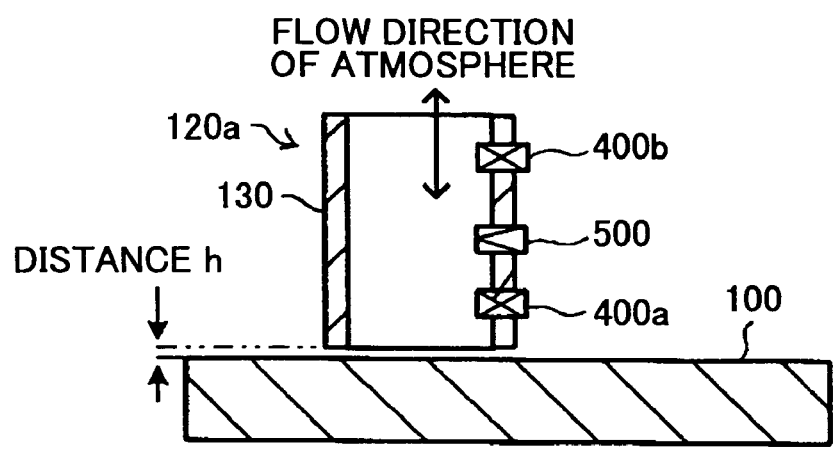
FIGS. 35A, 35B are diagrams of fifth and sixth examples of a measurement unit.
Figure 35B:
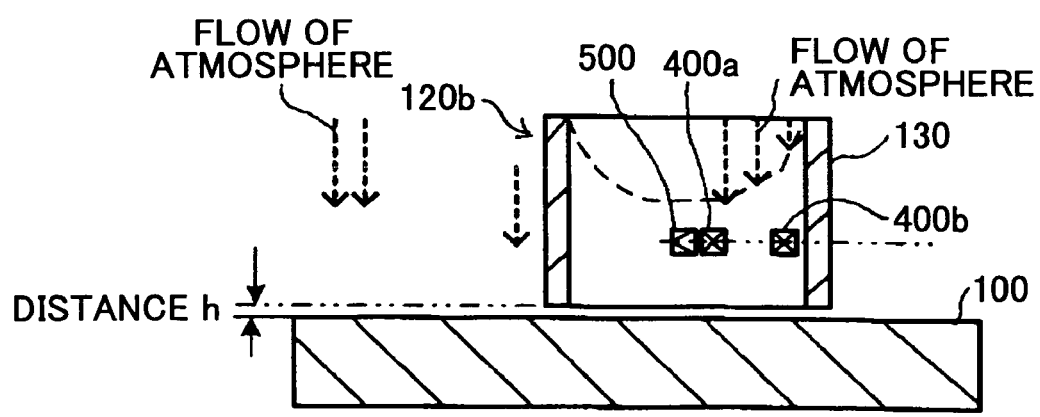

In measurement units 120a, 120b according to fifth and sixth examples, respectively, the humidity/temperature sensors 400a, 400b and the flowsensor 500 are disposed so as to be unaffected by fluctuations of the surrounding environment, and eliminate disturbances. As shown in FIGS. 35A, 35B, the humidity/temperature sensors 400a, 400b and the flowsensor 500 are disposed in a flow path inside a cylindrical rectifying tube 130. The atmosphere 200 at the surface of the object 100 is isolated from the surrounding environment by the rectifying tube 130, so as to eliminate the influence of fluctuations of the surrounding environment and turbulences. In the measurement unit 120a shown in FIG. 35A, the humidity/temperature sensors 400a, 400b and the flowsensor 500 are disposed along the wall of the rectifying tube 130. In the measurement unit 120b shown in FIG. 35B, the humidity/temperature sensors 400a, 400b and the flowsensor 500 are disposed perpendicular to the wall of the rectifying tube 130. In the measurement unit 120b shown in FIG. 35B, the wall of the rectifying tube 130 makes the atmosphere 200 change at a steep gradient, similar to the wall 110 shown in FIGS. 30A, 30B. Also, the rectifying tube 130 eliminates the influence of fluctuations of the surrounding environment and turbulences. In order to prevent the rectifying tube 130 from affecting the thermal status of the atmosphere 200, the rectifying tube 130 is also preferably made of a material of small heat capacity or of similar heat conductivity to that of the atmosphere 200, such as resin or ceramic.

Figure 36A:
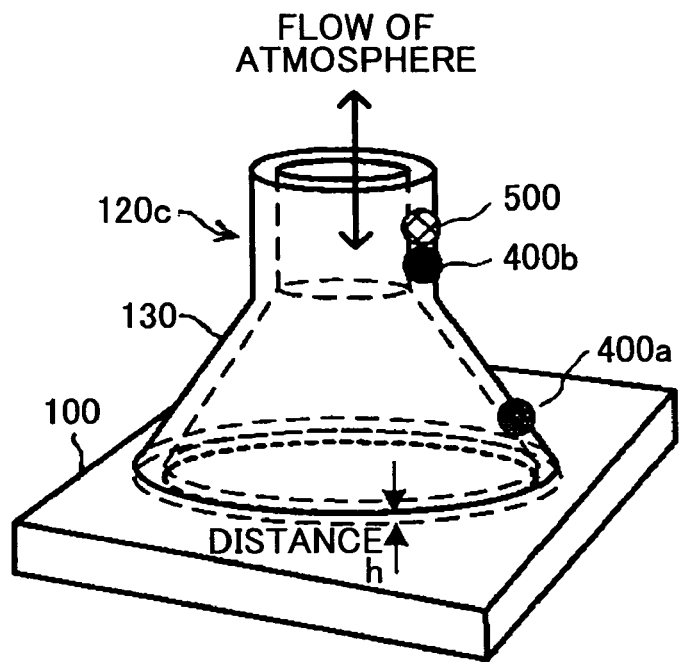
FIGS. 36A, 36B are diagrams of a seventh example of a measurement unit.
Figure 36B:
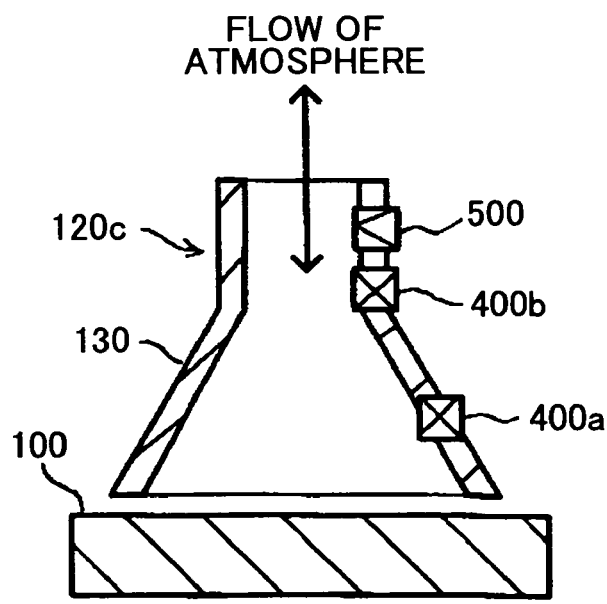

If the flow velocity of the atmosphere 200 on the surface of the object 100 is extremely small, the values measured by the humidity/temperature sensors 400a, 400b and the flowsensor 500 that detect the conditions of the atmosphere 200 flowing in the rectifying tube 130 need to be extracted to a greater degree. A seventh example of a measurement unit 120c addresses this aspect. FIG. 36A is a perspective view and FIG. 36B is a cross-sectional schematic diagram of the seventh example of the measurement unit. As shown in the figures, the cross-sectional area of the rectifying tube 130 is smaller on the side away from the surface of the object 100, than on the side near the surface of the object 100, so as to increase the flow velocity. This increases the accuracy of measurements performed by the humidity/temperature sensors 400a, 400b and the flowsensor 500 disposed in this area.

Sensors capable of quickly detecting the process of gas transportation, having fine spatial resolution, are preferably employed as the humidity/temperature sensors 400a, 400b and the flowsensor 500, for measuring changes in the temperature gradient, the humidity gradient, and the flow of the atmosphere 200 with respect to the surface of the object 100. The sensors having resistive elements of fine structures formed of thin films are recommended, such as those disclosed in U.S. Pat. No. 5,551,283 or Japanese Patent Nos. 2889909, 2621982, 2780911, or Japanese Laid-Open Patent Application No. H6-18465.

Figure 37A:
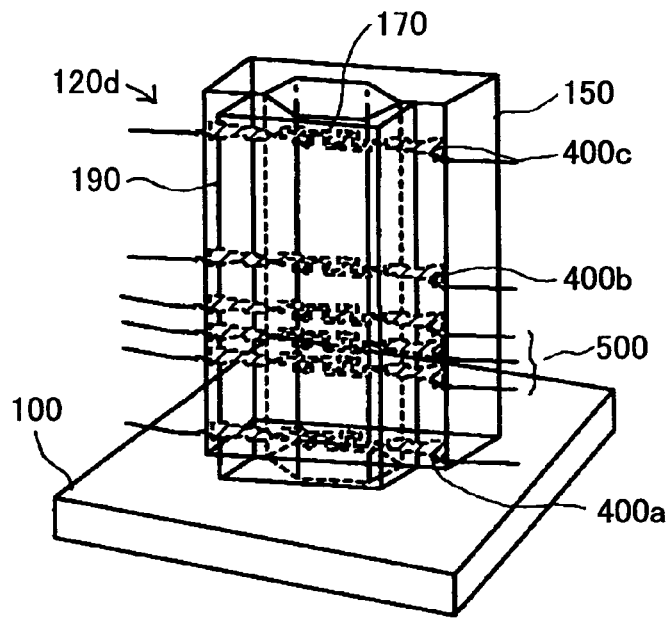
FIGS. 37A, 37B, 37C are diagrams of an eighth example of a measurement unit.
Figure 37B:
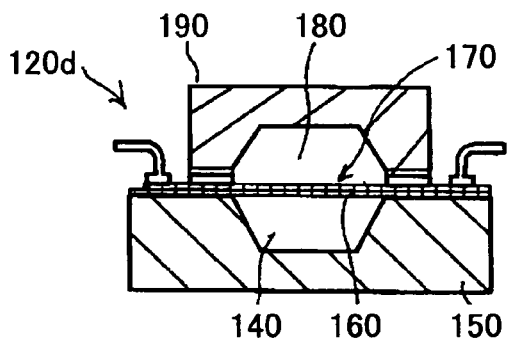
Figure 37C:
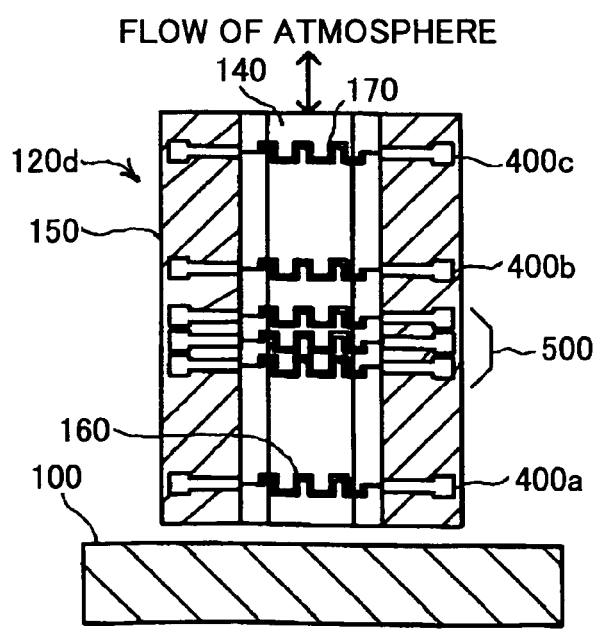

FIGS. 37A, 37B, 37C are diagrams of an eighth example of a measurement unit 120d. FIG. 37A is a perspective view, FIG. 37B is a cross-sectional schematic diagram of FIG. 37A in a horizontal plane direction, and FIG. 37C is a cross-sectional schematic diagram of FIG. 37A in a vertical plane direction. As shown in the measurement unit 120d in FIG. 37B, a groove 140 is located at the center of a substrate 150 in a vertical direction. Plural sensor sensing units 170 having a resistive element 160 of a fine structure formed of thin films are passed over the groove 140. A cover 190, having a groove 180 in the center thereof in a vertical direction, is connected onto the sensor sensing units 170. The substrate 150 and the cover 190 form the rectifying tube 130, with the groove 140 of the substrate 150 and the groove 180 of the cover 190 serving as flow paths. The substrate 150, the sensor sensing units 170, and the cover 190 can be easily fabricated by mass production with high precision, by using the so-called MEMS (Micro Electro Mechanical System) employing an integrated circuit fine-machining technology. The sensor sensing units 170 can be arrayed at different distances from the surface of the object 100, and can have different capabilities and functions. Therefore, with the measurement unit 120d, a wide range of temperature/humidity conditions and different speeds of dew condensation behaviors can be detected, the structure can be made compact, the external influence on the atmosphere 200 can be reduced, positional accuracy of measurement locations can be enhanced, and highly precise measurement values can be obtained. Moreover, installation locations are less limited, thereby improving versatility. Further, the same type of sensors that output signals of similar levels can be employed in the measurement unit 120d, so that processes performed by the processing unit 600 can simplified.

Figure 38A:
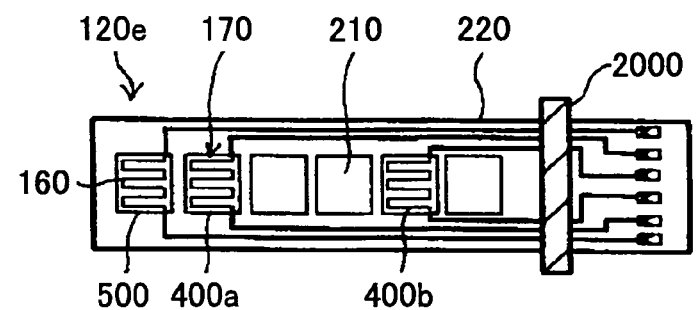
FIGS. 38A, 38B are diagrams of a ninth example of a measurement unit.
Figure 38B:
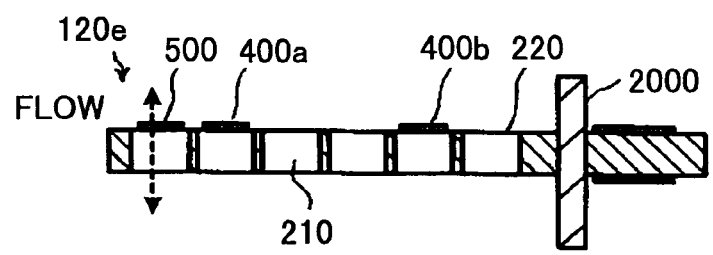

In the measurement unit 120c shown in FIGS. 37A, 37B, 37C, the humidity/temperature sensors 400a through 400c and the flowsensor 500 are disposed along the rectifying tube 130, i.e., along the grooves 140, 180 of the substrate 150 and the cover 190, respectively. However, when the humidity/temperature sensors 400a, 400b and the flowsensor 500 are disposed perpendicular to the wall of the rectifying tube 130, as shown in FIG. 35B, the humidity/temperature sensors 400a, 400b and the flowsensor 500 can have resistive elements of fine structures formed of thin films and can be formed integrally with the rectifying tube 130. FIGS. 38A, 38B are diagrams of a ninth example of a measurement unit 120e. FIG. 38A is a plan view and FIG. 38B is a cross-sectional schematic diagram. In the measurement unit 120e, a sensor substrate 220 is formed at the center of a wall 2000. The sensor substrate 220 has a constant cross-sectional area and includes plural through holes 210. Plural sensor sensing units 170 including resistive elements 160 are disposed on the through holes 210 of the sensor substrate 220, thereby forming the humidity/temperature sensors 400a, 400b and the flowsensor 500. As is described with reference to FIGS. 30A and 35B, the flowsensor 500 can be disposed distant from the wall 2000 that provides friction resistance to gas transportation, so as to enhance measurement sensitivity. For example, by disposing the sensor substrate 220 that is 1 mm wide, 5 mm long, and 0.5 mm thick, at the center of the wall 2000 that is 2 mm long; and disposing the humidity/temperature sensor 400b at a position 0.5 mm away from the wall 2000 and the humidity/temperature sensor 400a at a position 3 mm away from the wall 2000; the condition of the atmosphere flowing at 10 mm/sec to 100 mm/sec can be measured, according to the change of the thickness δ of the boundary layer in an air temperature of 20° C., as indicated in FIG. 31.

Figure 39A:
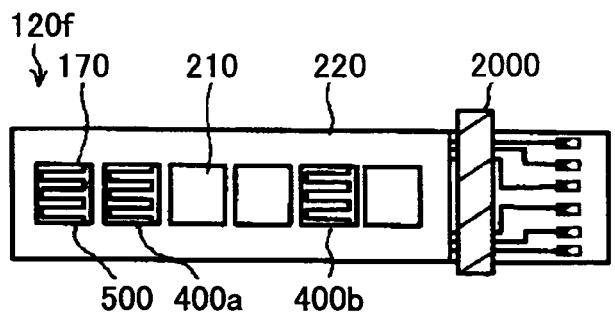
FIGS. 39A, 39B are diagrams of a tenth example of a measurement unit.
Figure 39B:
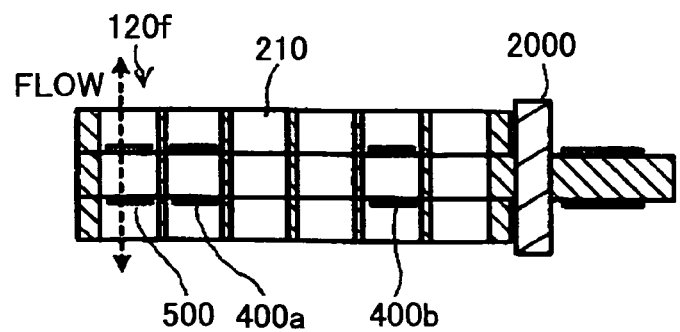

Moreover, plural measurement units 120d can be stacked, as shown a tenth example of a measurement unit 120f in FIGS. 39A, 39B. FIG. 39A is a plan view and FIG. 39B is a cross-sectional schematic diagram. With this configuration, the rectifying function can be further improved. Both the measurement unit 120e and the measurement unit 120f can be easily fabricated by MEMS employing an integrated circuit fine-machining technology.

In the description above, dew condensation occurs as water vapor molecules aggregate on the surface of the object 100. However, the technology according to the present invention can be applied to various fields, such as purification/separation of multicomponent gas. Specifically, a gas component sensor or a gas concentration sensor can be used instead of the humidity/temperature sensor to detect components, density, and concentration of gas.

Figure 40:
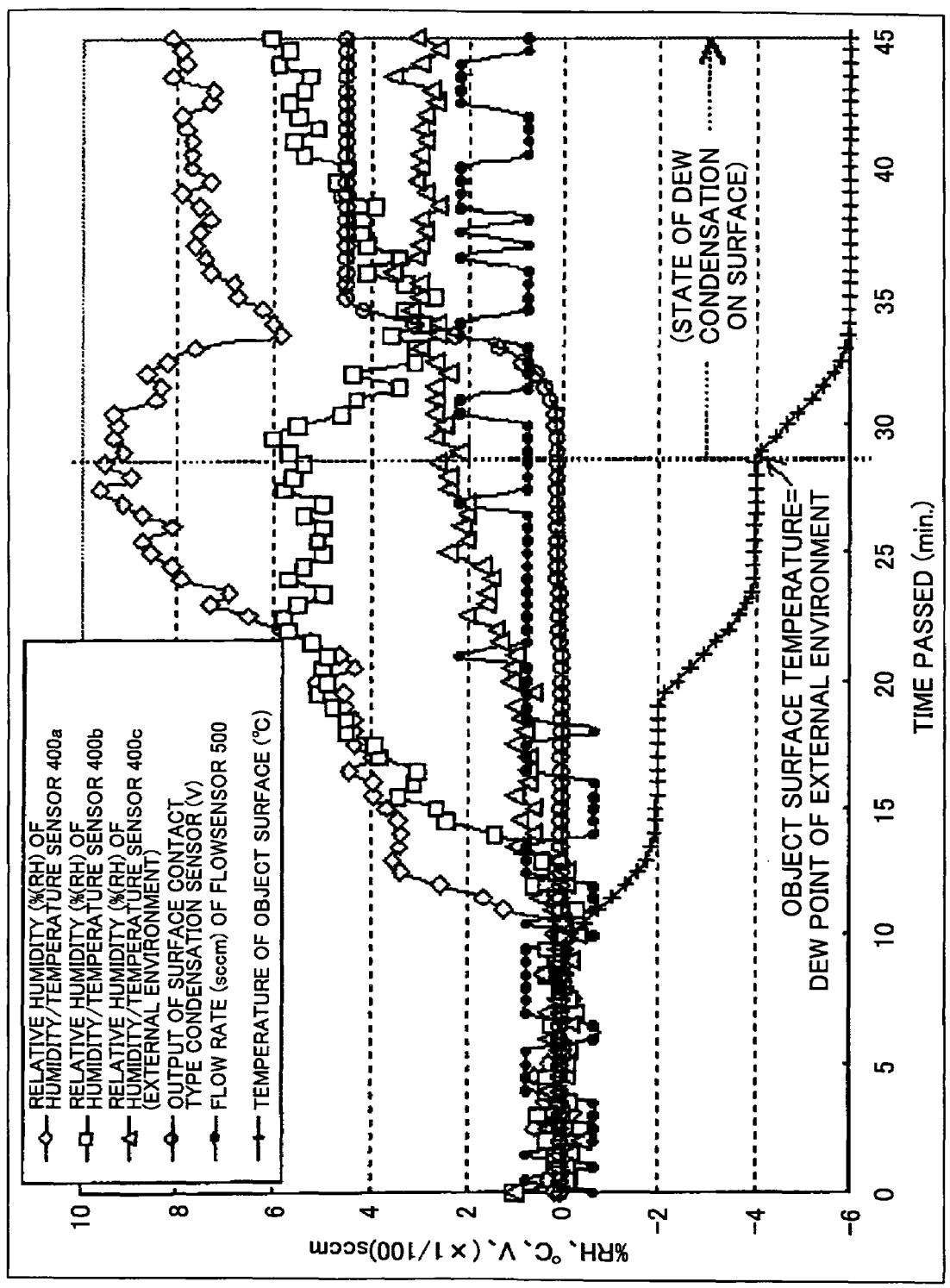
FIG. 40 is a variation property graph of temperature and humidity measured by the fifth example of the measurement unit.
Figure 41:
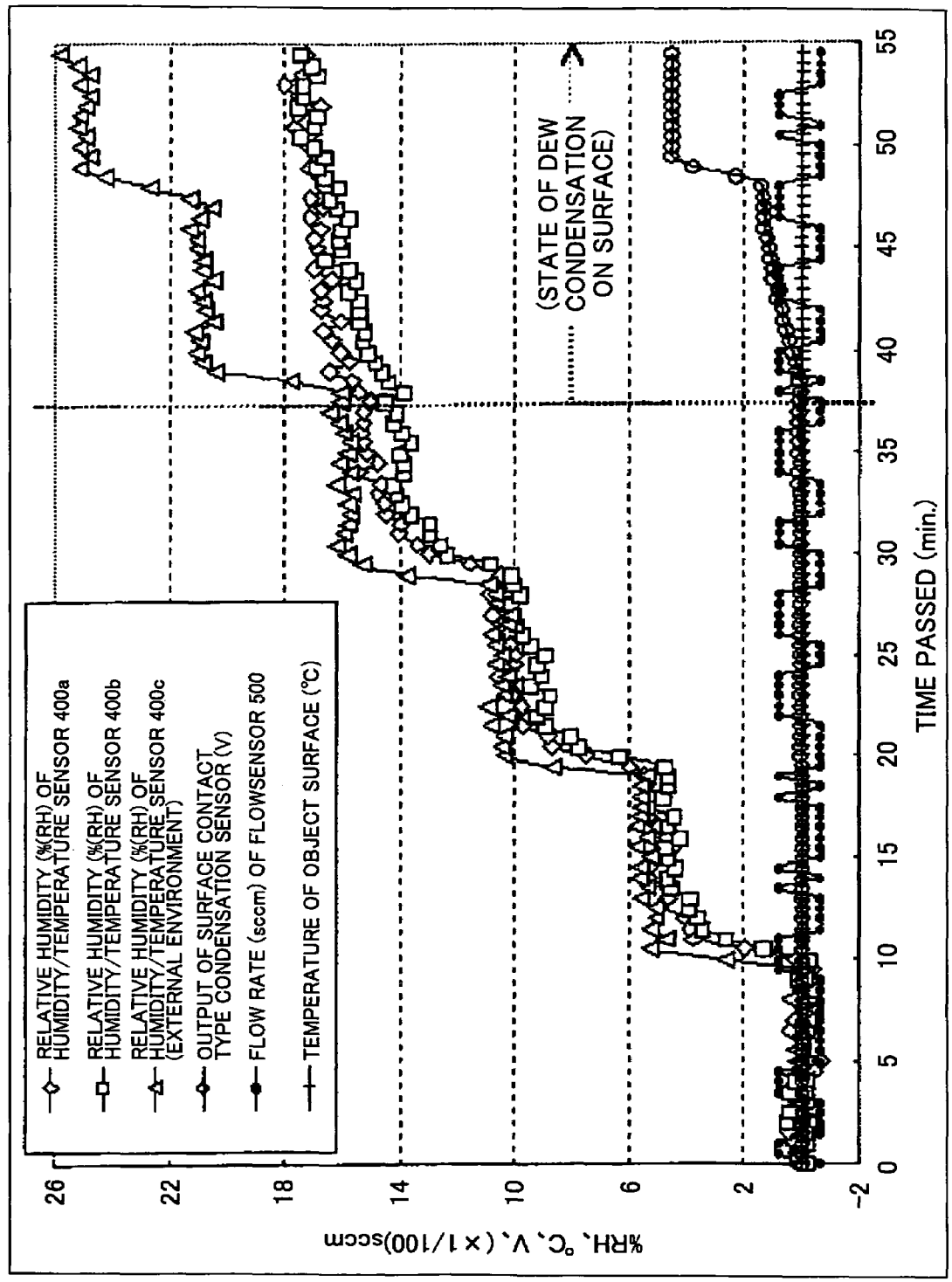
FIG. 41 is another variation property graph of temperature and humidity measured under a second condition, by the fifth example of the measurement unit.
Figure 42:
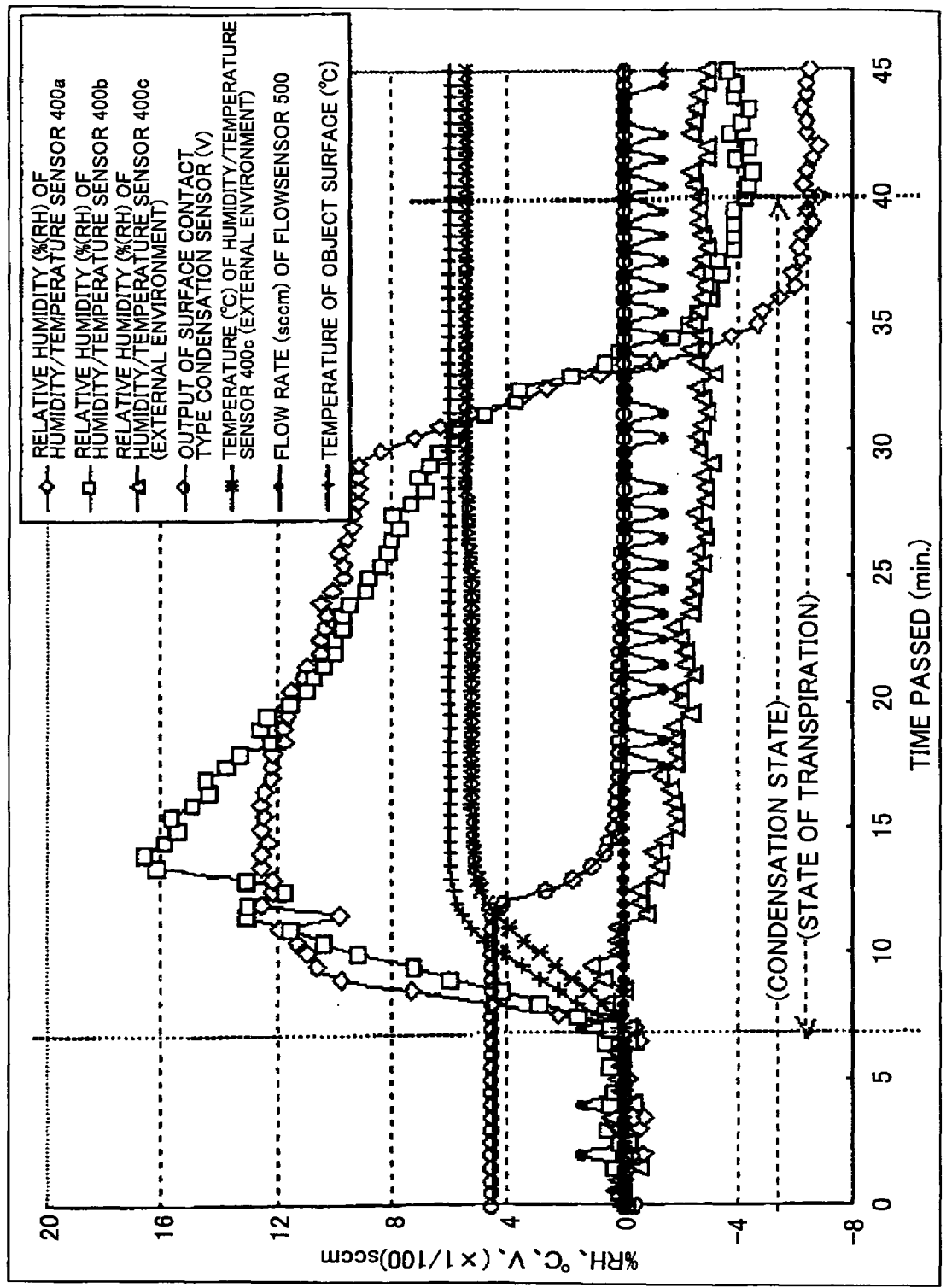
FIG. 42 is still another variation property graph of temperature and humidity measured under a third condition, by the fifth example of the measurement unit.

For example, the measurement unit 120a shown in FIGS. 35A, 35B was formed as follows. The rectifying tube 130 with an internal diameter of 11 mm and a length of 30 mm is made with acrylic resin. The rectifying tube 130 is spaced apart from the surface of the object 100 by 1 mm. The humidity/temperature sensor 400a is disposed at a position 2 mm from the bottom edge of the rectifying tube 130, the humidity/temperature sensor 400b is disposed at a position 15 mm from the bottom edge of the rectifying tube 130, the humidity/temperature sensor 400c is disposed at a position 28 mm from the bottom edge of the rectifying tube 130, and the flowsensor 500 is disposed in the middle of the humidity/temperature sensor 400a and the humidity/temperature sensor 400b. Measurements obtained by the measurement unit 120a thus formed are shown in FIGS. 40 to 42. By way of comparison in performance, a conventional measurement unit was also employed. Specifically, a surface contact-type condensation sensor, which detects changes in electric resistance values between electrodes caused by water adherence, was disposed on the surface of the object 100.

FIG. 40 is a variation property graph of temperature and humidity measured by the measurement unit 120a formed as above. The temperature of the surrounding environment of the rectifying tube 130 is fixed at 25° C., and the relative humidity is fixed at 80% RH (dew point=21.3° C.). After ten minutes, the temperature of the surface of the object 100 is gradually lowered from 25° C. by 2° C. at a time. After 28 minutes, the temperature of the surface of the object 100 is the same as the dew point 21.3° C. of the surrounding environment, and is to be further lowered. The humidity/temperature sensor 400a and the humidity/temperature sensor 400b are influenced by the temperature decline of the surface of the object 100. When the temperature of the surface of the object 100 exceeds the dew point of the surrounding environment, the temperature is decreased further and the relative humidity increases further in the surrounding environment. When the temperature of the surface of the object 100 is equal to or less than the dew point of the surrounding environment, the relative humidity is decreased in the surrounding environment. Moreover, the humidity/temperature sensor 400a is closer to the surface of the object 100 than the humidity/temperature sensor 400b, and therefore, when the temperature of the surface of the object 100 exceeds the dew point of the surrounding environment, the temperature decreases further and the relative humidity increases further in the surrounding environment, and when the temperature of the surface of the object 100 is equal to or less than the dew point of the surrounding environment, the relative humidity decreases further in the surrounding environment. The flowsensor 500 indicates that the flow towards the surface of the object 100 is increasing, based on the tendency around the dew point. Being located furthest from the surface of the object 100, the humidity/temperature sensor 400c is less affected by the temperature of the surface of the object 100, and more affected by the temperature of the surrounding environment.

Based on the behaviors of the humidity/temperature sensors 400*a*, 400*b*, 400*c* and the flowsensor 500, a dew condensation phenomenon can be observed. The humidity/temperature sensors 400*a*, 400*b* started reacting 29-30 minutes after dew condensation occurred on the surface of the object 100. This was faster than the surface contact-type condensation sensor, which started reacting after 32 minutes. Thus, response is quicker than the surface contact-type condensation sensor, detections can be performed in a non-contact manner, and a slight condensation behavior can be detected.

FIG. 41 is another variation property graph of temperature and humidity measured under a second condition, by the measurement unit 120*a* formed as above. The temperature of the surface of the object 100 is fixed at 20° C. Initially, the temperature is 25° C. and the relative humidity is 60% RH (dew point=16.7° C.) in the surrounding environment of the rectifying tube 130. After nine minutes, the relative humidity is gradually increased by 5% RH at a time, so that after 38 minutes, the dew point of the surrounding environment is 20° C., and is to be further increased. The humidity/temperature sensor 400*c* is distant from the surface of the object 100, and is therefore less affected by the surface of the object 100 and more affected by the humidity of the surrounding environment, and indicates that the relative humidity is increasing. The humidity/temperature sensors 400*a*, 400*b* are closer to the surface of the object 100, and are therefore more affected by the humidity near the surface of the object 100. Specifically, water vapor aggregates when dew condensation occurs on the surface of the object 100 as the dew point of the surrounding environment becomes equal to or greater than the temperature of the surface of the object 100, and water vapor density decreases. Accordingly, the relative humidity detected by the humidity/temperature sensors 400*a*, 400*b* does not increase as much as that detected by the humidity/temperature sensor 400*c*. Further, the flowsensor 500 indicates that the flow toward the surface of the object 100 is increasing, based on the tendency around the dew point.

Based on the behaviors of the humidity/temperature sensors 400*a*, 400*b*, 400*c* and the flowsensor 500, a dew condensation phenomenon can be observed. The humidity/temperature sensors 400*a*, 400*b* started to react 38 minutes after dew condensation occurred on the surface of the object 100. This was faster than the surface contact-type condensation sensor, which started reacting after 40 minutes. Thus, response is quicker than the surface contact-type condensation sensor, detections can be performed in a non-contact manner, and a slight condensation behavior can be detected.

FIG. 42 is still another variation property graph of temperature and humidity measured under a third condition, by the measurement unit 120*a* formed as above. The temperature of the surrounding environment of the rectifying tube 130 is fixed at 25° C., and the relative humidity is fixed at 80% RH (dew point=21.3° C.). The temperature of the surface of the object 100 is fixed at 19° C. Accordingly, dew condensation is made to occur. After seven minutes, the temperature of the surface of the object 100 is increased to 25° C., so that dew condensation water undergoes transpiration as water vapor.

When the temperature of the surface of the object 100 starts rising from 19° C. to 25° C., desorption of the water vapor is accelerated, the humidity/temperature sensors 400*a*, 400*b* indicate that the relative humidity is increasing, and transpiration is observed. The increase rate per time is higher at the humidity/temperature sensor 400*a*, as it is closer to the surface of the object 100 than the humidity/temperature sensor 400*b*. The flowsensor 500 indicates that the flow in the direction opposite to the surface of the object 100 is increasing, based on the tendency around the time that the temperature of the surface of the object 100 is increasing.

Based on the behaviors of the humidity/temperature sensors 400*a*, 400*b*, 400*c* and the flowsensor 500, a transpiration phenomenon can be observed. The humidity/temperature sensors 400*a*, 400*b* indicated increases in relative humidity for 40 minutes, indicated dew condensation, and indicated that the transpiration process continued for 33 minutes, between the time points of 7 minutes and 40 minutes after commencement of the experiment. As it is also clear from the behavior of humidity/temperature detected by the humidity/temperature sensor 400*c*, the temperatures detected by the humidity/temperature sensors 400*a*, 400*b* increase in association with the increase in the temperature of the surface of the object 100. Accordingly, the relative humidity decreased when the transpiration process ended, compared to when it started. The humidity/temperature sensors 400*a*, 400*b* started to react 8 minutes after transpiration from the surface of the object 100 occurred. This was faster than the surface contact-type condensation sensor, which started reacting after 12 minutes. The surface contact-type condensation sensor indicated after 12 minutes that dew condensation was eliminated; however, in reality, the dew condensation lasted for 40 minutes. Thus, response is quicker than the surface contact-type condensation sensor, detections can be performed in a non-contact manner, and a slight condensation behavior can be detected in real time.

The following is a description of an image forming apparatus employing the above-described non-contact condensation detecting apparatus 300 capable of detecting transpiration behavior of moisture in real time. This image forming apparatus detects the behavior of moisture undergoing transpiration from a recording sheet onto which an image is to be transferred, and prevents the recording sheet from curling when heat is applied at a heating unit.

Figure 43:
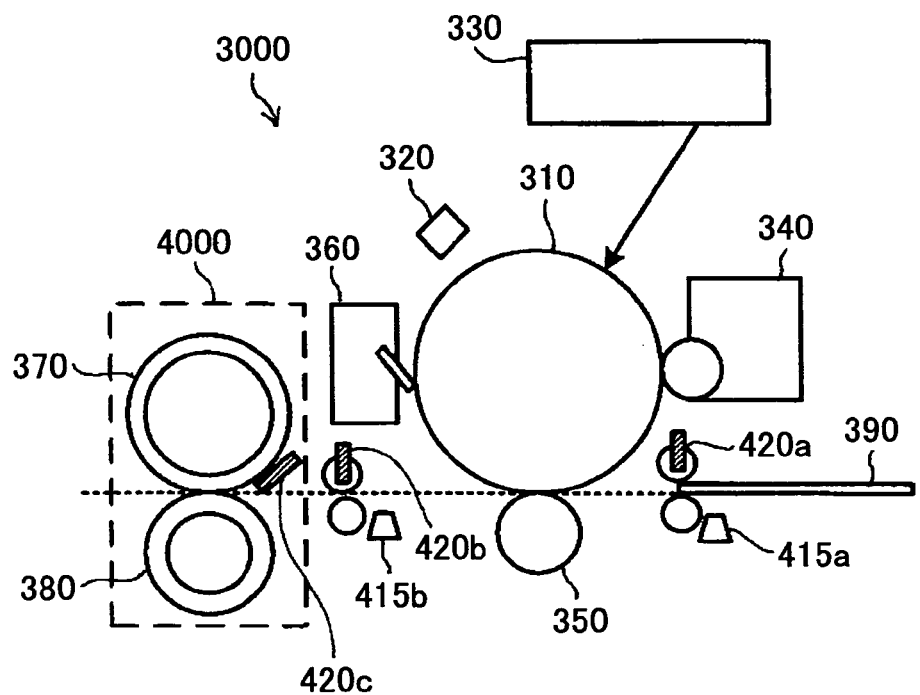
FIG. 43 is a schematic diagram of an image forming unit included in the image forming apparatus according to the present invention.

FIG. 43 is a schematic diagram of an image forming unit 3000 included in the image forming apparatus. A charging unit 320, a laser light source, and a polygon mirror, etc., are disposed around a photoconductive drum 310. The image forming unit 3000 further includes a writing unit 330 that writes an image by irradiating laser beams onto the image forming unit 3000, a developing unit 340, a transferring unit 350, a cleaning unit 360, a heating roller 370, a pressurizing roller 380, and a fixing unit 4000 that fixes a toner image transferred onto a recording sheet 390.

In the image forming unit 3000, the writing unit 330 irradiates a laser beam onto the surface of the photoconductive drum 310 that is charged by the charging unit 320, thereby forming an electrostatic latent image on the photoconductive drum 310. The developing unit 340 makes visible the electrostatic latent image by forming a toner image. The transferring unit 350 transfers the toner image formed on the photoconductive drum 310 onto the recording sheet 390 that is fed from a paper feeding unit or a manual feed tray. Toner remaining on the photoconductive drum 310 after the toner image is transferred onto the recording sheet 390 is removed by the cleaning unit 360. The recording sheet 390 onto which the toner image is transferred is conveyed to the fixing unit 4000. The fixing unit 4000 applies heat and pressure onto the recording sheet 390 so as to fix the toner image. The recording sheet 390 onto which the image is fixed is discharged from a discharging unit. When the fixing unit 4000 applies heat and pressure onto the recording sheet 390 to fix the toner image, the recording sheet 390 dries suddenly, and therefore curls. The speed at which the recording sheet 390 dries depends on the transpiration behavior of moisture included in the recording sheet 390.

Figure 44:
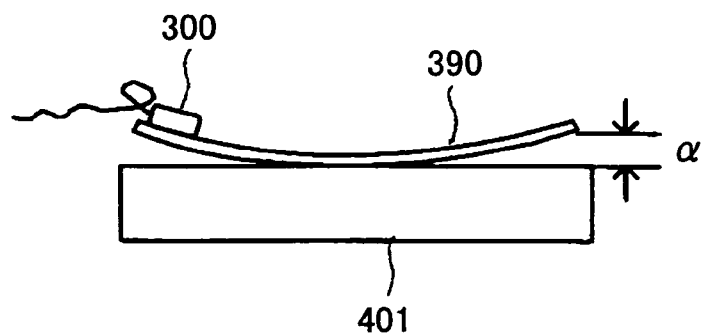
FIG. 44 is a schematic diagram of deformation caused by transpiration of moisture included in a recording sheet.
Figure 45A:
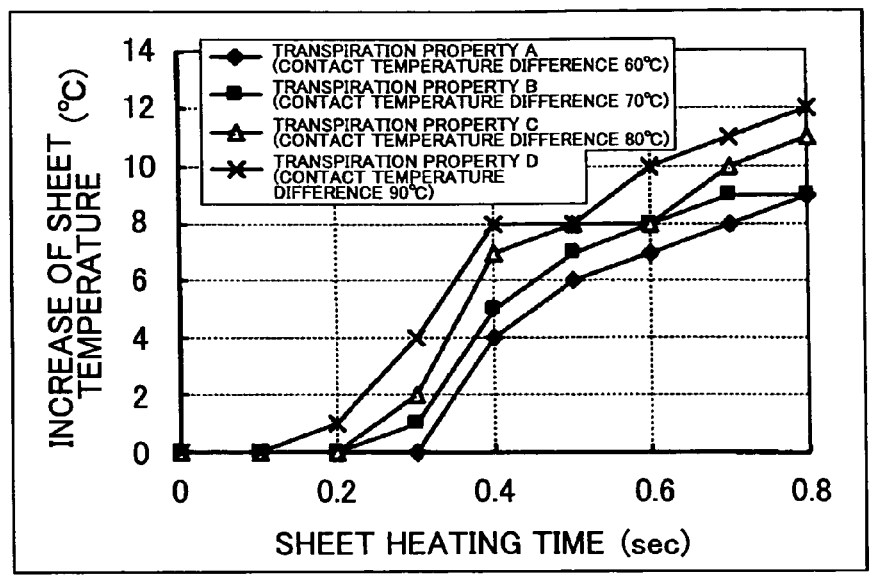
FIGS. 45A, 45B, 45C are graphs of the temperature rise, the deformation amount, and the increase in the moisture transpiration amount of a recording sheet with respect to heating time of the recording sheet.
Figure 45B:
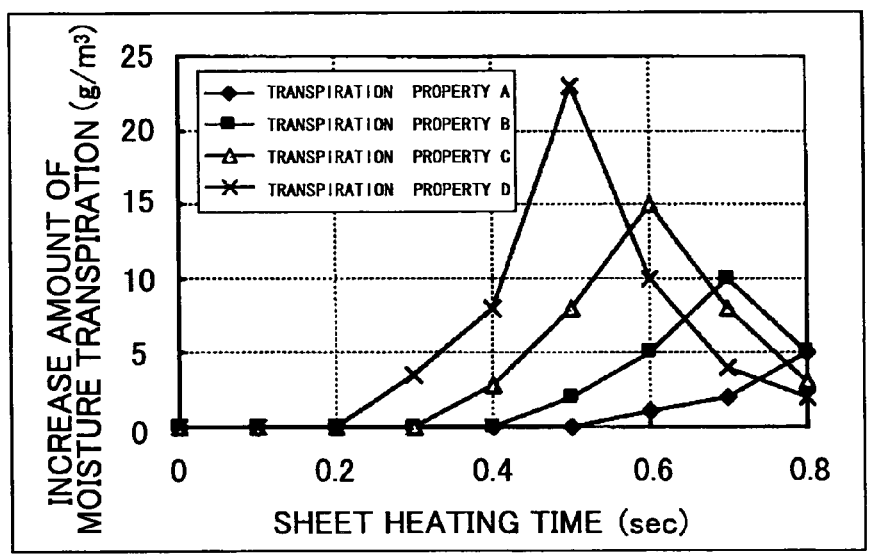
Figure 45C:
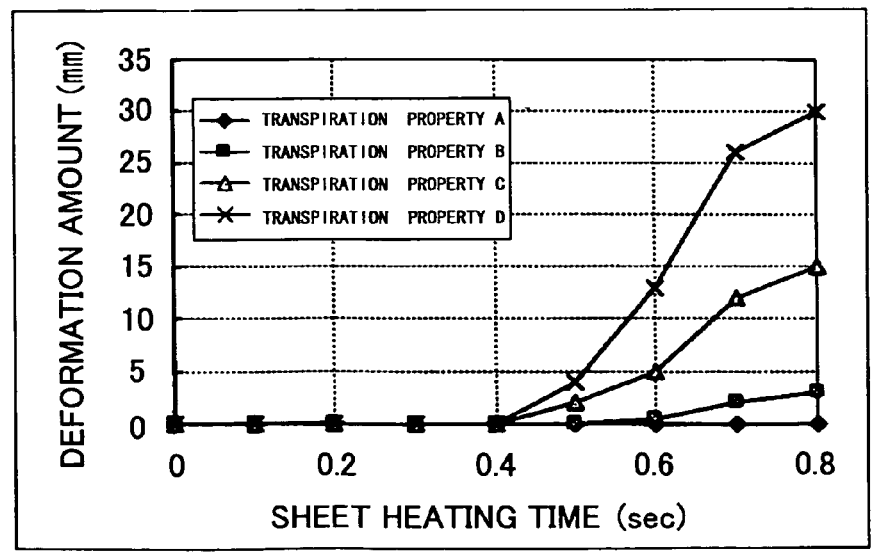
Figure 46A:
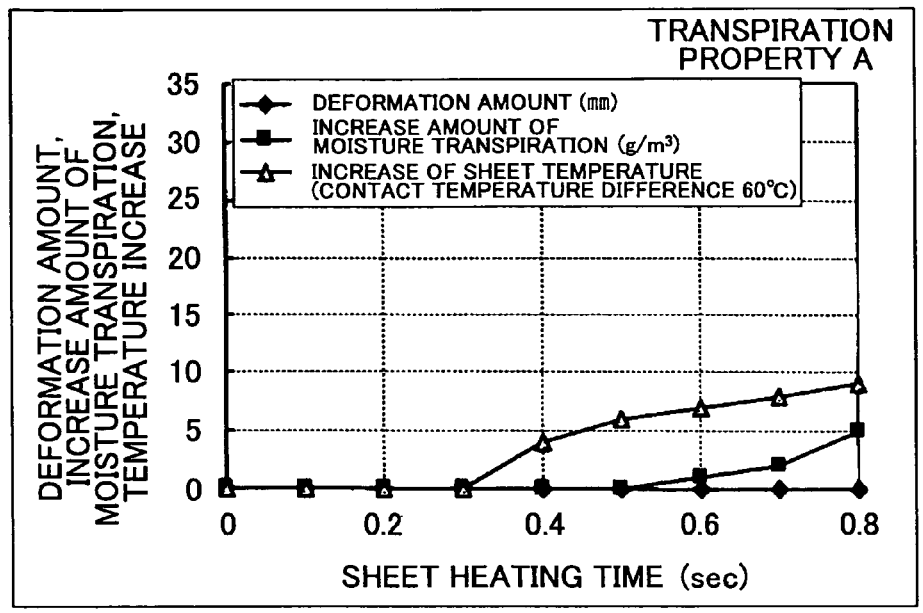
FIGS. 46A, 46B, 46C, 46D are variation property graphs of the temperature rise, the deformation amount, and the increase in the moisture transpiration amount of a recording sheet with respect to heating time of the recording sheet for different properties.
Figure 46B:
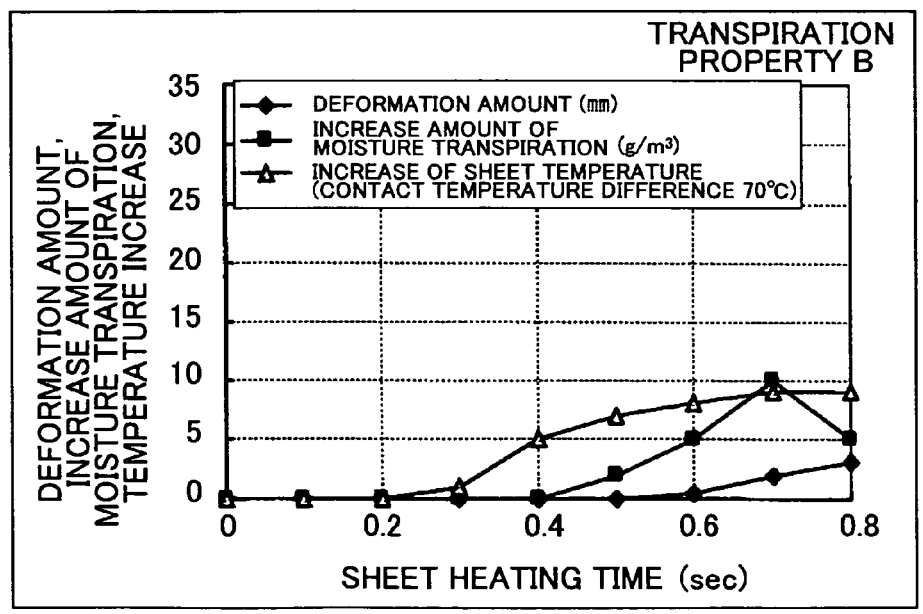
Figure 46C:
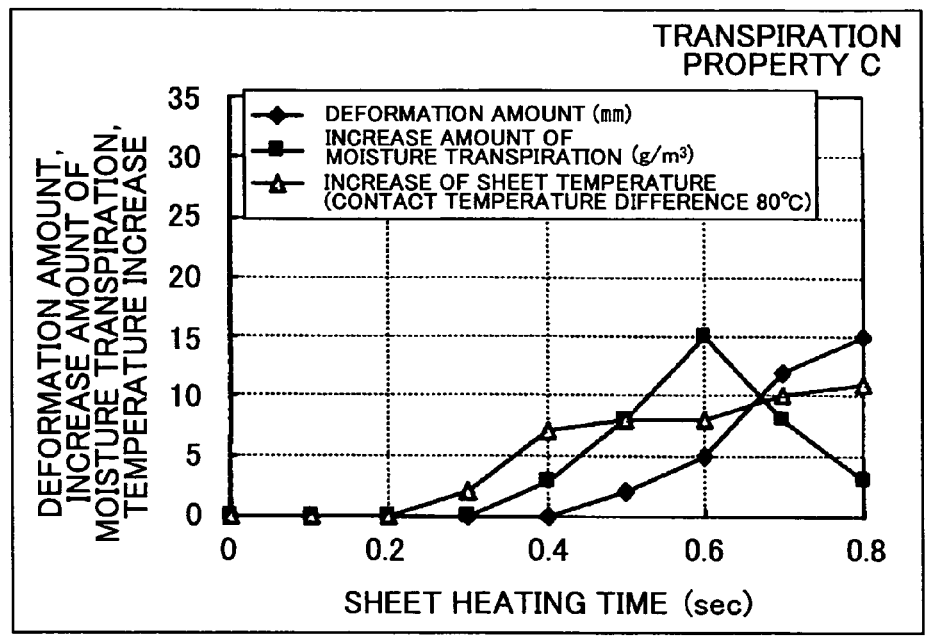
Figure 46D:
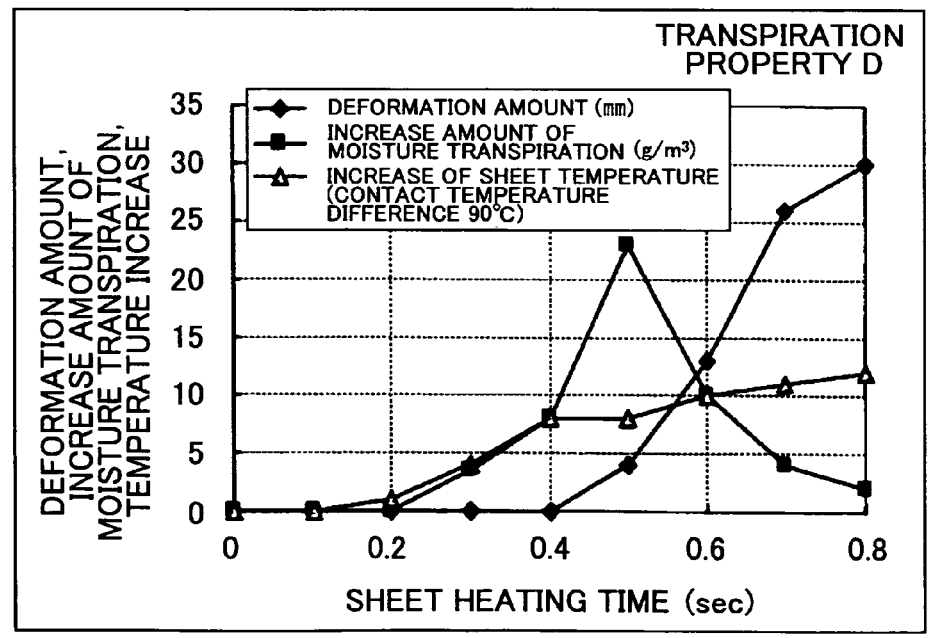

A description on how the recording sheet 390 deforms due to the transpiration behavior of moisture included in the recording sheet 390 is given below. The recording sheet 390 moves on a high-temperature heating member 401, as shown in FIG. 44. The transpiration behavior of moisture included in the recording sheet 390 in the non-contact condensation detecting apparatus 300 was examined by changing the temperature of the heating member 401, and the results are shown in FIGS. 45A, 45B, 45C, and FIGS. 46A, 46B, 46C, 46D. In FIGS. 45A, 45B, 45C, transpiration property A is when the contact temperature difference between the heating member 401 and the recording sheet 390 is 60° C., transpiration property B is when the contact temperature difference between the heating member 401 and the recording sheet 390 is 70° C., transpiration property C is when the contact temperature difference between the heating member 401 and the recording sheet 390 is 80° C., and transpiration property D is when the contact temperature difference between the heating member 401 and the recording sheet 390 is 90° C. FIG. 45A indicates the variation in temperature increase of the recording sheet 390 with respect to the heating time of the recording sheet 390. FIG. 45B indicates the variation in the increase in the transpiration amount of moisture included in the recording sheet 390 with respect to the heating time of the recording sheet 390. FIG. 45C indicates the variation in the deformation amount α of the recording sheet 390 with respect to the heating time of the recording sheet 390. FIGS. 46A, 46B, 46C, 46D indicate the variation in the temperature increase, the increase in moisture transpiration, and the deformation amount of the recording sheet 390 for the transpiration properties A, B, C, and D, respectively.

As shown in FIGS. 45A, 45B, as the recording sheet 390 is heated and the temperature rises, the moisture included in the recording sheet 390 undergoes transpiration. As the contact temperature difference between the heating member 401 and the recording sheet 390 increases from 60° C. to 90° C., the transpiration amount and the transpiration speed (transpiration amount per time) gradually increase. After the moisture undergoes transpiration to some extent, the transpiration amount starts to decrease. As shown in FIGS. 45B, 45C, the faster the moisture transpiration speed, the greater the deformation amount α of the recording sheet 390, and the deformation amount changes more quickly. Accordingly, the amount of moisture included in the recording sheet 390 affects the extent of deformation of the recording sheet 390, and the deformation amount of the recording sheet 390 is determined by the moisture transpiration speed.

Sometimes, deformation of the recording sheet 390 does not occur as shown by transpiration property A, even though the moisture undergoes transpiration from the recording sheet 390. This means that the strength (body) of the recording sheet 390 affects deformation. Specifically, the recording sheet 390 is prevented from deforming immediately when moisture undergoes transpiration, due to its strength. Considering this property, even if recording sheet 390 contains a large amount of moisture, the deformation amount can be reduced by slowing down the transpiration speed, i.e., by drying the recording sheet 390 slowly.

Figure 47:
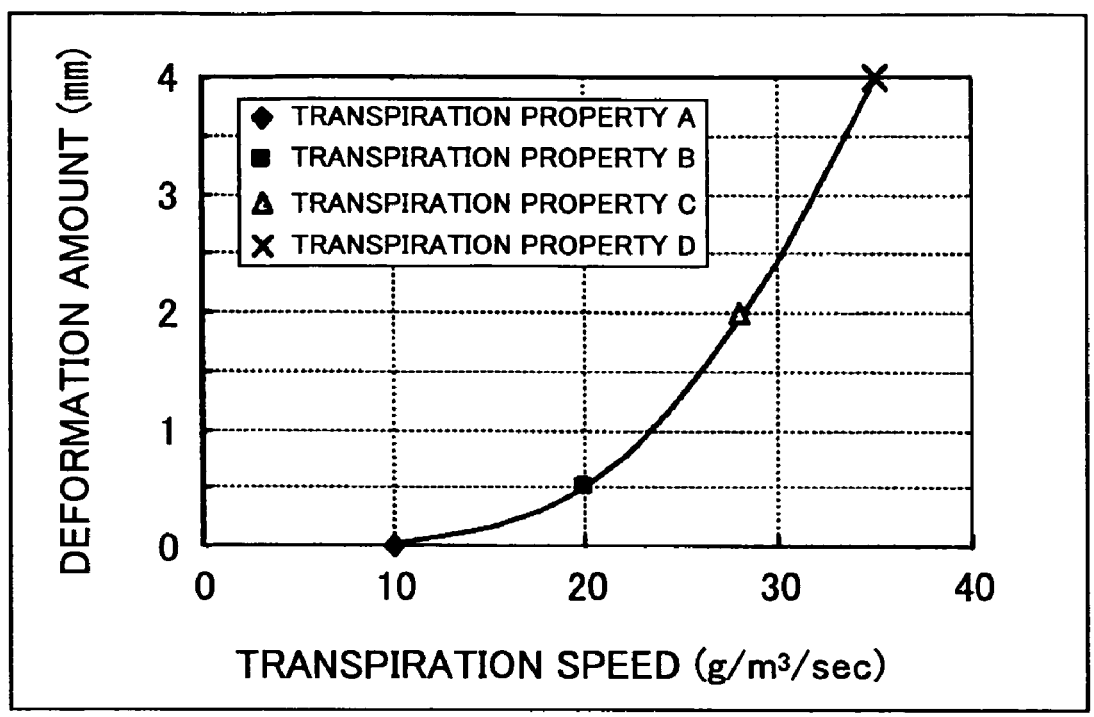
FIG. 47 is a variation property graph indicating the deformation amount of the recording sheet with respect to the transpiration speed.

The recording sheet 390 deforms, as shown in FIGS. 46A, 46B, 46C, 46D, due to transpiration behavior of moisture included in the recording sheet 390. Initially, the shape of the recording sheet 390 is maintained due to its strength. As moistures starts to undergo transpiration, the recording sheet 390 starts deforming. The deformation amount is larger when the transpiration speed is higher. Thus, the deformation amount of the recording sheet 390 can be predicted by measuring the transpiration speed before the recording sheet 390 starts deforming. FIG. 47 is a variation property graph indicating the deformation amount of the recording sheet 390 when 0.1 second has passed after deformation started, with respect to the transpiration speed from when transpiration starts, which is before the recording sheet 390 starts deforming, until 0.1 second passes. As shown in FIG. 47, the extent of deformation of the recording sheet 390 can be determined by measuring the transpiration speed from when transpiration starts, which is before the recording sheet 390 starts deforming, until 0.1 second passes.

As described above, the deformation amount of the recording sheet 390 can be determined by measuring the transpiration speed of the recording sheet 390. Further, deformation of the recording sheet 390 can be predicted by measuring transpiration speed when the transpiration starts and before the deformation with respect to the temperature applied to the recording sheet 390.

Figure 48A:
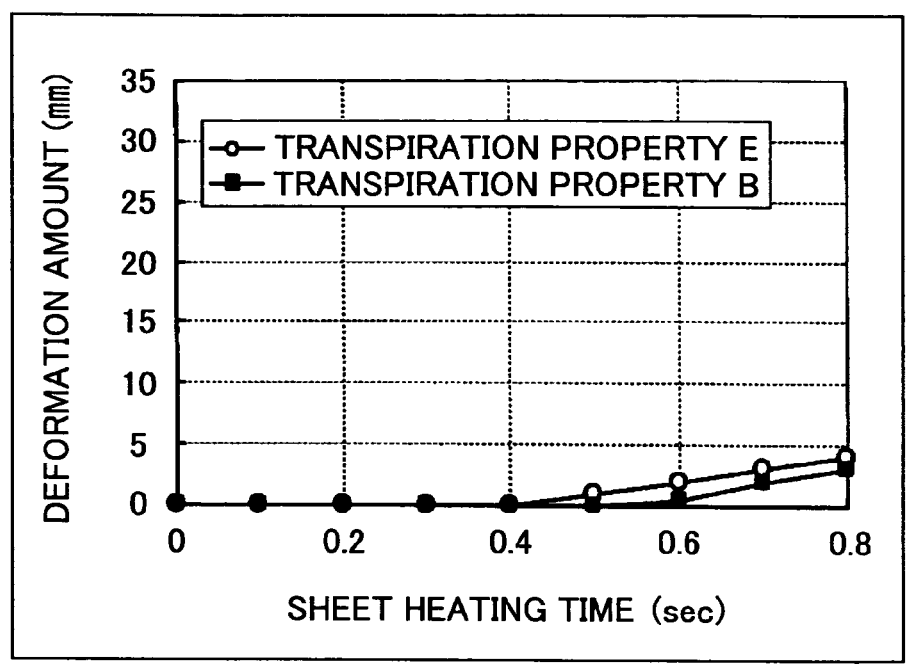
FIGS. 48A, 48B are variation property graphs of the transpiration amount of moisture for different types of recording sheets with respect to the heating time of recording sheets.
Figure 48B:
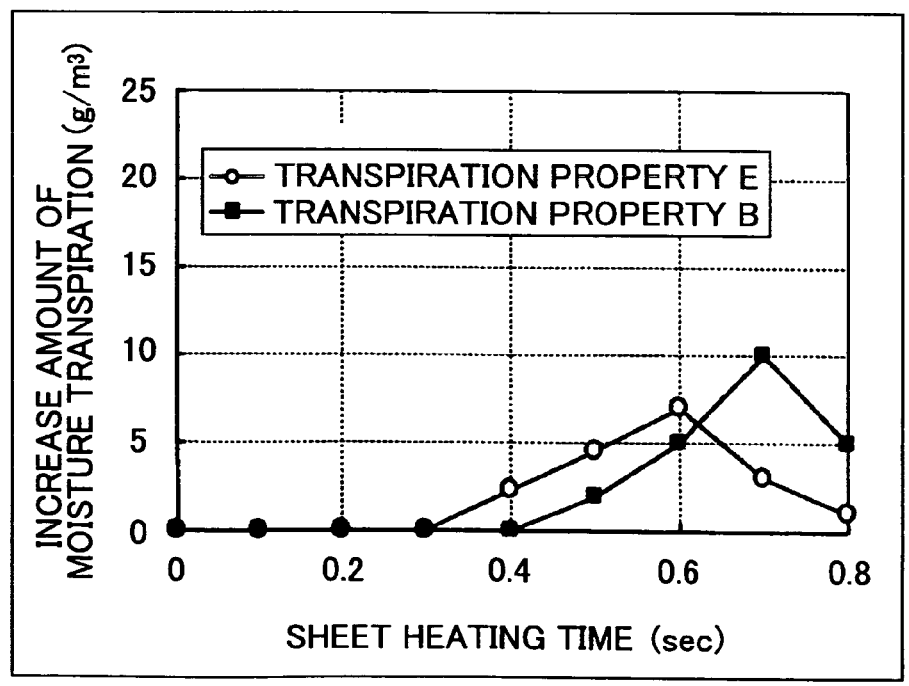

FIGS. 48A, 48B are variation property graphs of the transpiration amount of moisture for different types of recording sheets 39, when the contact temperature difference between the heating member 401 and the recording sheet 390 is 70° C. In FIGS. 48A, 48B, compared to the recording sheet 390 for transpiration property B, the recording sheet 390 for transpiration property E is thinner, has a smaller heat capacity, and has properties that make moisture undergo transpiration easily. As shown in FIGS. 48A, 48B, transpiration and deformation occur earlier for transpiration property E than for transpiration property B. In other words, the thicker recording sheet 390 has a stronger body. Accordingly, by detecting the transpiration behavior of moisture included in the recording sheet 390, i.e., the transpiration speed, the transpiration starting time, and temperature, it is possible to predict deformation of the recording sheet 390, and the deformation amount can be determined. This can be achieved without distinguishing the type of recording sheet 390. Although a special type of paper such as coated paper may need to be distinguished, plain paper such as recycled paper need not be distinguished.

As shown in FIG. 43, the following components are provided in a sheet conveying path in the image forming unit 3000 in order to detect transpiration behavior of the recording sheet 390. In an upstream side of the transferring unit 350 are disposed a first position sensor 415a and a first measurement unit 420a, which is, for example, the measurement unit 120c of the non-contact condensation detecting apparatus 300 shown in FIGS. 37A, 37B, 37C. On the downstream side of the transferring unit 350 in the sheet conveying path there are disposed a second position sensor 415b and a second measurement unit 420b. A third measurement unit 420c is disposed in the fixing unit 4000. The first position sensor 415a and the first measurement unit 420a are disposed at substantially the same position, and the second position sensor 415b and the second measurement unit 420b are disposed at substantially the same position.

Figure 49:
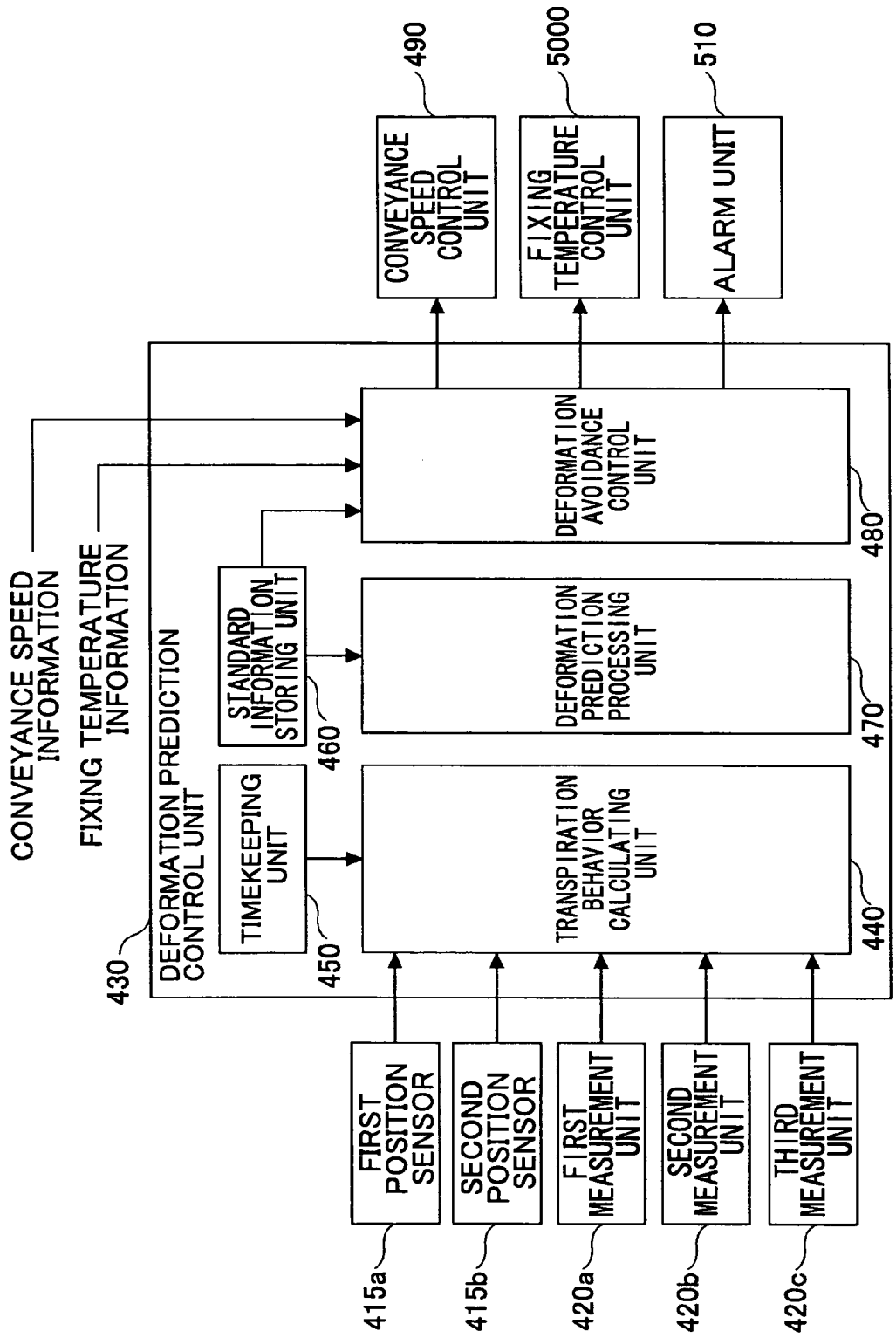
FIG. 49 is a block diagram of a deformation prediction control unit in a control unit of the image forming apparatus according to the present invention.

FIG. 49 is a block diagram of a deformation prediction control unit 430 in a control unit of the image forming apparatus. The deformation prediction control unit 430 predicts deformation of the recording sheet 390 based on detection results of the first position sensor 415a, the second position sensor 415b, the first measurement unit 420a, the second measurement unit 420b, and the third measurement unit 420c. The deformation prediction control unit 430 includes a transpiration behavior calculating unit 440, a timekeeping unit 450, a standard information storing unit 460, a deformation prediction processing unit 470, and a deformation avoidance control unit 480. The transpiration behavior calculating unit 440 detects the transpiration behavior of moisture included in the recording sheet 390 and calculates the transpiration amount, based on measurement signals received from the first measurement unit 420a, the second measurement unit 420b, and the third measurement unit 420c. Further, the transpiration behavior calculating unit 440 calculates the transpiration speed of moisture from the recording sheet 390 from the calculated transpiration amounts, and the time difference between when the first position sensor 415a and the second position sensor 415b respectively detect the leading edge of the recording sheet 390. In the standard information storing unit 460, the following information items are previously stored: a standard property indicating the temperature increase, the increase in the transpiration amount, and the deformation amount, with respect to the heating time of the recording sheet 390 as described with FIGS. 46A, 46B, 46C, 46D; and a standard value of transpiration speed from when transpiration starts before the recording sheet 390 starts deforming, until deformation starts e.g. after 0.1 second passes, as described with FIG. 47. The deformation prediction processing unit 470 compares the transpiration speed calculated by the transpiration behavior calculating unit 440 and the standard values stored in the standard information storing unit 460, and predicts deformation of the recording sheet 390 and determines how much the moisture transpiration amount increases in the fixing unit 4000. The deformation avoidance control unit 480 receives conveyance speed information of the recording sheet 390 and fixing temperature information of the fixing unit 4000. The deformation avoidance control unit 480 varies the conveyance speed information and the fixing temperature information received, based on deformation prediction information of the recording sheet 390 received from the deformation prediction processing unit 470, and a standard property indicating the temperature increase, the increase in the transpiration amount, and the deformation amount, with respect to the heating time, stored in the standard information storing unit 460. Accordingly, the deformation avoidance control unit 480 generates control information for conveyance speed and fixing temperature of the recording sheet 390, and outputs the control information to a conveyance speed control unit 490 and a fixing temperature control unit 505, which are equipped to control conveyance speed and fixing temperature for the recording sheet 390, respectively. Further, the deformation avoidance control unit 480 stops the recording sheet 390 from being conveyed and outputs an alarm signal to an alarm unit 510, when there is an abnormality in the deformation prediction information of the recording sheet 390 received from the deformation prediction processing unit 470, the transpiration amount, or the control information for conveyance speed and fixing temperature.

Figure 50:
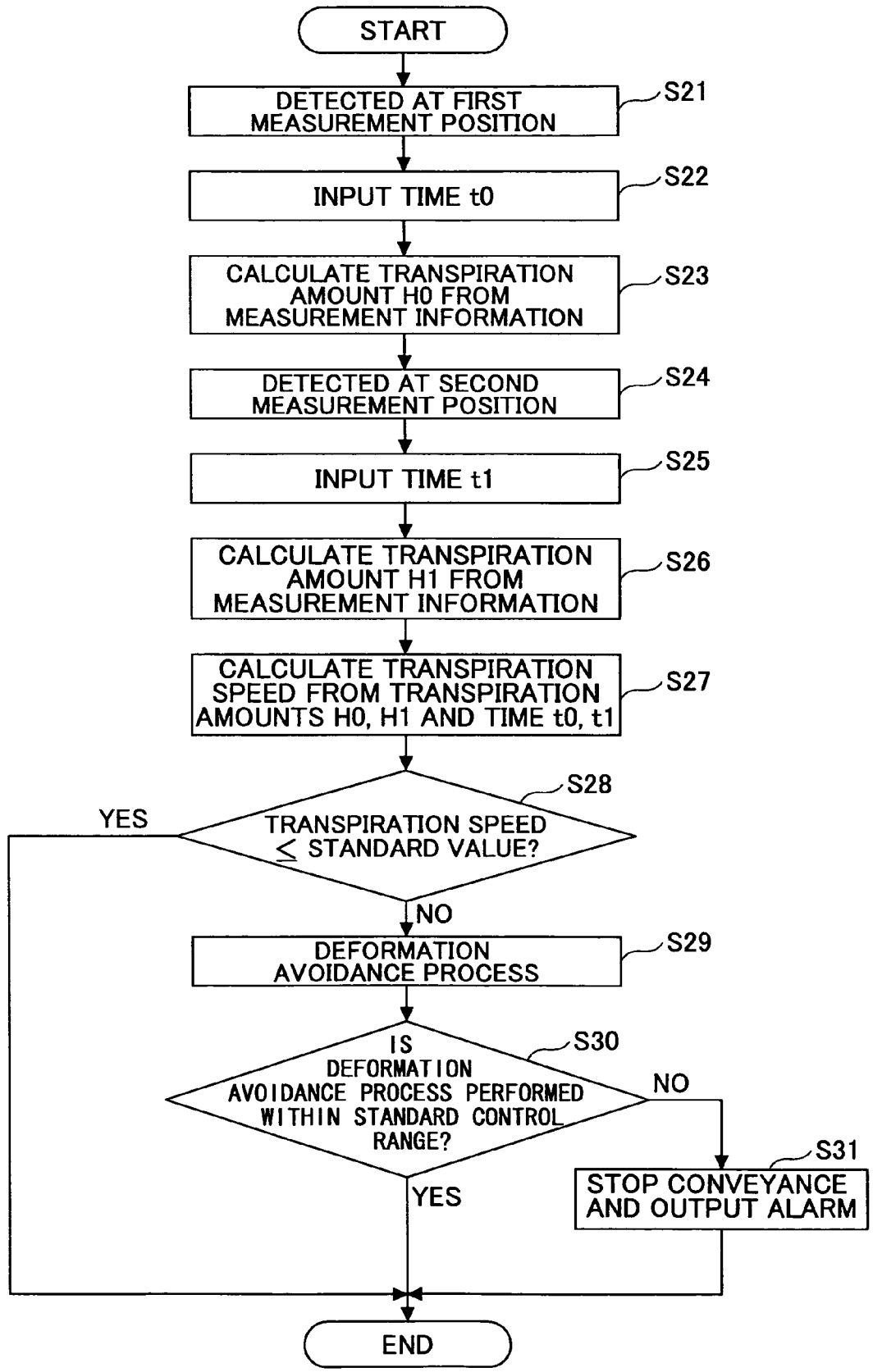
FIG. 50 is a flowchart of a deformation prediction/avoidance process of a recording sheet in the image forming unit.

A process performed by the deformation prediction control unit 430 for predicting deformation of the recording sheet 390 and avoiding deformation is described with reference to a flowchart in FIG. 50. The recording sheet 390 is conveyed to the image forming unit 3000, a toner image formed on the photoconductive drum 310 is transferred to the recording sheet 390, and the recording sheet 390 is conveyed to the fixing unit 4000.

When the image forming unit 3000 starts an image forming process, and the first position sensor 415a detects the leading edge of the recording sheet 390 being conveyed (step S21), the transpiration behavior calculating unit 440 receives a time t0 from the timekeeping unit 450 (step S22). After a predetermined timing determined by the positions of the first position sensor 415a and the first measurement unit 420a, the transpiration behavior calculating unit 440 calculates a transpiration amount H0, based on measurement information measured by the first measurement unit 420a indicating transpiration behavior of moisture included in the leading edge of the recording sheet 390 (step S23). The recording sheet 390 is conveyed to the transferring unit 350 where a toner image is transferred onto the recording sheet 390. As the recording sheet 390 is further conveyed to the fixing unit 4000, the second position sensor 415b detects the leading edge of the recording sheet 390 (step S24), and the transpiration behavior calculating unit 440 receives a time t1 from the timekeeping unit 450 (step S25). After a predetermined timing, the transpiration behavior calculating unit 440 calculates a transpiration amount H1, based on measurement information measured by the second measurement unit 420b indicating transpiration behavior of moisture included in the leading edge of the recording sheet 390 (step S26). After calculating the transpiration amount H1 based on the measurement information measured by the second measurement unit 420b, the transpiration behavior calculating unit 440 calculates a transpiration speed V by the following equality, based on the transpiration amount H0 calculated previously, the transpiration amount H1 calculated currently, and the time t0 and the time t1 at which the first position sensor 415a and the second position sensor 415b detected the leading edge of the recording sheet 390, respectively:

$$V = (H1 - H0)/(t1 - t0)$$

The transpiration behavior calculating unit 440 sends the calculated transpiration speed V to the deformation prediction processing unit 470 (step S27)

The transpiration behavior of moisture included in the leading edge of the recording sheet 390 is detected, because the edge of the recording sheet 390 conveyed to the image forming unit 3000 is well-ventilated, undergoes transpiration of a large amount of moisture to the surrounding environment, dries easily, and is likely to lack moisture. Therefore, the edge of the recording sheet 390 will quickly start to demonstrate a drying behavior, which significantly causes deformation of the recording sheet 390. The transpiration behavior of the leading edge of the recording sheet 390 is measured at the first position sensor 415a and at the second position sensor 415b, to obtain an accurate transpiration speed by measuring the same position of the recording sheet 390 that is being conveyed.

The deformation prediction processing unit 470 compares the transpiration speed V received with the standard value of transpiration speed, stored in the standard information storing unit 460, from when transpiration starts before the recording sheet 390 starts deforming, until a certain time when deformation starts. When the transpiration speed V is below the standard value (Yes in step S28), the deformation prediction processing unit 470 determines that the recording sheet 390 will not deform. When the transpiration speed V is equal to or higher than the standard value (No in step S28), the deformation prediction processing unit 470 determines that the recording sheet 390 will deform, and sends deformation prediction information to the deformation avoidance control unit 480. When the deformation prediction information is received, the deformation avoidance control unit 480 acquires the conveyance speed information of the recording sheet 390 and the fixing temperature information of the fixing unit 4000. The deformation avoidance control unit 480 varies the conveyance speed information and the fixing temperature information received, based on deformation prediction information of the recording sheet 390 being conveyed, and a standard property indicating the temperature increase, the increase in the transpiration amount, and the deformation amount, with respect to the heating time, stored in the standard information storing unit 460. Accordingly, the deformation avoidance control unit 480 generates control information for conveyance speed and fixing temperature for the recording sheet 390, and outputs the control information to the conveyance speed control unit 490 and the fixing temperature control unit 505 for the recording sheet 390. Based on the control information for conveyance speed and fixing temperature, the conveyance speed control unit 490 and the fixing temperature control unit 505 control the conveyance speed of the recording sheet 390 and the fixing temperature of the fixing unit 4000, respectively (hereinafter, "deformation avoidance process") (step S29). When the control information used for performing the deformation avoidance process is abnormal (No in step S30), the deformation avoidance control unit 480 stops the recording sheet 390 from being conveyed, and outputs an alarm signal to the alarm unit 510 (step S31).

As described above, the deformation avoidance control unit 480 calculates the transpiration speed V of moisture included in the recording sheet 390 before being sent to the fixing unit 4000, predicts whether deformation will occur, and performs the deformation avoidance process. Accordingly, it is possible to prevent the recording sheet 390 from deforming when heated by the fixing unit 4000, and thus prevent occurrence of a paper jam.

When the leading edge of the recording sheet 390 reaches the fixing unit 4000, the third measurement unit 420c measures the transpiration behavior of moisture included in the leading edge of the recording sheet 390, and inputs this measurement information to the transpiration behavior calculating unit 440. The transpiration behavior calculating unit 440 calculates a transpiration amount H2 based on the measurement information received, and sends the transpiration amount H2 to the deformation avoidance control unit 480. The deformation avoidance control unit 480 compares the transpiration amount H2 received with the standard property indicating the temperature increase, the increase in the transpiration amount, and the deformation amount, with respect to the heating time, stored in the standard information storing unit 460. When the transpiration amount H2 has increased more than a predetermined amount, the deformation avoidance control unit 480 outputs an alarm signal to the alarm unit 510.

By calculating the transpiration amount H2 of the recording sheet 390 to be fixed in the fixing unit 4000 based on measurement information received from the third measurement unit 420c, it is possible to confirm whether the recording sheet 390 will finally be deformed. Specifically, as the recording sheet 390 conveyed to the image forming unit 3000 approaches the fixing unit 4000, the amount of heat received by the recording sheet 390 increases. Due to this heat, the transpiration amount of moisture included in the recording sheet 390 gradually increases. When passing through the fixing unit 4000, maximum heat is applied to the recording sheet 390, such that the transpiration amount is large. It is possible to estimate how much the transpiration amount would increase in the fixing unit 4000, by calculating the transpiration amount H2 of the recording sheet 390 when entering the fixing unit 4000, based on the measurement information form the third measurement unit 420c.

For example, by using the measurement unit 120d of the non-contact condensation detecting apparatus 300 shown in FIGS. 37A, 37B, 37C, as the first measurement unit 420a, the second measurement unit 420b, and the third measurement unit 420c, the transpiration behavior of the recording sheet 390 can be measured in a non-contact manner. Accordingly, the transpiration behavior can be measured without affecting a toner image transferred onto the recording sheet 390, and a real-time transpiration amount can be obtained. Moreover, the measurement unit 120d of the non-contact condensation detecting apparatus 300 shown in FIGS. 37A, 37B, 37C is structured to include the rectifying tube 130. Therefore, the transpiration behavior can be measured accurately, without affecting the flow of transpiration at the measurement position of the recording sheet 390.

Figure 51:
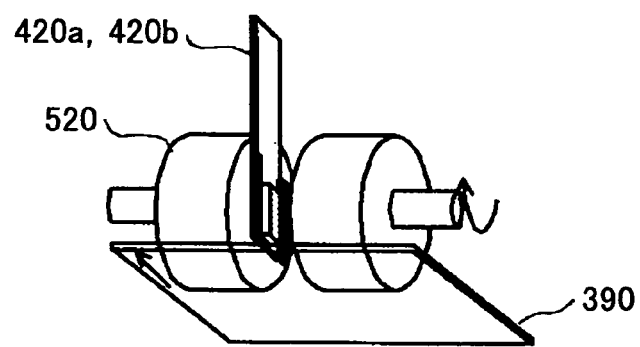
FIG. 51 is a perspective view of the position of the measurement unit with respect to a recording sheet.

As shown in FIG. 51, by incorporating the first measurement unit 420a and the second measurement unit 420b in between conveying rollers 520 in the sheet conveying path of the recording sheet 390, the spacing between the measurement units and the recording sheet 390 can be maintained precisely. The first measurement unit 420a and the second measurement unit 420b can be disposed near the conveying rollers 520. When a conveying belt is employed as a conveying means, the first measurement unit 420a and the second measurement unit 420b can be disposed at a certain distance from the conveying belt.

In the description above, the measurement unit 120d shown in FIGS. 37A, 37B, 37C is used as the first measurement unit 420a, the second measurement unit 420b, and the third measurement unit 420c. Alternatively, the measurement unit 120a shown in FIG. 35A, or the measurement unit 120b shown in FIG. 35B, or the measurement unit 120e shown in FIGS. 38A, 38B can be used.

Figure 52A:
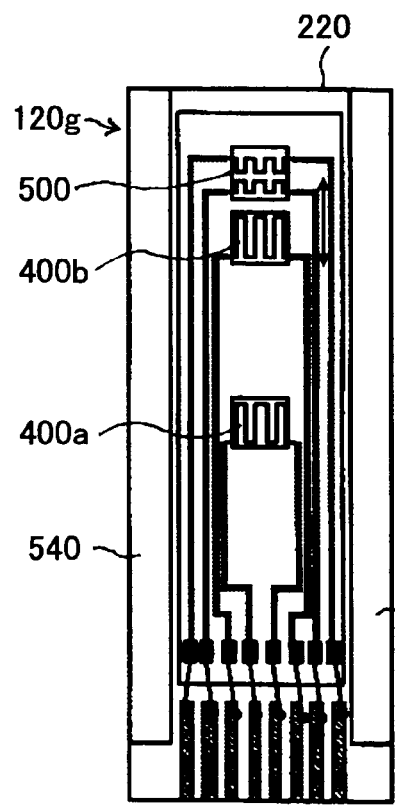
FIGS. 52A, 52B are diagrams of an eleventh example of a measurement unit.
Figure 52B:
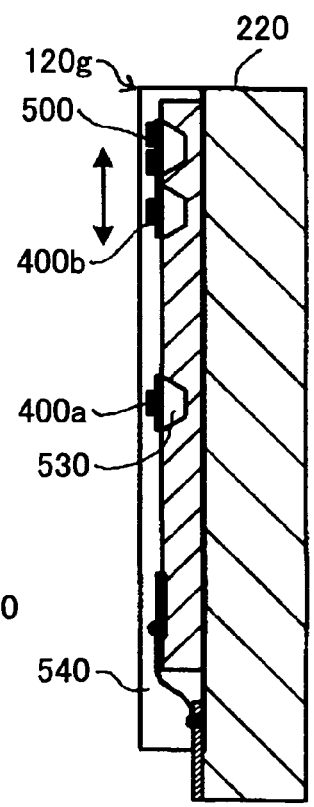

An eleventh example of a measurement unit 120g shown in FIGS. 52A, 52B can be used as the first measurement unit 420a, the second measurement unit 420b, or the third measurement unit 420c. As shown in a front view of FIG. 52A and a cross-sectional schematic diagram of FIG. 52B, the sensor substrate 220 includes voids 530 at positions where the humidity/temperature sensors 400a, 400b and the flowsensor 500 are disposed. The humidity/temperature sensors 400a, 400b and the flowsensor 500 are disposed along the flow direction of moisture transpiration. Flow path plates 540 are provided on both sides of the sensor substrate 220 to prevent the transpiration flow from fluctuating.

Figure 53A:
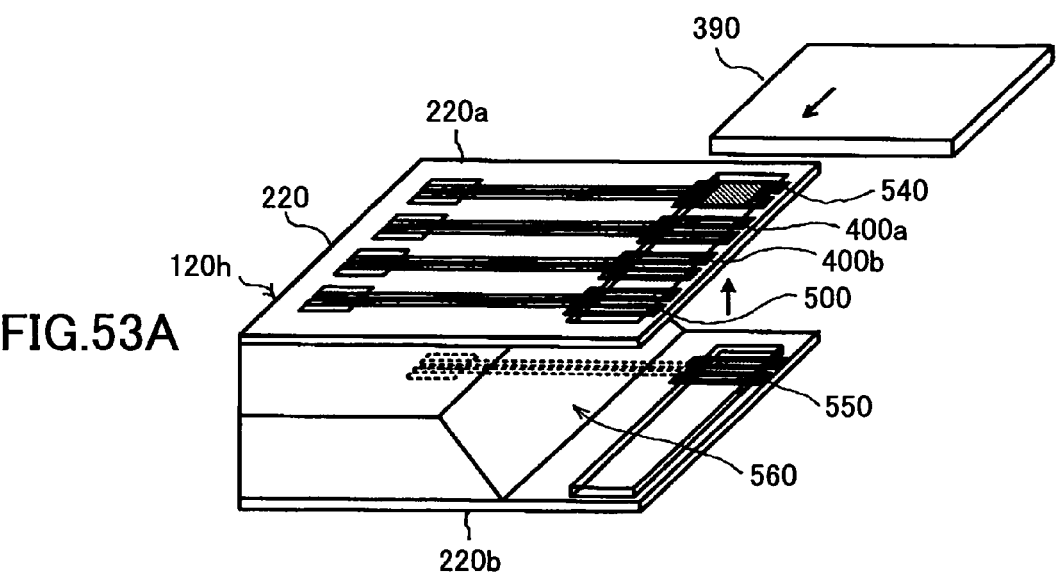
FIGS. 53A, 53B are diagrams of a twelfth example of a measurement unit.
Figure 53B:
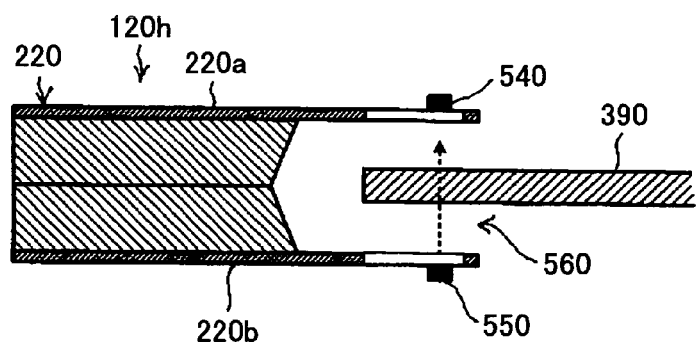

A twelfth example of a measurement unit 120h shown in FIGS. 53A, 53B can be used as the first measurement unit 420a, the second measurement unit 420b, or the third measurement unit 420c. As shown in a perspective view of FIG. 53A and a cross-sectional schematic diagram of FIG. 53B, on a top surface 220a of the sensor substrate 220, a pyroelectric element 540, such as a thermopile or a infrared sensor having a pyroelectric structure, the humidity/temperature sensors 400a, 400b, and the flowsensor 500 are disposed along the conveying direction of the recording sheet 390. A radiating element 550 is disposed on a bottom surface 220b of the sensor substrate 220, opposite the pyroelectric element 540. The center of the sensor substrate 220 is removed by etching, thereby forming a gap 560 for allowing a side edge of the recording sheet 390 pass through. When the measurement unit 120h is used as the first measurement unit 420a, the second measurement unit 420b, or the third measurement unit 420c, heat radiated from the radiating element 550 crosses the gap 560, and is detected by the pyroelectric element 540. When the recording sheet 390 is being conveyed through the gap 560, a slight amount of heat, e.g. several tens mW, radiated by the radiating element 550 in a short time, e.g. several tens ms, slightly increases the temperature at a small area at the edge of the recording sheet 390, e.g. by 0.1° C., and a slight amount of moisture undergoes transpiration. By measuring this transpiration behavior with the humidity/temperature sensors 400a, 400b and the flowsensor 500, the transpiration amount and the temperature can be measured. Moreover, when the recording sheet 390 is conveyed into the gap 560, by detecting the amount of infrared radiation penetrating the recording sheet 390 with the pyroelectric element 540, the quality (fiber density) of the recording sheet 390 and moisture included in the recording sheet 390 can be measured. Accordingly, precision in detecting sheet deformation can be enhanced.

The position sensor 415a can be provided on the sensor substrate 220. By providing the position sensor 415a on the sensor substrate 220, the transpiration occurring at the leading edge of the recording sheet 390 can be surely detected.

In the above description, the deformation prediction control unit 430 includes the transpiration behavior calculating unit 440, the deformation prediction processing unit 470, and the deformation avoidance control unit 480. However, as shown in a block diagram of FIG. 54, a CPU 570 can process the functions of the transpiration behavior calculating unit 440, the deformation prediction processing unit 470, and the deformation avoidance control unit 480. In this case, measurement information from the first position sensor 415a, the second position sensor 415b, the first measurement unit 420a, the second measurement unit 420b, and the third measurement unit 420c can be input to the CPU 570 from an input unit 580. The CPU performs the transpiration behavior calculation process, the deformation detection process, and the deformation avoidance process. An output unit 590 sends results of the processes to the conveyance speed control unit 490 and the fixing temperature control unit 505, which correct the conveyance velocity and the fixing temperature for the recording sheet 390. Accordingly, the recording sheet 390 is prevented from deforming.

In the above description, the first measurement unit 420a and the second measurement unit 420b are disposed on the upper side of the sheet conveying path of the recording sheet 390. However, the measurement units of the non-contact condensation detecting apparatus 300 are compact and respond quickly. Therefore, the measurement units can be disposed on a lower side of the sheet conveying path, to detect transpiration behavior from under the recording sheet 390, and obtain the transpiration amount.

An electrophotographic image forming apparatus is described above. However, the same technology can be applied to another type of image forming apparatus such as an ink-jet type, to prevent failures in sheet conveyance such as a paper jam.

According to one embodiment of the present invention, a sensor can be used generically.

Further, according to one embodiment of the present invention, distribution conditions of the surrounding environment on the object surface and transpiration processes can be measured accurately, and behaviors of dew condensation and transpiration on the object surface can be precisely detected in real time.

Further, according to one embodiment of the present invention, it is possible to reduce the distance of the area to be measured in the transportation direction of the atmosphere, measure the atmosphere that is not much influenced by fluctuations in the surrounding environment near the object surface, and accurately measure distribution conditions of the surrounding environment on the object surface and transpiration processes.

Further, according to one embodiment of the present invention, influence by fluctuations in the surrounding environment can be removed, and distribution conditions of the surrounding environment on the object surface and transpiration processes can be measured accurately.

Further, according to one embodiment of the present invention, without directly mounting a dew condensation sensor on the object surface, it is possible to detect processes of dew condensation on the object surface in a non-contact manner, accurately predict dew condensation and transpiration on the object surface, and efficiently prevent dew condensation.

Further, according to one embodiment of the present invention, it is possible to prevent deformation of a sheet caused by transpiration of moisture included in the sheet.

Further, according to one embodiment of the present invention, it is possible to prevent deformation of a recording sheet, so as to stably convey the recording sheet.

Further, according to one embodiment of the present invention, deformation of a recording sheet can be surely prevented by detecting the dryness caused by moisture transpiration at a portion of the recording sheet that significantly affects the deformation.

Further, according to one embodiment of the present invention, transpiration behavior is measured at the same portion of the recording sheet, so that an accurate transpiration speed can be obtained.

Further, according to one embodiment of the present invention, the transpiration amount of moisture included at the leading edge of the recording sheet can be surely measured, so that an accurate transpiration speed can be obtained.

The present invention also has the following aspects.

A detector element comprises:

a substrate including one of a through hole and a void;

a heating unit including a heat generating electrode bridged across said one of the through hole and the void, the heat generating electrode being warped, cantilevered, and standing up in space; and a temperature sensor including a temperature sensor electrode provided above said one of the through hole and the void, the temperature sensor electrode being warped, cantilevered, and standing up in space, wherein the temperature sensor measures heat quantity transported from the heating unit, and the heat generating electrode and the temperature sensor electrode are shaped like a curved surface of a pipe.

The detector element according to the present invention as described above has the heating unit disposed inside the temperature sensor and along a direction of a flow of a fluid.

The detector element according to the present invention as described above further comprises:

a resistive element including an electrode that is bridged across one of the through hole and the void, the electrode being sloped, wherein the resistive element generates heat and indicates a first resistance value in response to receiving a heat generation current at a heat generation timing, indicates a second resistance value in response to receiving a detection current at a detection timing, and a transported heat quantity is calculated based on a value obtained by subtracting the second resistance value from the first resistance value.

The detector element according to the present invention as described above further comprises:

a first resistive element including an electrode that is bridged across one of the through hole and the void, the electrode being sloped;

a second resistive element including an electrode that is bridged across one of the through hole and the void, the electrode being sloped; wherein the second resistive element measures heat quantity transported from the first resistive element, or the first resistive element measures heat quantity transported from the second resistive element.

A vacuum gauge comprises the detector element according to the present invention as described above enclosed in a vacuum container, wherein wires are extended from an electrode pad of the heating unit and an electrode pad of the temperature sensor to outside the vacuum container, the vacuum gauge is configured to acquire pressure dependence of heat conductivity of gas inside the vacuum container as temperature variation obtained from the temperature sensor, and to convert the acquired value into a degree of vacuum.

A vacuum gauge comprises the detector element according to the present invention as described above enclosed in a vacuum container, wherein wires are extended from an electrode pad of the heating unit and an electrode pad of the temperature sensor to outside of the vacuum container, and the heating unit serves as a filament, the temperature sensor serves as a grid, and the substrate serves as a collector, the vacuum gauge is configured to measure a current flowing between the filament and the collector, and to convert the measured current into a degree of vacuum.

A non-contact condensation detecting method comprises the steps of:

measuring distribution of an atmosphere surrounding an object surface with respect to the object surface and a transportation state of the atmosphere, by using at least one of temperature, humidity, a direction or velocity of flow, pressure, and composition of gas in the atmosphere, measured at least at two locations, near the object surface and distant from the object surface, in two directions opposite to each other with respect to gas components being transported along gravity; and detecting a behavior of the gas adhering and aggregating onto the object surface, and a behavior of aggregated liquid transpiring from the object surface, based on a difference between values measured, at the measuring step, in the two directions opposite to each other with respect to gas components being transported along gravity.

The non-contact condensation detecting method according to the present invention as described above has a wall is disposed where the elements of the gas are measured, near the object surface and in the flow direction of the gas in the atmosphere, the wall providing friction resistance with respect to the gas of the atmosphere, and the wall is a cylindrical rectifying tube including a portion that has a smaller diameter than that of another portion thereof.

A sheet deformation preventing method comprises the steps of:

measuring a transpiration amount of a volatile component included in a sheet of any type according to the non-contact condensation detecting method according to the present invention as described above, calculating a transpiration speed, which is a transpiration amount per unit time, based on the measured transpiration amount, and setting drying conditions for the sheet such that the calculated transpiration speed does not exceed a standard value of transpiration speed for a predetermined period until the sheet starts deforming.

The sheet deformation preventing method according to an embodiment of the present invention as described above is provided, wherein, the measuring includes measuring a transpiration amount of a volatile component included in a leading edge of the sheet while the sheet is being conveyed, at plural locations along a sheet conveyance path.

The present invention is not limited to the specifically disclosed embodiment, and variations and modifications may be made without departing from the scope of the present invention.

The present application is based on Japanese Priority Patent Application No. 2005-198744, filed on Jul. 7, 2005, and Japanese Priority Patent Application No. 2006-147865, filed on May 29, 2006, the entire contents of which are hereby incorporated by reference.

What is claimed is:

1. A detector element comprising:
   a substrate including one of a through hole and a void;
   a heating unit including a heat generating electrode bridged across said one of the through hole and the void, the heat generating electrode being warped, cantilevered, and standing up in space; and
   a temperature sensor including a temperature sensor electrode provided above said one of the through hole and the void, the temperature sensor electrode being warped, cantilevered, and standing up in space; wherein
   the temperature sensor measures heat quantity transported from the heating unit.

2. The detector element according to claim 1, wherein
   the heating unit and the temperature sensor are disposed adjacent to each other, and
   the temperature sensor measures heat quantity transported by a fluid from the heating unit in accordance with one of a flow velocity and a flow rate of the fluid and heat conductivity of an atmosphere.

3. The detector element according to claim 1, wherein
   a flow velocity is measured based on a distance between the heating unit and the heat generating electrode, and time required for heat to be transported by a fluid from the heating unit in accordance with one of a flow velocity and a flow rate of the fluid and heat conductivity of an atmosphere.

4. The detector element according to claim 1, wherein
   the heating unit is disposed inside the temperature sensor and along a direction intersecting a flow of a fluid.

5. The detector element according to claim 1, wherein
   the temperature sensor electrode of the temperature sensor is ring-shaped, and
   the heat generating electrode of the heating unit is disposed at the center of the ring-shaped temperature sensor electrode of the temperature sensor.

6. The detector element according to claim 1, further comprising:
   a resistive element including an electrode that is bridged across said one of the through hole and the void, the electrode being warped, cantilevered, and standing up in space; wherein the resistive element generates heat and indicates a first resistance value in response to receiving a heat generation current at a heat generation timing,
and indicates a second resistance value in response to receiving a detection current at a detection timing, and
a transported heat quantity is calculated based on a value obtained by subtracting the second resistance value from the first resistance value.

* * * * *